US009309306B2

(12) United States Patent
Freytag et al.

(10) Patent No.: US 9,309,306 B2
(45) Date of Patent: Apr. 12, 2016

(54) ANTI-MCSP ANTIBODIES

(75) Inventors: Olivier Freytag, Ueken (CH); Guy Georges, Habach (DE); Ekkehard Moessner, Kreuzlingen (CH); Olaf Mundigl, Weilheim (DE); Gérald Tuffin, Mulhouse (FR); Pablo Umana, Wollerau (CH)

(73) Assignee: Roche Glycart AG, Schilieren (CH)

( * ) Notice: Subject to any disclaimer, the term of this patent is extended or adjusted under 35 U.S.C. 154(b) by 0 days.

(21) Appl. No.: 13/590,904

(22) Filed: Aug. 21, 2012

(65) Prior Publication Data

US 2013/0078251 A1 Mar. 28, 2013

(30) Foreign Application Priority Data

Aug. 23, 2011 (EP) ..................................... 11178393

(51) Int. Cl.
*C07K 16/18* (2006.01)
*C07K 16/46* (2006.01)
*C07K 16/30* (2006.01)
*A61K 39/00* (2006.01)

(52) U.S. Cl.
CPC .............. *C07K 16/18* (2013.01); *C07K 16/3053* (2013.01); *A61K 2039/505* (2013.01); *C07K 2317/24* (2013.01); *C07K 2317/33* (2013.01); *C07K 2317/41* (2013.01); *C07K 2317/732* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 6,602,684 | B1 | 8/2003 | Umana et al. |
| 7,393,531 | B2 | 7/2008 | Young et al. |
| 7,468,254 | B2 | 12/2008 | Young et al. |
| 8,318,165 | B2 | 11/2012 | Keler et al. |
| 2006/0223096 | A1 | 10/2006 | Umana et al. |
| 2008/0095785 | A2 | 4/2008 | Ferrone |
| 2008/0260635 | A1 | 10/2008 | Young et al. |
| 2009/0098045 | A1 | 4/2009 | Young et al. |
| 2010/0150918 | A1 | 6/2010 | Kufer et al. |
| 2010/0303816 | A1* | 12/2010 | Keler et al. ................. 424/136.1 |
| 2011/0064751 | A1 | 3/2011 | Mossner et al. |
| 2013/0058936 | A1 | 3/2013 | Bruenker et al. |
| 2013/0078249 | A1 | 3/2013 | Ast et al. |
| 2013/0078250 | A1 | 3/2013 | Ast et al. |

FOREIGN PATENT DOCUMENTS

| | | |
|---|---|---|
| WO | 97/13855 | 4/1997 |
| WO | 99/54342 | 10/1999 |
| WO | 00/47228 | 8/2000 |
| WO | 02/079255 | 10/2002 |
| WO | 2006/032127 | 3/2006 |
| WO | 2008/030625 | 3/2008 |
| WO | 2008/095785 | 8/2008 |

OTHER PUBLICATIONS

Rudikoff et al. (Proceedings of the National Academy of Science USA, 1982, 79:1979).*
MacCallum et al (Journal of Molecular Biology, 1996, 262:732-745).*
Pascalis et al (The Journal of Immunology, 2002, 169, 3076-3084).*
Casset et al (Biochemical and Biophysical Research Communications, 2003, 307:198-205).*
Vajdos et al (Journal of Molecular Biology, 2002, 320:415-428).*
Chen et al (Journal of Molecular Biology, 1999, 293:865-881).*
Wu et al (Journal of Molecular Biology, 1999, 294:151-162).*
Padlan et al (Proceedings of the National Academy of Sciences, 1989, 86:5938-5942).*
Lamminmaki et al (Journal of Biological Chemistry, 2001, 276:36687-36694).*
Bluemel et al., "Impact of binding epitope and antigen size on the cytotoxic activity of MCSP-specific BiTE antibodies for treatment of melanoma" Proceedings of the American Association for Cancer Research Annual Meetings 51:1294 (2010).
Campoli et al., "Human High Molecular Weight-Melanoma-Associated Antigen (HMW-MAA): A Melanoma Cell Surface Chondroitin Sulfate Proteoglycan (MSCP) with Biological and Clinical Significance" Criticalk Reviews in Immunology 24(4):267-296 ( 2004).
IPRP for PCT/EP2012/066214 ( Feb. 25, 2014).
ISR for PCT/EP2012/066214.
Luo et al., "Targeting Melanoma Cells with Human High Molecular Weight-Melanoma Associated Antigen-Specific Antibodies Elicited by a Peptide Mimotope: Functional Effects" J. Immuno 176:6046-6054 ( 2006).
Mossner et al., "Abstract LB-236: M4-ML2, a novel glycoengineered humanized igG1 antibody, targeting a membrane-proximal epitope of MCSP/CSPG4 exhibits potent ADCC induction in vitro and in vivo anti-tumoral efficacy in disseminated melanoma models" Cancer Research 72(8) ( 2012).
Shields et al. et al., "Lack of Fucose on Human IgG1 N-Linked Oligosaccharide Improves Binding to Human FcγRIII and Antibody-dependent Cellular Toxicity" J Biol Chem 277(30):26733-26740 (Jul. 26, 2002).
Staube et al., "A novel repeat in the melanoma-associated chondroitin sulfate" FEBS Letters 527:114-118 ( 2002).
Umana et al., "Engineered glycoforms of an antineuroblastoma IgG1 with optimized antibody-dependent cellular cytotoxic activity" Nat Biotechnol 17:176-180 (Feb. 1999).
Vergilis et al., "Presence and Prognostic Significance of Melanoma-Associated" J. Invest Dermatol 125:526-531 ( 2005).
Yang et al., "Melanoma chondroitin sulfate proteoglycan enhances" J. Biol. Chem. 165:881-891 ( 2004).

* cited by examiner

*Primary Examiner* — Sean Aeder
*Assistant Examiner* — Julie Wu

(57) ABSTRACT

The invention provides anti-MCSP antibodies and methods of using the same.

21 Claims, 13 Drawing Sheets

```
                        SEQUENCE LISTING

<160> NUMBER OF SEQ ID NOS: 44

<210> SEQ ID NO 1
<211> LENGTH: 2322
<212> TYPE: PRT
<213> ORGANISM: Homo sapiens

<400> SEQUENCE: 1

Met Gln Ser Gly Pro Arg Pro Pro Leu Pro Ala Pro Gly Leu Ala Leu
1               5                   10                  15

Ala Leu Thr Leu Thr Met Leu Ala Arg Leu Ala Ser Ala Ala Ser Phe
                20                  25                  30

Phe Gly Glu Asn His Leu Glu Val Pro Val Ala Thr Ala Leu Thr Asp
            35                  40                  45

Ile Asp Leu Gln Leu Gln Phe Ser Thr Ser Gln Pro Glu Ala Leu Leu
        50                  55                  60

Leu Leu Ala Ala Gly Pro Ala Asp His Leu Leu Leu Gln Leu Tyr Ser
65                  70                  75                  80

Gly Arg Leu Gln Val Arg Leu Val Leu Gly Gln Glu Glu Leu Arg Leu
                85                  90                  95

Gln Thr Pro Ala Glu Thr Leu Leu Ser Asp Ser Ile Pro His Thr Val
            100                 105                 110

Val Leu Thr Val Val Glu Gly Trp Ala Thr Leu Ser Val Asp Gly Phe
        115                 120                 125

Leu Asn Ala Ser Ser Ala Val Pro Gly Ala Pro Leu Glu Val Pro Tyr
    130                 135                 140

Gly Leu Phe Val Gly Gly Thr Gly Thr Leu Gly Leu Pro Tyr Leu Arg
```

-continued

```
            145                 150                 155                 160
Gly Thr Ser Arg Pro Leu Arg Gly Cys Leu His Ala Ala Thr Leu Asn
                165                 170                 175
Gly Arg Ser Leu Leu Arg Pro Leu Thr Pro Asp Val His Glu Gly Cys
            180                 185                 190
Ala Glu Glu Phe Ser Ala Ser Asp Asp Val Ala Leu Gly Phe Ser Gly
                195                 200                 205
Pro His Ser Leu Ala Ala Phe Pro Ala Trp Gly Thr Gln Asp Glu Gly
            210                 215                 220
Thr Leu Glu Phe Thr Leu Thr Thr Gln Ser Arg Gln Ala Pro Leu Ala
225                 230                 235                 240
Phe Gln Ala Gly Gly Arg Arg Gly Asp Phe Ile Tyr Val Asp Ile Phe
                245                 250                 255
Glu Gly His Leu Arg Ala Val Val Glu Lys Gly Gln Gly Thr Val Leu
                260                 265                 270
Leu His Asn Ser Val Pro Val Ala Asp Gly Gln Pro His Glu Val Ser
            275                 280                 285
Val His Ile Asn Ala His Arg Leu Glu Ile Ser Val Asp Gln Tyr Pro
            290                 295                 300
Thr His Thr Ser Asn Arg Gly Val Leu Ser Tyr Leu Glu Pro Arg Gly
305                 310                 315                 320
Ser Leu Leu Leu Gly Gly Leu Asp Ala Glu Ala Ser Arg His Leu Gln
                325                 330                 335
Glu His Arg Leu Gly Leu Thr Pro Glu Ala Thr Asn Ala Ser Leu Leu
            340                 345                 350
Gly Cys Met Glu Asp Leu Ser Val Asn Gly Gln Arg Arg Gly Leu Arg
            355                 360                 365
Glu Ala Leu Leu Thr Arg Asn Met Ala Ala Gly Cys Arg Leu Glu Glu
            370                 375                 380
Glu Glu Tyr Glu Asp Asp Ala Tyr Gly His Tyr Glu Ala Phe Ser Thr
385                 390                 395                 400
Leu Ala Pro Glu Ala Trp Pro Ala Met Glu Leu Pro Glu Pro Cys Val
                405                 410                 415
Pro Glu Pro Gly Leu Pro Pro Val Phe Ala Asn Phe Thr Gln Leu Leu
            420                 425                 430
Thr Ile Ser Pro Leu Val Val Ala Glu Gly Gly Thr Ala Trp Leu Glu
            435                 440                 445
Trp Arg His Val Gln Pro Thr Leu Asp Leu Met Glu Ala Glu Leu Arg
            450                 455                 460
Lys Ser Gln Val Leu Phe Ser Val Thr Arg Gly Ala Arg His Gly Glu
465                 470                 475                 480
Leu Glu Leu Asp Ile Pro Gly Ala Gln Ala Arg Lys Met Phe Thr Leu
                485                 490                 495
Leu Asp Val Val Asn Arg Lys Ala Arg Phe Ile His Asp Gly Ser Glu
                500                 505                 510
Asp Thr Ser Asp Gln Leu Val Leu Glu Val Ser Val Thr Ala Arg Val
            515                 520                 525
Pro Met Pro Ser Cys Leu Arg Arg Gly Gln Thr Tyr Leu Leu Pro Ile
            530                 535                 540
Gln Val Asn Pro Val Asn Asp Pro Pro His Ile Ile Phe Pro His Gly
545                 550                 555                 560
Ser Leu Met Val Ile Leu Glu His Thr Gln Lys Pro Leu Gly Pro Glu
                565                 570                 575
```

-continued

Val Phe Gln Ala Tyr Asp Pro Asp Ser Ala Cys Glu Gly Leu Thr Phe
            580                 585                 590

Gln Val Leu Gly Thr Ser Ser Gly Leu Pro Val Glu Arg Arg Asp Gln
            595                 600                 605

Pro Gly Glu Pro Ala Thr Glu Phe Ser Cys Arg Glu Leu Glu Ala Gly
            610                 615                 620

Ser Leu Val Tyr Val His Arg Gly Pro Ala Gln Asp Leu Thr Phe
625                 630                 635                 640

Arg Val Ser Asp Gly Leu Gln Ala Ser Pro Ala Thr Leu Lys Val
                645                 650                 655

Val Ala Ile Arg Pro Ala Ile Gln Ile His Arg Ser Thr Gly Leu Arg
            660                 665                 670

Leu Ala Gln Gly Ser Ala Met Pro Ile Leu Pro Ala Asn Leu Ser Val
            675                 680                 685

Glu Thr Asn Ala Val Gly Gln Asp Val Ser Val Leu Phe Arg Val Thr
            690                 695                 700

Gly Ala Leu Gln Phe Gly Glu Leu Gln Lys Gln Gly Ala Gly Gly Val
705                 710                 715                 720

Glu Gly Ala Glu Trp Trp Ala Thr Gln Ala Phe His Gln Arg Asp Val
                725                 730                 735

Glu Gln Gly Arg Val Arg Tyr Leu Ser Thr Asp Pro Gln His His Ala
            740                 745                 750

Tyr Asp Thr Val Glu Asn Leu Ala Leu Glu Val Gln Val Gly Gln Glu
            755                 760                 765

Ile Leu Ser Asn Leu Ser Phe Pro Val Thr Ile Gln Arg Ala Thr Val
            770                 775                 780

Trp Met Leu Arg Leu Glu Pro Leu His Thr Gln Asn Thr Gln Gln Glu
785                 790                 795                 800

Thr Leu Thr Thr Ala His Leu Glu Ala Thr Leu Glu Glu Ala Gly Pro
                805                 810                 815

Ser Pro Pro Thr Phe His Tyr Glu Val Val Gln Ala Pro Arg Lys Gly
            820                 825                 830

Asn Leu Gln Leu Gln Gly Thr Arg Leu Ser Asp Gly Gln Gly Phe Thr
            835                 840                 845

Gln Asp Asp Ile Gln Ala Gly Arg Val Thr Tyr Gly Ala Thr Ala Arg
            850                 855                 860

Ala Ser Glu Ala Val Glu Asp Thr Phe Arg Phe Arg Val Thr Ala Pro
865                 870                 875                 880

Pro Tyr Phe Ser Pro Leu Tyr Thr Phe Pro Ile His Ile Gly Gly Asp
                885                 890                 895

Pro Asp Ala Pro Val Leu Thr Asn Val Leu Leu Val Val Pro Glu Gly
            900                 905                 910

Gly Glu Gly Val Leu Ser Ala Asp His Leu Phe Val Lys Ser Leu Asn
            915                 920                 925

Ser Ala Ser Tyr Leu Tyr Glu Val Met Glu Arg Pro Arg His Gly Arg
            930                 935                 940

Leu Ala Trp Arg Gly Thr Gln Asp Lys Thr Thr Met Val Thr Ser Phe
945                 950                 955                 960

Thr Asn Glu Asp Leu Leu Arg Gly Arg Leu Val Tyr Gln His Asp Asp
                965                 970                 975

Ser Glu Thr Thr Glu Asp Asp Ile Pro Phe Val Ala Thr Arg Gln Gly
            980                 985                 990

```
Glu Ser Ser Gly Asp Met Ala Trp Glu Glu Val Arg Gly Val Phe Arg
            995                 1000                1005

Val Ala Ile Gln Pro Val Asn Asp His Ala Pro Val Gln Thr Ile
    1010                1015                1020

Ser Arg Ile Phe His Val Ala Arg Gly Gly Arg Arg Leu Leu Thr
    1025                1030                1035

Thr Asp Asp Val Ala Phe Ser Asp Ala Asp Ser Gly Phe Ala Asp
    1040                1045                1050

Ala Gln Leu Val Leu Thr Arg Lys Asp Leu Leu Phe Gly Ser Ile
    1055                1060                1065

Val Ala Val Asp Glu Pro Thr Arg Pro Ile Tyr Arg Phe Thr Gln
    1070                1075                1080

Glu Asp Leu Arg Lys Arg Arg Val Leu Phe Val His Ser Gly Ala
    1085                1090                1095

Asp Arg Gly Trp Ile Gln Leu Gln Val Ser Asp Gly Gln His Gln
    1100                1105                1110

Ala Thr Ala Leu Leu Glu Val Gln Ala Ser Glu Pro Tyr Leu Arg
    1115                1120                1125

Val Ala Asn Gly Ser Ser Leu Val Val Pro Gln Gly Gly Gln Gly
    1130                1135                1140

Thr Ile Asp Thr Ala Val Leu His Leu Asp Thr Asn Leu Asp Ile
    1145                1150                1155

Arg Ser Gly Asp Glu Val His Tyr His Val Thr Ala Gly Pro Arg
    1160                1165                1170

Trp Gly Gln Leu Val Arg Ala Gly Gln Pro Ala Thr Ala Phe Ser
    1175                1180                1185

Gln Gln Asp Leu Leu Asp Gly Ala Val Leu Tyr Ser His Asn Gly
    1190                1195                1200

Ser Leu Ser Pro Arg Asp Thr Met Ala Phe Ser Val Glu Ala Gly
    1205                1210                1215

Pro Val His Thr Asp Ala Thr Leu Gln Val Thr Ile Ala Leu Glu
    1220                1225                1230

Gly Pro Leu Ala Pro Leu Lys Leu Val Arg His Lys Lys Ile Tyr
    1235                1240                1245

Val Phe Gln Gly Glu Ala Glu Ile Arg Arg Asp Gln Leu Glu
    1250                1255                1260

Ala Ala Gln Glu Ala Val Pro Pro Ala Asp Ile Val Phe Ser Val
    1265                1270                1275

Lys Ser Pro Pro Ser Ala Gly Tyr Leu Val Met Val Ser Arg Gly
    1280                1285                1290

Ala Leu Ala Asp Glu Pro Pro Ser Leu Asp Pro Val Gln Ser Phe
    1295                1300                1305

Ser Gln Glu Ala Val Asp Thr Gly Arg Val Leu Tyr Leu His Ser
    1310                1315                1320

Arg Pro Glu Ala Trp Ser Asp Ala Phe Ser Leu Asp Val Ala Ser
    1325                1330                1335

Gly Leu Gly Ala Pro Leu Glu Gly Val Leu Val Glu Leu Glu Val
    1340                1345                1350

Leu Pro Ala Ala Ile Pro Leu Glu Ala Gln Asn Phe Ser Val Pro
    1355                1360                1365

Glu Gly Gly Ser Leu Thr Leu Ala Pro Pro Leu Leu Arg Val Ser
    1370                1375                1380

Gly Pro Tyr Phe Pro Thr Leu Leu Gly Leu Ser Leu Gln Val Leu
```

```
            1385                1390                1395
Glu Pro Pro Gln His Gly Ala Leu Gln Lys Glu Asp Gly Pro Gln
    1400                1405                1410
Ala Arg Thr Leu Ser Ala Phe Ser Trp Arg Met Val Glu Glu Gln
    1415                1420                1425
Leu Ile Arg Tyr Val His Asp Gly Ser Glu Thr Leu Thr Asp Ser
    1430                1435                1440
Phe Val Leu Met Ala Asn Ala Ser Glu Met Asp Arg Gln Ser His
    1445                1450                1455
Pro Val Ala Phe Thr Val Thr Val Leu Pro Val Asn Asp Gln Pro
    1460                1465                1470
Pro Ile Leu Thr Thr Asn Thr Gly Leu Gln Met Trp Glu Gly Ala
    1475                1480                1485
Thr Ala Pro Ile Pro Ala Glu Ala Leu Arg Ser Thr Asp Gly Asp
    1490                1495                1500
Ser Gly Ser Glu Asp Leu Val Tyr Thr Ile Glu Gln Pro Ser Asn
    1505                1510                1515
Gly Arg Val Val Leu Arg Gly Ala Pro Gly Thr Glu Val Arg Ser
    1520                1525                1530
Phe Thr Gln Ala Gln Leu Asp Gly Gly Leu Val Leu Phe Ser His
    1535                1540                1545
Arg Gly Thr Leu Asp Gly Gly Phe Arg Phe Arg Leu Ser Asp Gly
    1550                1555                1560
Glu His Thr Ser Pro Gly His Phe Phe Arg Val Thr Ala Gln Lys
    1565                1570                1575
Gln Val Leu Leu Ser Leu Lys Gly Ser Gln Thr Leu Thr Val Cys
    1580                1585                1590
Pro Gly Ser Val Gln Pro Leu Ser Ser Gln Thr Leu Arg Ala Ser
    1595                1600                1605
Ser Ser Ala Gly Thr Asp Pro Gln Leu Leu Leu Tyr Arg Val Val
    1610                1615                1620
Arg Gly Pro Gln Leu Gly Arg Leu Phe His Ala Gln Gln Asp Ser
    1625                1630                1635
Thr Gly Glu Ala Leu Val Asn Phe Thr Gln Ala Glu Val Tyr Ala
    1640                1645                1650
Gly Asn Ile Leu Tyr Glu His Glu Met Pro Pro Glu Pro Phe Trp
    1655                1660                1665
Glu Ala His Asp Thr Leu Glu Leu Gln Leu Ser Ser Pro Pro Ala
    1670                1675                1680
Arg Asp Val Ala Ala Thr Leu Ala Val Ala Val Ser Phe Glu Ala
    1685                1690                1695
Ala Cys Pro Gln Arg Pro Ser His Leu Trp Lys Asn Lys Gly Leu
    1700                1705                1710
Trp Val Pro Glu Gly Gln Arg Ala Arg Ile Thr Val Ala Ala Leu
    1715                1720                1725
Asp Ala Ser Asn Leu Leu Ala Ser Val Pro Ser Pro Gln Arg Ser
    1730                1735                1740
Glu His Asp Val Leu Phe Gln Val Thr Gln Phe Pro Ser Arg Gly
    1745                1750                1755
Gln Leu Leu Val Ser Glu Glu Pro Leu His Ala Gly Gln Pro His
    1760                1765                1770
Phe Leu Gln Ser Gln Leu Ala Ala Gly Gln Leu Val Tyr Ala His
    1775                1780                1785
```

-continued

Gly Gly Gly Gly Thr Gln Gln Asp Gly Phe His Phe Arg Ala His
1790            1795                1800

Leu Gln Gly Pro Ala Gly Ala Ser Val Ala Gly Pro Gln Thr Ser
1805            1810                1815

Glu Ala Phe Ala Ile Thr Val Arg Asp Val Asn Glu Arg Pro Pro
1820            1825                1830

Gln Pro Gln Ala Ser Val Pro Leu Arg Leu Thr Arg Gly Ser Arg
1835            1840                1845

Ala Pro Ile Ser Arg Ala Gln Leu Ser Val Val Asp Pro Asp Ser
1850            1855                1860

Ala Pro Gly Glu Ile Glu Tyr Glu Val Gln Arg Ala Pro His Asn
1865            1870                1875

Gly Phe Leu Ser Leu Val Gly Gly Gly Leu Gly Pro Val Thr Arg
1880            1885                1890

Phe Thr Gln Ala Asp Val Asp Ser Gly Arg Leu Ala Phe Val Ala
1895            1900                1905

Asn Gly Ser Ser Val Ala Gly Ile Phe Gln Leu Ser Met Ser Asp
1910            1915                1920

Gly Ala Ser Pro Pro Leu Pro Met Ser Leu Ala Val Asp Ile Leu
1925            1930                1935

Pro Ser Ala Ile Glu Val Gln Leu Arg Ala Pro Leu Glu Val Pro
1940            1945                1950

Gln Ala Leu Gly Arg Ser Ser Leu Ser Gln Gln Gln Leu Arg Val
1955            1960                1965

Val Ser Asp Arg Glu Glu Pro Glu Ala Ala Tyr Arg Leu Ile Gln
1970            1975                1980

Gly Pro Gln Tyr Gly His Leu Leu Val Gly Gly Arg Pro Thr Ser
1985            1990                1995

Ala Phe Ser Gln Phe Gln Ile Asp Gln Gly Glu Val Val Phe Ala
2000            2005                2010

Phe Thr Asn Phe Ser Ser Ser His Asp His Phe Arg Val Leu Ala
2015            2020                2025

Leu Ala Arg Gly Val Asn Ala Ser Ala Val Val Asn Val Thr Val
2030            2035                2040

Arg Ala Leu Leu His Val Trp Ala Gly Gly Pro Trp Pro Gln Gly
2045            2050                2055

Ala Thr Leu Arg Leu Asp Pro Thr Val Leu Asp Ala Gly Glu Leu
2060            2065                2070

Ala Asn Arg Thr Gly Ser Val Pro Arg Phe Arg Leu Leu Glu Gly
2075            2080                2085

Pro Arg His Gly Arg Val Val Arg Val Pro Arg Ala Arg Thr Glu
2090            2095                2100

Pro Gly Gly Ser Gln Leu Val Glu Gln Phe Thr Gln Gln Asp Leu
2105            2110                2115

Glu Asp Gly Arg Leu Gly Leu Glu Val Gly Arg Pro Glu Gly Arg
2120            2125                2130

Ala Pro Gly Pro Ala Gly Asp Ser Leu Thr Leu Glu Leu Trp Ala
2135            2140                2145

Gln Gly Val Pro Pro Ala Val Ala Ser Leu Asp Phe Ala Thr Glu
2150            2155                2160

Pro Tyr Asn Ala Ala Arg Pro Tyr Ser Val Ala Leu Leu Ser Val
2165            2170                2175

```
Pro Glu Ala Ala Arg Thr Glu Ala Gly Lys Pro Glu Ser Ser Thr
    2180            2185            2190

Pro Thr Gly Glu Pro Gly Pro Met Ala Ser Ser Pro Glu Pro Ala
    2195            2200            2205

Val Ala Lys Gly Gly Phe Leu Ser Phe Leu Glu Ala Asn Met Phe
    2210            2215            2220

Ser Val Ile Ile Pro Met Cys Leu Val Leu Leu Leu Ala Leu
    2225            2230            2235

Ile Leu Pro Leu Leu Phe Tyr Leu Arg Lys Arg Asn Lys Thr Gly
    2240            2245            2250

Lys His Asp Val Gln Val Leu Thr Ala Lys Pro Arg Asn Gly Leu
    2255            2260            2265

Ala Gly Asp Thr Glu Thr Phe Arg Lys Val Glu Pro Gly Gln Ala
    2270            2275            2280

Ile Pro Leu Thr Ala Val Pro Gly Gln Gly Pro Pro Pro Gly Gly
    2285            2290            2295

Gln Pro Asp Pro Glu Leu Leu Gln Phe Cys Arg Thr Pro Asn Pro
    2300            2305            2310

Ala Leu Lys Asn Gly Gln Tyr Trp Val
    2315            2320

<210> SEQ ID NO 2
<211> LENGTH: 45
<212> TYPE: PRT
<213> ORGANISM: Homo sapiens

<400> SEQUENCE: 2

Ser Val Pro Glu Ala Ala Arg Thr Glu Ala Gly Lys Pro Glu Ser Ser
1               5                   10                  15

Thr Pro Thr Gly Glu Pro Gly Pro Met Ala Ser Ser Pro Glu Pro Ala
            20                  25                  30

Val Ala Lys Gly Gly Phe Leu Ser Phe Leu Glu Ala Asn
        35                  40                  45

<210> SEQ ID NO 3
<211> LENGTH: 107
<212> TYPE: PRT
<213> ORGANISM: Homo sapiens

<400> SEQUENCE: 3

Ile Leu Pro Ser Ala Ile Glu Val Gln Leu Arg Ala Pro Leu Glu Val
1               5                   10                  15

Pro Gln Ala Leu Gly Arg Ser Ser Leu Ser Gln Gln Leu Arg Val
            20                  25                  30

Val Ser Asp Arg Glu Glu Pro Glu Ala Ala Tyr Arg Leu Ile Gln Gly
        35                  40                  45

Pro Gln Tyr Gly His Leu Leu Val Gly Gly Arg Pro Thr Ser Ala Phe
    50                  55                  60

Ser Gln Phe Gln Ile Asp Gln Gly Glu Val Val Phe Ala Phe Thr Asn
65                  70                  75                  80

Phe Ser Ser Ser His Asp His Phe Arg Val Leu Ala Leu Ala Arg Gly
                85                  90                  95

Val Asn Ala Ser Ala Val Val Asn Val Thr Val
                100                 105

<210> SEQ ID NO 4
<211> LENGTH: 203
```

```
<212> TYPE: PRT
<213> ORGANISM: Homo sapiens
<220> FEATURE:
<221> NAME/KEY: DOMAIN
<222> LOCATION: (182)..(203)
<223> OTHER INFORMATION: Transmembrane Domain

<400> SEQUENCE: 4
```

Arg Ala Leu Leu His Val Trp Ala Gly Gly Pro Trp Pro Gln Gly Ala
1               5                   10                  15

Thr Leu Arg Leu Asp Pro Thr Val Leu Asp Ala Gly Glu Leu Ala Asn
            20                  25                  30

Arg Thr Gly Ser Val Pro Arg Phe Arg Leu Glu Gly Pro Arg His
        35                  40                  45

Gly Arg Val Val Arg Val Pro Arg Ala Arg Thr Glu Pro Gly Gly Ser
    50                  55                  60

Gln Leu Val Glu Gln Phe Thr Gln Gln Asp Leu Glu Asp Gly Arg Leu
65                  70                  75                  80

Gly Leu Glu Val Gly Arg Pro Gly Gly Arg Ala Pro Gly Pro Ala Gly
                85                  90                  95

Asp Ser Leu Thr Leu Glu Leu Trp Ala Gln Gly Val Pro Pro Ala Val
            100                 105                 110

Ala Ser Leu Asp Phe Ala Thr Glu Pro Tyr Asn Ala Ala Arg Pro Tyr
        115                 120                 125

Ser Val Ala Leu Leu Ser Val Pro Glu Ala Ala Arg Thr Glu Ala Gly
    130                 135                 140

Lys Pro Glu Ser Ser Thr Pro Thr Gly Glu Pro Gly Pro Met Ala Ser
145                 150                 155                 160

Ser Pro Glu Pro Ala Val Ala Lys Gly Gly Phe Leu Ser Phe Leu Glu
                165                 170                 175

Ala Asn Met Phe Ser Val Ile Ile Pro Met Cys Leu Val Leu Leu Leu
            180                 185                 190

Leu Ala Leu Ile Leu Pro Leu Leu Phe Tyr Leu
        195                 200

```
<210> SEQ ID NO 5
<211> LENGTH: 310
<212> TYPE: PRT
<213> ORGANISM: Homo sapiens
<220> FEATURE:
<221> NAME/KEY: Domain
<222> LOCATION: (289)..(310)
<223> OTHER INFORMATION: Transmembrane Domain

<400> SEQUENCE: 5
```

Ile Leu Pro Ser Ala Ile Glu Val Gln Leu Arg Ala Pro Leu Glu Val
1               5                   10                  15

Pro Gln Ala Leu Gly Arg Ser Ser Leu Ser Gln Gln Gln Leu Arg Val
            20                  25                  30

Val Ser Asp Arg Glu Gly Pro Gly Ala Ala Tyr Arg Leu Ile Gln Gly
        35                  40                  45

Pro Gln Tyr Gly His Leu Leu Val Gly Gly Arg Pro Thr Ser Ala Phe
    50                  55                  60

Ser Gln Phe Gln Ile Asp Gln Gly Glu Val Val Phe Ala Phe Thr Asn
65                  70                  75                  80

Phe Ser Ser Ser His Asp His Phe Arg Val Leu Ala Leu Ala Arg Gly
                85                  90                  95

Val Asn Ala Ser Ala Val Val Asn Val Thr Val Arg Ala Leu Leu His

```
                  100                 105                 110
Val Trp Ala Gly Gly Pro Trp Pro Gln Gly Ala Thr Leu Arg Leu Asp
            115                 120                 125

Pro Thr Val Leu Asp Ala Gly Glu Leu Ala Asn Arg Thr Gly Ser Val
        130                 135                 140

Pro Arg Phe Arg Leu Leu Glu Gly Pro Arg His Gly Arg Val Val Arg
145                 150                 155                 160

Val Pro Arg Ala Arg Thr Glu Pro Gly Gly Ser Gln Leu Val Glu Gln
                165                 170                 175

Phe Thr Gln Gln Asp Leu Glu Asp Gly Arg Leu Gly Leu Glu Val Gly
            180                 185                 190

Arg Pro Glu Gly Arg Ala Pro Gly Pro Ala Gly Asp Ser Leu Thr Leu
        195                 200                 205

Glu Leu Trp Ala Gln Gly Val Pro Pro Ala Val Ala Ser Leu Asp Phe
    210                 215                 220

Ala Thr Glu Pro Tyr Asn Ala Ala Arg Pro Tyr Ser Val Ala Leu Leu
225                 230                 235                 240

Ser Val Pro Glu Ala Ala Arg Thr Glu Ala Gly Lys Pro Glu Ser Ser
                245                 250                 255

Thr Pro Thr Gly Glu Pro Gly Pro Met Ala Ser Ser Pro Glu Pro Ala
            260                 265                 270

Val Ala Lys Gly Gly Phe Leu Ser Phe Leu Gly Ala Asn Met Phe Ser
        275                 280                 285

Val Ile Ile Pro Met Cys Leu Val Leu Leu Leu Ala Leu Ile Leu
    290                 295                 300

Pro Leu Leu Phe Tyr Leu
305                 310

<210> SEQ ID NO 6
<211> LENGTH: 419
<212> TYPE: PRT
<213> ORGANISM: Homo sapiens
<220> FEATURE:
<221> NAME/KEY: Domain
<222> LOCATION: (398)..(419)
<223> OTHER INFORMATION: Transmembrane Domain

<400> SEQUENCE: 6

Val Asn Glu Arg Pro Pro Gln Pro Gln Ala Ser Val Pro Leu Arg Leu
1               5                   10                  15

Thr Arg Gly Ser Arg Ala Pro Ile Ser Arg Ala Gln Leu Ser Val Val
            20                  25                  30

Asp Pro Asp Ser Ala Pro Gly Glu Ile Glu Tyr Glu Val Gln Arg Ala
        35                  40                  45

Pro His Asn Gly Phe Leu Ser Leu Val Gly Gly Leu Gly Pro Val
    50                  55                  60

Thr Arg Phe Thr Gln Ala Asp Val Asp Ser Gly Arg Leu Ala Phe Val
65                  70                  75                  80

Ala Asn Gly Ser Ser Val Ala Gly Ile Phe Gln Leu Ser Met Ser Asp
                85                  90                  95

Gly Ala Ser Pro Pro Leu Pro Met Ser Leu Ala Val Asp Ile Leu Pro
            100                 105                 110

Ser Ala Ile Glu Val Gln Leu Arg Ala Pro Leu Glu Val Pro Gln Ala
        115                 120                 125

Leu Gly Arg Ser Ser Leu Ser Gln Gln Gln Leu Arg Val Val Ser Asp
    130                 135                 140
```

```
Arg Glu Glu Pro Glu Ala Ala Tyr Arg Leu Ile Gln Gly Pro Gln Tyr
145                 150                 155                 160

Gly His Leu Leu Val Gly Gly Arg Pro Thr Ser Ala Phe Ser Gln Phe
                165                 170                 175

Gln Ile Asp Gln Gly Glu Val Val Phe Ala Phe Thr Asn Phe Ser Ser
            180                 185                 190

Ser His Asp His Phe Arg Val Leu Ala Leu Ala Arg Gly Val Asn Ala
        195                 200                 205

Ser Ala Val Val Asn Val Thr Val Arg Ala Leu Leu His Val Trp Ala
210                 215                 220

Gly Gly Pro Trp Pro Gln Gly Ala Thr Leu Arg Leu Asp Pro Thr Val
225                 230                 235                 240

Leu Asp Ala Gly Glu Leu Ala Asn Arg Thr Gly Ser Val Pro Arg Phe
                245                 250                 255

Arg Leu Leu Glu Gly Pro Arg His Gly Arg Val Val Arg Val Pro Arg
            260                 265                 270

Ala Arg Thr Glu Pro Gly Gly Ser Gln Leu Val Glu Gln Phe Thr Gln
        275                 280                 285

Gln Asp Leu Glu Asp Gly Arg Leu Gly Leu Glu Val Gly Arg Pro Glu
290                 295                 300

Gly Arg Ala Pro Gly Pro Ala Gly Asp Ser Leu Thr Leu Glu Leu Trp
305                 310                 315                 320

Ala Gln Gly Val Pro Pro Ala Val Ala Ser Leu Asp Phe Ala Thr Glu
                325                 330                 335

Pro Tyr Asn Ala Ala Arg Pro Tyr Ser Val Ala Leu Leu Ser Val Pro
            340                 345                 350

Glu Ala Ala Arg Thr Glu Ala Gly Lys Pro Glu Ser Ser Thr Pro Thr
        355                 360                 365

Gly Glu Pro Gly Pro Met Ala Ser Ser Pro Glu Pro Ala Val Ala Lys
370                 375                 380

Gly Gly Phe Leu Ser Phe Leu Glu Ala Asn Met Phe Ser Val Ile Ile
385                 390                 395                 400

Pro Met Cys Leu Val Leu Leu Leu Leu Ala Leu Ile Leu Pro Leu Leu
                405                 410                 415

Phe Tyr Leu

<210> SEQ ID NO 7
<211> LENGTH: 545
<212> TYPE: PRT
<213> ORGANISM: Homo sapiens
<220> FEATURE:
<221> NAME/KEY: Domain
<222> LOCATION: (524)..(545)
<223> OTHER INFORMATION: Transmembrane Domain

<400> SEQUENCE: 7

Gln His Pro Ser His Leu Trp Lys Asn Lys Gly Leu Trp Val Pro Glu
1               5                   10                  15

Gly Gln Arg Ala Arg Ile Thr Val Ala Ala Leu Asp Ala Ser Asn Leu
                20                  25                  30

Leu Ala Ser Val Pro Ser Pro Gln Arg Ser Glu His Asp Val Leu Phe
            35                  40                  45

Gln Val Thr Gln Phe Pro Ser Arg Gly Gln Leu Leu Val Ser Glu Glu
        50                  55                  60

Pro Leu His Ala Gly Gln Pro His Phe Leu Gln Ser Gln Leu Ala Ala
```

-continued

```
                65                  70                  75                  80
Gly Gln Leu Val Tyr Ala His Gly Gly Gly Thr Gln Gln Asp Gly
                    85                  90                  95
Phe His Phe Arg Ala His Leu Gln Gly Pro Ala Gly Ala Ser Val Ala
                100                 105                 110
Gly Pro Gln Thr Ser Glu Ala Phe Ala Ile Thr Val Arg Asp Val Asn
                115                 120                 125
Glu Arg Pro Pro Gln Pro Gln Ala Ser Val Pro Leu Arg Leu Thr Arg
            130                 135                 140
Gly Ser Arg Ala Pro Ile Ser Arg Ala Gln Leu Ser Val Val Asp Pro
145                 150                 155                 160
Asp Ser Ala Pro Gly Glu Ile Glu Tyr Glu Val Gln Arg Ala Pro His
                165                 170                 175
Asn Gly Phe Leu Ser Leu Val Gly Gly Leu Gly Pro Val Thr Arg
                180                 185                 190
Phe Thr Gln Ala Asp Val Asp Ser Gly Arg Leu Ala Phe Val Ala Asn
                195                 200                 205
Gly Ser Ser Val Ala Gly Ile Phe Gln Leu Ser Met Ser Asp Gly Ala
            210                 215                 220
Ser Pro Pro Leu Pro Met Ser Leu Ala Val Asp Ile Leu Pro Ser Ala
225                 230                 235                 240
Ile Glu Val Gln Leu Arg Ala Pro Leu Glu Val Pro Gln Ala Leu Gly
                245                 250                 255
Arg Ser Ser Leu Ser Gln Gln Leu Arg Val Val Ser Asp Arg Glu
                260                 265                 270
Glu Pro Glu Ala Ala Tyr Arg Leu Ile Gln Gly Pro Gln Tyr Gly His
            275                 280                 285
Leu Leu Val Gly Gly Arg Pro Thr Ser Ala Phe Ser Gln Phe Gln Ile
            290                 295                 300
Asp Gln Gly Glu Val Val Phe Ala Phe Thr Asn Phe Ser Ser Ser His
305                 310                 315                 320
Asp His Phe Arg Val Leu Ala Leu Ala Arg Gly Val Asn Ala Ser Ala
                325                 330                 335
Val Val Asn Val Thr Val Arg Ala Leu Leu His Val Trp Ala Gly Gly
                340                 345                 350
Pro Trp Pro Gln Gly Ala Thr Leu Arg Leu Asp Pro Thr Val Leu Asp
            355                 360                 365
Ala Gly Glu Leu Ala Asn Arg Thr Gly Ser Val Pro Arg Phe Arg Leu
            370                 375                 380
Leu Glu Gly Pro Arg His Gly Arg Val Val Arg Val Pro Arg Ala Arg
385                 390                 395                 400
Thr Glu Pro Gly Gly Ser Gln Leu Val Glu Gln Phe Thr Gln Gln Asp
                405                 410                 415
Leu Glu Asp Gly Arg Leu Gly Leu Glu Val Gly Arg Pro Glu Gly Arg
            420                 425                 430
Ala Pro Gly Pro Ala Gly Asp Ser Leu Thr Leu Glu Leu Trp Ala Gln
            435                 440                 445
Gly Val Pro Pro Ala Val Ala Ser Leu Asp Phe Ala Thr Glu Pro Tyr
            450                 455                 460
Asn Ala Ala Arg Pro Tyr Ser Val Ala Leu Leu Ser Val Pro Glu Ala
465                 470                 475                 480
Ala Arg Thr Glu Ala Gly Lys Pro Glu Ser Ser Thr Pro Thr Gly Glu
                485                 490                 495
```

```
Pro Gly Pro Met Ala Ser Ser Pro Glu Pro Ala Val Ala Lys Gly Gly
            500                 505                 510

Phe Leu Ser Phe Leu Glu Ala Asn Met Phe Ser Val Ile Ile Pro Met
        515                 520                 525

Cys Leu Val Leu Leu Leu Ala Leu Ile Leu Pro Leu Leu Phe Tyr
        530                 535                 540

Leu
545

<210> SEQ ID NO 8
<211> LENGTH: 643
<212> TYPE: PRT
<213> ORGANISM: Cynomologus

<400> SEQUENCE: 8

Leu Ser Leu Glu Gly Ser Arg Thr Leu Thr Val Cys Pro Gly Ser Val
1               5                   10                  15

Gln Pro Leu Ser Ser Gln Thr Leu Arg Ala Ser Ser Ala Gly Thr
            20                  25                  30

Asp Pro Gln Leu Leu Leu Tyr Arg Val Val Arg Gly Pro Gln Leu Gly
            35                  40                  45

Arg Leu Phe His Ala Gln Gln Asp Ser Thr Gly Glu Ala Leu Val Asn
        50                  55                  60

Phe Thr Gln Ala Glu Val Tyr Ala Gly Asn Ile Leu Tyr Glu His Glu
65                  70                  75                  80

Met Pro Thr Glu Pro Phe Trp Glu Ala His Asp Thr Leu Glu Leu Gln
                85                  90                  95

Leu Ser Ser Pro Pro Ala Arg Asp Val Ala Ala Thr Leu Ala Val Ala
            100                 105                 110

Val Ser Phe Glu Ala Ala Cys Pro Gln Arg Pro Ser His Leu Trp Lys
        115                 120                 125

Asn Lys Gly Leu Trp Val Pro Glu Gly Gln Arg Ala Lys Ile Thr Met
    130                 135                 140

Ala Ala Leu Asp Ala Ser Asn Leu Leu Ala Ser Val Pro Ser Pro Gln
145                 150                 155                 160

Arg Leu Glu His Asp Val Leu Phe Gln Val Thr Gln Phe Pro Ser Arg
                165                 170                 175

Gly Gln Leu Leu Val Ser Glu Glu Pro Leu His Ala Gly Gln Pro His
            180                 185                 190

Phe Leu Gln Ser Gln Leu Ala Ala Gly Gln Leu Val Tyr Ala His Gly
        195                 200                 205

Gly Gly Gly Thr Gln Gln Asp Gly Phe His Phe Arg Ala His Leu Gln
    210                 215                 220

Gly Pro Ala Gly Ala Thr Val Ala Gly Pro Gln Thr Ser Glu Ala Phe
225                 230                 235                 240

Ala Ile Thr Val Arg Asp Val Asn Glu Arg Pro Pro Gln Pro Gln Ala
                245                 250                 255

Ser Val Pro Leu Arg Ile Thr Arg Gly Ser Arg Ala Pro Ile Ser Arg
            260                 265                 270

Ala Gln Leu Ser Val Val Asp Pro Asp Ser Ala Pro Gly Glu Ile Glu
        275                 280                 285

Tyr Glu Val Gln Arg Ala Pro His Asn Gly Phe Leu Ser Leu Val Gly
    290                 295                 300

Gly Gly Pro Gly Pro Val Thr His Phe Thr Gln Ala Asp Val Asp Ser
```

```
                305                 310                 315                 320
        Gly Arg Leu Ala Phe Val Ala Asn Gly Ser Ser Val Ala Gly Val Phe
                        325                 330                 335

Gln Leu Ser Met Ser Asp Gly Ala Ser Pro Pro Leu Pro Met Ser Leu
                        340                 345                 350

Ala Val Asp Ile Leu Pro Ser Ala Ile Glu Val Gln Leu Gln Ala Pro
                        355                 360                 365

Leu Glu Val Pro Gln Ala Leu Gly Arg Ser Ser Leu Ser Gln Gln Gln
                        370                 375                 380

Leu Arg Val Val Ser Asp Arg Glu Glu Pro Glu Ala Ala Tyr Arg Leu
        385                 390                 395                 400

Ile Gln Gly Pro Lys Tyr Gly His Leu Leu Val Gly Gly Arg Pro Ala
                        405                 410                 415

Ser Ala Phe Ser Gln Leu Gln Ile Asp Gln Gly Glu Val Val Phe Ala
                        420                 425                 430

Phe Thr Asn Phe Ser Ser His Asp His Phe Arg Val Leu Ala Leu
                        435                 440                 445

Ala Arg Gly Val Asn Ala Ser Ala Val Val Asn Ile Thr Val Arg Ala
                        450                 455                 460

Leu Leu His Val Trp Ala Gly Gly Pro Trp Pro Gln Gly Ala Thr Leu
        465                 470                 475                 480

Arg Leu Asp Pro Thr Ile Leu Asp Ala Gly Glu Leu Ala Asn Arg Thr
                        485                 490                 495

Gly Ser Val Pro His Phe Arg Leu Leu Glu Gly Pro Arg His Gly Arg
                        500                 505                 510

Val Val Arg Val Pro Arg Ala Arg Thr Glu Pro Gly Gly Ser Gln Leu
                        515                 520                 525

Val Glu Gln Phe Thr Gln Gln Asp Leu Glu Asp Gly Arg Leu Gly Leu
                        530                 535                 540

Glu Val Gly Arg Pro Glu Gly Arg Ala Pro Ser Pro Thr Gly Asp Ser
        545                 550                 555                 560

Leu Thr Leu Glu Leu Trp Ala Gln Gly Val Pro Pro Ala Val Ala Ser
                        565                 570                 575

Leu Asp Phe Ala Thr Glu Pro Tyr Asn Ala Ala Arg Pro Tyr Ser Val
                        580                 585                 590

Ala Leu Leu Ser Val Pro Glu Ala Thr Arg Met Glu Ala Gly Lys Pro
                        595                 600                 605

Glu Ser Ser Thr Pro Thr Gly Glu Pro Gly Pro Met Ala Ser Ser Pro
                        610                 615                 620

Val Pro Ala Val Ala Lys Gly Gly Phe Leu Gly Phe Leu Glu Ala Asn
        625                 630                 635                 640

Met Phe Ser

<210> SEQ ID NO 9
<211> LENGTH: 643
<212> TYPE: PRT
<213> ORGANISM: Homo sapiens

<400> SEQUENCE: 9

Leu Ser Leu Lys Gly Ser Gln Thr Leu Thr Val Cys Pro Gly Ser Val
        1               5                   10                  15

Gln Pro Leu Ser Ser Gln Thr Leu Arg Ala Ser Ser Ser Ala Gly Thr
                        20                  25                  30

Asp Pro Gln Leu Leu Leu Tyr Arg Val Val Arg Gly Pro Gln Leu Gly
```

```
            35                  40                  45
Arg Leu Phe His Ala Gln Gln Asp Ser Thr Gly Glu Ala Leu Val Asn
        50                  55                  60
Phe Thr Gln Ala Glu Val Tyr Ala Gly Asn Ile Leu Tyr Glu His Glu
65                  70                  75                  80
Met Pro Pro Glu Pro Phe Trp Glu Ala His Asp Thr Leu Glu Leu Gln
                85                  90                  95
Leu Ser Ser Pro Pro Ala Arg Asp Val Ala Thr Leu Ala Val Ala
                    100                 105                 110
Val Ser Phe Glu Ala Ala Cys Pro Gln His Pro Ser His Leu Trp Lys
                115                 120                 125
Asn Lys Gly Leu Trp Val Pro Glu Gly Gln Arg Ala Arg Ile Thr Val
        130                 135                 140
Ala Ala Leu Asp Ala Ser Asn Leu Leu Ala Ser Val Pro Ser Pro Gln
145                 150                 155                 160
Arg Ser Glu His Asp Val Leu Phe Gln Val Thr Gln Phe Pro Ser Arg
                165                 170                 175
Gly Gln Leu Leu Val Ser Glu Glu Pro Leu His Ala Gly Gln Pro His
                    180                 185                 190
Phe Leu Gln Ser Gln Leu Ala Ala Gly Gln Leu Val Tyr Ala His Gly
                195                 200                 205
Gly Gly Gly Thr Gln Gln Asp Gly Phe His Phe Arg Ala His Leu Gln
        210                 215                 220
Gly Pro Ala Gly Ala Ser Val Ala Gly Pro Gln Thr Ser Glu Ala Phe
225                 230                 235                 240
Ala Ile Thr Val Arg Asp Val Asn Glu Arg Pro Pro Gln Pro Gln Ala
                    245                 250                 255
Ser Val Pro Leu Arg Leu Thr Arg Gly Ser Arg Ala Pro Ile Ser Arg
                260                 265                 270
Ala Gln Leu Ser Val Val Asp Pro Asp Ser Ala Pro Gly Glu Ile Glu
        275                 280                 285
Tyr Glu Val Gln Arg Ala Pro His Asn Gly Phe Leu Ser Leu Val Gly
        290                 295                 300
Gly Gly Leu Gly Pro Val Thr Arg Phe Thr Gln Ala Asp Val Asp Ser
305                 310                 315                 320
Gly Arg Leu Ala Phe Val Ala Asn Gly Ser Ser Val Ala Gly Ile Phe
                    325                 330                 335
Gln Leu Ser Met Ser Asp Gly Ala Ser Pro Pro Leu Pro Met Ser Leu
                340                 345                 350
Ala Val Asp Ile Leu Pro Ser Ala Ile Glu Val Gln Leu Arg Ala Pro
            355                 360                 365
Leu Glu Val Pro Gln Ala Leu Gly Arg Ser Ser Leu Ser Gln Gln Gln
        370                 375                 380
Leu Arg Val Val Ser Asp Arg Glu Glu Pro Glu Ala Ala Tyr Arg Leu
385                 390                 395                 400
Ile Gln Gly Pro Gln Tyr Gly His Leu Leu Val Gly Gly Arg Pro Thr
                    405                 410                 415
Ser Ala Phe Ser Gln Phe Gln Ile Asp Gln Gly Glu Val Val Phe Ala
                420                 425                 430
Phe Thr Asn Phe Ser Ser His Asp His Phe Arg Val Leu Ala Leu
            435                 440                 445
Ala Arg Gly Val Asn Ala Ser Ala Val Val Asn Val Thr Val Arg Ala
        450                 455                 460
```

```
Leu Leu His Val Trp Ala Gly Gly Pro Trp Pro Gln Gly Ala Thr Leu
465                 470                 475                 480

Arg Leu Asp Pro Thr Val Leu Asp Ala Gly Glu Leu Ala Asn Arg Thr
                485                 490                 495

Gly Ser Val Pro Arg Phe Arg Leu Leu Glu Gly Pro Arg His Gly Arg
                500                 505                 510

Val Val Arg Val Pro Arg Ala Arg Thr Glu Pro Gly Gly Ser Gln Leu
                515                 520                 525

Val Glu Gln Phe Thr Gln Gln Asp Leu Glu Asp Gly Arg Leu Gly Leu
530                 535                 540

Glu Val Gly Arg Pro Glu Gly Arg Ala Pro Gly Pro Ala Gly Asp Ser
545                 550                 555                 560

Leu Thr Leu Glu Leu Trp Ala Gln Gly Val Pro Pro Ala Val Ala Ser
                565                 570                 575

Leu Asp Phe Ala Thr Glu Pro Tyr Asn Ala Ala Arg Pro Tyr Ser Val
                580                 585                 590

Ala Leu Leu Ser Val Pro Glu Ala Ala Arg Thr Glu Ala Gly Lys Pro
                595                 600                 605

Glu Ser Ser Thr Pro Thr Gly Glu Pro Gly Pro Met Ala Ser Ser Pro
                610                 615                 620

Glu Pro Ala Val Ala Lys Gly Gly Phe Leu Ser Phe Leu Glu Ala Asn
625                 630                 635                 640

Met Phe Ser

<210> SEQ ID NO 10
<211> LENGTH: 11
<212> TYPE: PRT
<213> ORGANISM: Artificial Sequence
<220> FEATURE:
<223> OTHER INFORMATION: HVR-L1

<400> SEQUENCE: 10

Ser Ala Ser Gln Gly Ile Arg Asn Tyr Leu Asn
1               5                   10

<210> SEQ ID NO 11
<211> LENGTH: 7
<212> TYPE: PRT
<213> ORGANISM: Artificial Sequence
<220> FEATURE:
<223> OTHER INFORMATION: HVR-L2

<400> SEQUENCE: 11

Tyr Thr Ser Ser Leu His Ser
1               5

<210> SEQ ID NO 12
<211> LENGTH: 9
<212> TYPE: PRT
<213> ORGANISM: Artificial Sequence
<220> FEATURE:
<223> OTHER INFORMATION: HVR-L3

<400> SEQUENCE: 12

Gln Gln Tyr Ser Lys Leu Pro Trp Thr
1               5

<210> SEQ ID NO 13
<211> LENGTH: 11
<212> TYPE: PRT
```

<213> ORGANISM: Artificial Sequence
<220> FEATURE:
<223> OTHER INFORMATION: HVR-L1

<400> SEQUENCE: 13

Arg Ala Ser Gln Gly Ile Arg Asn Tyr Leu Asn
1               5                   10

<210> SEQ ID NO 14
<211> LENGTH: 11
<212> TYPE: PRT
<213> ORGANISM: Artificial Sequence
<220> FEATURE:
<223> OTHER INFORMATION: HVR-H1

<400> SEQUENCE: 14

Gly Tyr Ser Ile Thr Ser Gly Tyr Tyr Trp Asn
1               5                   10

<210> SEQ ID NO 15
<211> LENGTH: 16
<212> TYPE: PRT
<213> ORGANISM: Artificial Sequence
<220> FEATURE:
<223> OTHER INFORMATION: HVR-H2

<400> SEQUENCE: 15

Tyr Ile Thr Tyr Asp Gly Ser Asn Asn Tyr Asn Pro Ser Leu Lys Asn
1               5                   10                  15

<210> SEQ ID NO 16
<211> LENGTH: 3
<212> TYPE: PRT
<213> ORGANISM: Artificial Sequence
<220> FEATURE:
<223> OTHER INFORMATION: HVR-H3

<400> SEQUENCE: 16

Phe Asp Tyr
1

<210> SEQ ID NO 17
<211> LENGTH: 11
<212> TYPE: PRT
<213> ORGANISM: Artificial Sequence
<220> FEATURE:
<223> OTHER INFORMATION: HVR-H1

<400> SEQUENCE: 17

Gly Gly Ser Ile Thr Ser Gly Tyr Tyr Trp Asn
1               5                   10

<210> SEQ ID NO 18
<211> LENGTH: 16
<212> TYPE: PRT
<213> ORGANISM: Artificial Sequence
<220> FEATURE:
<223> OTHER INFORMATION: HVR-H2

<400> SEQUENCE: 18

Tyr Ile Thr Tyr Asp Gly Ser Asn Asn Tyr Asn Pro Ser Leu Lys Ser
1               5                   10                  15

<210> SEQ ID NO 19
<211> LENGTH: 11
<212> TYPE: PRT
<213> ORGANISM: Artificial Sequence

```
<220> FEATURE:
<223> OTHER INFORMATION: HVR-L1

<400> SEQUENCE: 19

Ser Ala Ser Gln Ser Ile Arg Asn Tyr Leu Asn
1               5                   10

<210> SEQ ID NO 20
<211> LENGTH: 11
<212> TYPE: PRT
<213> ORGANISM: Artificial Sequence
<220> FEATURE:
<223> OTHER INFORMATION: HVR-L1

<400> SEQUENCE: 20

Ser Ala Ser Gln Asp Ile Arg Asn Tyr Leu Asn
1               5                   10

<210> SEQ ID NO 21
<211> LENGTH: 11
<212> TYPE: PRT
<213> ORGANISM: Artificial Sequence
<220> FEATURE:
<223> OTHER INFORMATION: HVR-L1

<400> SEQUENCE: 21

Ser Ala Ser Gln Gly Ile Ser Asn Tyr Leu Asn
1               5                   10

<210> SEQ ID NO 22
<211> LENGTH: 7
<212> TYPE: PRT
<213> ORGANISM: Artificial Sequence
<220> FEATURE:
<223> OTHER INFORMATION: HVR-L2

<400> SEQUENCE: 22

Tyr Thr Ser Ser Leu Gln Ser
1               5

<210> SEQ ID NO 23
<211> LENGTH: 7
<212> TYPE: PRT
<213> ORGANISM: Artificial Sequence
<220> FEATURE:
<223> OTHER INFORMATION: HVR-L2

<400> SEQUENCE: 23

Asp Ala Ser Ser Leu His Ser
1               5

<210> SEQ ID NO 24
<211> LENGTH: 7
<212> TYPE: PRT
<213> ORGANISM: Artificial Sequence
<220> FEATURE:
<223> OTHER INFORMATION: HVR-L2

<400> SEQUENCE: 24

Tyr Thr Ser Asn Leu Glu Thr
1               5

<210> SEQ ID NO 25
<211> LENGTH: 6
<212> TYPE: PRT
<213> ORGANISM: Artificial Sequence
<220> FEATURE:
```

<223> OTHER INFORMATION: HVR-H1

<400> SEQUENCE: 25

Ser Gly Tyr Tyr Trp Ser
1               5

<210> SEQ ID NO 26
<211> LENGTH: 107
<212> TYPE: PRT
<213> ORGANISM: Artificial Sequence
<220> FEATURE:
<223> OTHER INFORMATION: LC007 Chimeric Antibody VL

<400> SEQUENCE: 26

Asp Ile Val Leu Thr Gln Ser Pro Ser Ser Leu Ser Ala Ser Leu Gly
1               5                   10                  15

Asp Arg Val Thr Ile Ser Cys Ser Ala Ser Gln Gly Ile Arg Asn Tyr
            20                  25                  30

Leu Asn Trp Tyr Gln Gln Arg Pro Asp Gly Thr Val Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Lys Leu Pro Trp
                85                  90                  95

Thr Phe Gly Gly Gly Thr Lys Leu Glu Ile Lys
            100                 105

<210> SEQ ID NO 27
<211> LENGTH: 112
<212> TYPE: PRT
<213> ORGANISM: Artificial Sequence
<220> FEATURE:
<223> OTHER INFORMATION: LC007 Chimeric Antibody VH

<400> SEQUENCE: 27

Glu Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
            20                  25                  30

Tyr Tyr Trp Asn Trp Ile Arg Gln Phe Pro Gly Asn Lys Leu Glu Trp
        35                  40                  45

Met Gly Tyr Ile Thr Tyr Asp Gly Ser Asn Asn Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Asp Phe Asp Tyr Trp Gly Gln Gly Thr Thr Leu Thr Val Ser Ser
            100                 105                 110

<210> SEQ ID NO 28
<211> LENGTH: 107
<212> TYPE: PRT
<213> ORGANISM: Artificial Sequence
<220> FEATURE:
<223> OTHER INFORMATION: LC007 Humanized Antibody ML1 VL

<400> SEQUENCE: 28

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Gly Ile Arg Asn Tyr
            20                  25                  30

Leu Asn Trp Tyr Gln Gln Lys Pro Gly Lys Ala Pro Lys Leu Leu Ile
            35                  40                  45

Tyr Tyr Thr Ser Ser Leu His Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Lys Leu Pro Trp
                85                  90                  95

Thr Phe Gly Gln Gly Thr Lys Val Glu Ile Lys
                100                 105
```

<210> SEQ ID NO 29
<211> LENGTH: 112
<212> TYPE: PRT
<213> ORGANISM: Artificial Sequence
<220> FEATURE:
<223> OTHER INFORMATION: LC007 Humanized Antibody M4-1 VH

<400> SEQUENCE: 29

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Gly
            20                  25                  30

Tyr Tyr Trp Asn Trp Ile Arg Gln His Pro Gly Lys Gly Leu Glu Trp
            35                  40                  45

Ile Gly Tyr Ile Thr Tyr Asp Gly Ser Asn Asn Tyr Asn Pro Ser Leu
        50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Asp Phe Asp Tyr Trp Gly Gln Gly Thr Leu Val Thr Val Ser Ser
                100                 105                 110
```

<210> SEQ ID NO 30
<211> LENGTH: 112
<212> TYPE: PRT
<213> ORGANISM: Artificial Sequence
<220> FEATURE:
<223> OTHER INFORMATION: LC007 Humanized Antibody M4-2 VH

<400> SEQUENCE: 30

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Gly
            20                  25                  30

Tyr Tyr Trp Asn Trp Ile Arg Gln His Pro Gly Lys Gly Leu Glu Trp
            35                  40                  45

Ile Gly Tyr Ile Thr Tyr Asp Gly Ser Asn Asn Tyr Asn Pro Ser Leu
        50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95
```

Ala Arg Phe Asp Tyr Trp Gly Gln Gly Thr Leu Val Thr Val Ser Ser
            100                 105                 110

<210> SEQ ID NO 31
<211> LENGTH: 107
<212> TYPE: PRT
<213> ORGANISM: Artificial Sequence
<220> FEATURE:
<223> OTHER INFORMATION: LC007 Humanized Antibody ML2 VL

<400> SEQUENCE: 31

Asp Ile Gln Met Thr Gln Ser Pro Ser Leu Ser Ala Ser Val Gly
1               5                   10                  15

Asp Arg Val Thr Ile Thr Cys Arg Ala Ser Gln Gly Ile Arg Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Ser Leu His Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Lys Leu Pro Trp
                85                  90                  95

Thr Phe Gly Gln Gly Thr Lys Val Glu Ile Lys
            100                 105

<210> SEQ ID NO 32
<211> LENGTH: 112
<212> TYPE: PRT
<213> ORGANISM: Artificial Sequence
<220> FEATURE:
<223> OTHER INFORMATION: LC007 Humanized Antibody M4-3 VH

<400> SEQUENCE: 32

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Gly
                20                  25                  30

Tyr Tyr Trp Asn Trp Ile Arg Gln His Pro Gly Lys Gly Leu Glu Trp
            35                  40                  45

Ile Gly Tyr Ile Thr Tyr Asp Gly Ser Asn Asn Tyr Asn Pro Ser Leu
        50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Asp Phe Asp Tyr Trp Gly Gln Gly Thr Leu Val Thr Val Ser Ser
            100                 105                 110

<210> SEQ ID NO 33
<211> LENGTH: 112
<212> TYPE: PRT
<213> ORGANISM: Artificial Sequence
<220> FEATURE:
<223> OTHER INFORMATION: LC007 Humanized Antibody M4-6 VH

<400> SEQUENCE: 33

Gln Val Gln Leu Gln Glu Ser Gly Pro Gly Leu Val Lys Pro Ser Gln
1               5                   10                  15

```
Thr Leu Ser Leu Thr Cys Thr Val Ser Gly Tyr Ser Ile Thr Ser Gly
            20                  25                  30

Tyr Tyr Trp Asn Trp Ile Arg Gln His Pro Gly Lys Gly Leu Glu Trp
        35                  40                  45

Ile Gly Tyr Ile Thr Tyr Asp Gly Ser Asn Asn Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Asp Phe Asp Tyr Trp Gly Gln Gly Thr Leu Val Thr Val Ser Ser
            100                 105                 110

<210> SEQ ID NO 34
<211> LENGTH: 214
<212> TYPE: PRT
<213> ORGANISM: Artificial Sequence
<220> FEATURE:
<223> OTHER INFORMATION: LC007  Chimeric Antibody Light Chain

<400> SEQUENCE: 34

Asp Ile Val Leu Thr Gln Ser Pro Ser Ser Leu Ser Ala Ser Leu Gly
1               5                   10                  15

Asp Arg Val Thr Ile Ser Cys Ser Ala Ser Gln Gly Ile Arg Asn Tyr
            20                  25                  30

Leu Asn Trp Tyr Gln Gln Arg Pro Asp Gly Thr Val Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Lys Leu Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 35
<211> LENGTH: 442
<212> TYPE: PRT
<213> ORGANISM: Artificial Sequence
<220> FEATURE:
<223> OTHER INFORMATION: LC007  Chimeric Antibody Heavy Chain

<400> SEQUENCE: 35
```

-continued

```
Glu Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
            20                  25                  30

Tyr Tyr Trp Asn Trp Ile Arg Gln Phe Pro Gly Asn Lys Leu Glu Trp
                35                  40                  45

Met Gly Tyr Ile Thr Tyr Asp Gly Ser Asn Asn Tyr Asn Pro Ser Leu
50                  55                  60

Lys Asn Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Asp Phe Asp Tyr Trp Gly Gln Gly Thr Thr Leu Thr Val Ser Ser
                100                 105                 110

Ala Ser Thr Lys Gly Pro Ser Val Phe Pro Leu Ala Pro Ser Ser Lys
            115                 120                 125

Ser Thr Ser Gly Gly Thr Ala Ala Leu Gly Cys Leu Val Lys Asp Tyr
            130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
                180                 185                 190

Tyr Ile Cys Asn Val Asn His Lys Pro Ser Asn Thr Lys Val Asp Lys
            195                 200                 205

Lys Val Glu Pro Lys Ser Cys Asp Lys Thr His Thr Cys Pro Pro Cys
210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
                260                 265                 270

Tyr Val Asp Gly Val Glu Val His Asn Ala Lys Thr Lys Pro Arg Glu
            275                 280                 285

Glu Gln Tyr Asn Ser Thr Tyr Arg Val Val Ser Val Leu Thr Val Leu
            290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Asp Glu
            340                 345                 350

Leu Thr Lys Asn Gln Val Ser Leu Thr Cys Leu Val Lys Gly Phe Tyr
            355                 360                 365

Pro Ser Asp Ile Ala Val Glu Trp Glu Ser Asn Gly Gln Pro Glu Asn
            370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415
```

Val Phe Ser Cys Ser Val Met His Glu Ala Leu His Asn His Tyr Thr
            420                 425                 430

Gln Lys Ser Leu Ser Leu Ser Pro Gly Lys
        435                 440

<210> SEQ ID NO 36
<211> LENGTH: 214
<212> TYPE: PRT
<213> ORGANISM: Artificial Sequence
<220> FEATURE:
<223> OTHER INFORMATION: LC007 Humanized Antibody ML2 Light Chain

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Lys Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 37
<211> LENGTH: 442
<212> TYPE: PRT
<213> ORGANISM: Artificial Sequence
<220> FEATURE:
<223> OTHER INFORMATION: LC007 Humanized Antibody M4-3 Heavy Chain

<400> SEQUENCE: 37

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Gly
            20                  25                  30

Tyr Tyr Trp Asn Trp Ile Arg Gln His Pro Gly Lys Gly Leu Glu Trp
        35                  40                  45

Ile Gly Tyr Ile Thr Tyr Asp Gly Ser Asn Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Asp Phe Asp Tyr Trp Gly Gln Gly Thr Leu Val Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Val Glu Pro Lys Ser Cys Asp Lys Thr His Thr Cys Pro Pro Cys
    210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Asp Glu
            340                 345                 350

Leu Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
        435                 440

<210> SEQ ID NO 38
<211> LENGTH: 324
<212> TYPE: DNA
<213> ORGANISM: Artificial Sequence
<220> FEATURE:

<223> OTHER INFORMATION: LC007 Murine Antibody Light Chain

<400> SEQUENCE: 38

```
gatattgtgc tcacacagtc tccatcctcc ctgtctgcct ctctgggaga cagagtcacc    60
atcagttgca gtgcaagtca gggcattaga aattatttaa actggtatca gcagagacca   120
gatggaactg ttaaactcct gatctattac acatcaagtt tacactcagg agtcccatca   180
aggttcagtg gcagtgggtc tgggacagat tattctctca ccatcagcaa cctggaacct   240
gaagatattg ccacttacta ttgtcagcag tatagtaagc ttccttggac gttcggtgga   300
ggcaccaagc tggaaatcaa acgg                                          324
```

<210> SEQ ID NO 39
<211> LENGTH: 339
<212> TYPE: DNA
<213> ORGANISM: Artificial Sequence
<220> FEATURE:
<223> OTHER INFORMATION: LC007 Murine Antibody Heavy Chain

<400> SEQUENCE: 39

```
gaggtccagc tgcaggagtc aggacctggc ctcgtgaaac cttctcagtc tctgtctctc    60
acctgctctg tcactggcta ctccatcacc agtggttatt actggaactg gatccggcag   120
tttccaggaa acaagctgga atggatgggc tacataacct acgacggtag caataactac   180
aacccatctc tcaaaaatcg aatctccatc actcgtgaca catctaagaa ccagtttttc   240
ctgaagttga attctgtgac tactgaggac acagctacat attactgtgc ggactttgac   300
tactggggcc aaggcaccac tctcacagtc tcctcagcc                          339
```

<210> SEQ ID NO 40
<211> LENGTH: 645
<212> TYPE: DNA
<213> ORGANISM: Artificial Sequence
<220> FEATURE:
<223> OTHER INFORMATION: LC007 Chimeric Antibody Light Chain

<400> SEQUENCE: 40

```
gatattgtgc tcacacagtc tccatcctcc ctgtctgcct ctctgggaga cagagtcacc    60
atcagttgca gtgcaagtca gggcattaga aattatttaa actggtatca gcagagacca   120
gatggaactg ttaaactcct gatctattac acatcaagtt tacactcagg agtcccatca   180
aggttcagtg gcagtgggtc tgggacagat tattctctca ccatcagcaa cctggaacct   240
gaagatattg ccacttacta ttgtcagcag tatagtaagc ttccttggac gttcggtgga   300
ggcaccaagc tggaaatcaa acgtacggtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga aaacacaaa gtctacgcct gcgaagtcac ccatcagggc   600
ctgagctcgc ccgtcacaaa gagcttcaac aggggagagt gttag                   645
```

<210> SEQ ID NO 41
<211> LENGTH: 1329
<212> TYPE: DNA
<213> ORGANISM: Artificial Sequence
<220> FEATURE:
<223> OTHER INFORMATION: LC007 Chimeric Antibody Heavy Chain

<400> SEQUENCE: 41

```
gaggtccagc tgcaggagtc aggacctggc ctcgtgaaac cttctcagtc tctgtctctc      60
acctgctctg tcactggcta ctccatcacc agtggttatt actggaactg gatccggcag     120
tttccaggaa acaagctgga atggatgggc tacataacct cgacggtag caataactac      180 aacccatctc tcaaaaatcg aatctccatc actcgtgaca catctaagaa ccagttttc      240 ctgaagttga attctgtgac tactgaggac acagctacat attactgtgc ggactttgac     300
tactggggcc aaggcaccac tctcacagtc tcctcagcta gcaccaaggg cccatcggtc     360
ttccccctgg cacctcctc aagagcacc tctgggggca gcggccct gggctgcctg         420 gtcaaggact acttccccga accggtgacg gtgtcgtgga actcaggcgc cctgaccagc     480
ggcgtgcaca ccttcccggc tgtcctacag tcctcaggac tctactccct cagcagcgtg     540
gtgaccgtgc cctccagcag cttgggcacc cagacctaca tctgcaacgt gaatcacaag     600
cccagcaaca ccaaggtgga caagaaagtt gagcccaaat cttgtgacaa aactcacaca     660
tgcccaccgt gcccagcacc tgaactcctg gggggaccgt cagtcttcct cttccccca      720 aaacccaagg acaccctcat gatctcccgg acccctgagg tcacatgcgt ggtggtggac     780
gtgagccacg aagaccctga ggtcaagttc aactggtacg tggacggcgt ggaggtgcat     840
aatgccaaga caaagccgcg ggaggagcag tacaacagca cgtaccgtgt ggtcagcgtc     900
ctcaccgtcc tgcaccagga ctggctgaat ggcaaggagt acaagtgcaa ggtctccaac     960
aaagccctcc cagcccccat cgagaaaacc atctccaaag ccaaagggca gccccgagaa    1020
ccacaggtgt acaccctgcc cccatcccgg gatgagctga ccaagaacca ggtcagcctg    1080
acctgcctgg tcaaaggctt ctatcccagc gacatcgccg tggagtggga gagcaatggg    1140
cagccggaga acaactacaa gaccacgcct cccgtgctgg actccgacgg ctccttcttc    1200
ctctacagca agctcaccgt ggacaagagc aggtggcagc aggggaacgt cttctcatgc    1260
tccgtgatgc atgaggctct gcacaaccac tacacgcaga agagcctctc cctgtctccg    1320
ggtaaatga                                                             1329
```

<210> SEQ ID NO 42
<211> LENGTH: 321
<212> TYPE: DNA
<213> ORGANISM: Artificial Sequence
<220> FEATURE:
<223> OTHER INFORMATION: LC007 Humanized Antibody ML2 Light Chain

<400> SEQUENCE: 42

```
gacatccaga tgacccagag ccccagcagc ctgagcgcca gcgtgggcga cagagtgacc      60
atcacctgcc gggccagcca gggcatccgg aactacctga actggtatca gcagaagccc     120
ggcaaggccc ccaagctgct gatctactac accagcagcc tgcacagcgg cgtgcctagc     180
cggtttagcg gcagcggctc cggcaccgac ttcaccctga ccattagctc cctgcagccc     240
gaggacttcg ccacctacta ctgccagcag tacagcaagc tgccctggac cttcggccag     300
ggaacaaagg tggagatcaa g                                               321
```

<210> SEQ ID NO 43
<211> LENGTH: 336
<212> TYPE: DNA
<213> ORGANISM: Artificial Sequence
<220> FEATURE:
<223> OTHER INFORMATION: LC007 Humanized Antibody M4-3 Heavy Chain

<400> SEQUENCE: 43

-continued

```
caggtgcagc tgcaggaaag cggccctggc ctggtcaagc ccagccagac cctgagcctg       60
acctgcaccg tgtccggcgg cagcatcacc agcggctact actggaactg gatccggcag      120 cacccggca  agggcctgga atggatcggc tacatcacct acgacggcag caacaactac      180
aaccccagcc tgaagtccag agtgaccatc agccgggaca ccagcaagaa ccagttcagc      240
ctgaagctgt ccagcgtgac agccgccgac accgccgtgt actactgcgc cgacttcgac      300
tactggggcc agggcaccct ggtcaccgtg tccagc                                336
```

<210> SEQ ID NO 44
<211> LENGTH: 21
<212> TYPE: PRT
<213> ORGANISM: Homo sapiens

<400> SEQUENCE: 44

Val Ile Ile Pro Met Cys Leu Val Leu Leu Leu Ala Leu Ile Leu
1               5                   10                  15

Pro Leu Leu Phe Tyr
            20

ANTI-MCSP ANTIBODIES

CROSS REFERENCE TO RELATED APPLICATIONS

This application claims priority to European Patent Application No. EP 11178393.2, filed on Aug. 23, 2011, the disclosure of which is incorporated herein by reference in its entirety.

SEQUENCE LISTING

The present application contains a Sequence Listing which has been submitted in ASCII format via EFS-Web and is hereby incorporated by reference in its entirety. Said ASCII copy, created on Aug. 10, 2012, is named P4932US_ST25.txt and is 75,162 bytes in size.

FIELD OF THE INVENTION

The present invention relates to anti-MCSP antibodies and methods of using the same in the treatment and diagnosis of diseases.

BACKGROUND

MCSP

Melanoma chondroitin sulfate proteoglycan (MCSP) is a large transmembrane proteoglycan that is expressed in the majority of melanoma cancers. MCSP is also expressed on other cancers, including glioblastomas, osteosarcomsa, chondrosarcomas, some types of ALL and AML, and in basel cell carcinomas. It serves as an early cell surface melanoma progression marker and is involved in stimulating tumor cell proliferation, metastasis, migration, invasion, and angiogenesis. Staube, E. et al., FEBS Letters, 527: 114-118 (2002); Campoli, M. et al., Crit. Rev. Immun. 24:267-296 (2004); Vergilis, I. J., J Invest Dermatol, 125: 526-531 (2005); Yang, J., JCB, 165: 881-891 (2004); Luo, W., J. Immuno, 176: 6046-6054 (2006).

Antibody Glycosylation

The oligosaccharide component can significantly affect properties relevant to the efficacy of a therapeutic glycoprotein, including physical stability, resistance to protease attack, interactions with the immune system, pharmacokinetics, and specific biological activity. Such properties may depend not only on the presence or absence, but also on the specific structures, of oligosaccharides. Some generalizations between oligosaccharide structure and glycoprotein function can be made. For example, certain oligosaccharide structures mediate rapid clearance of the glycoprotein from the bloodstream through interactions with specific carbohydrate binding proteins, while others can be bound by antibodies and trigger undesired immune reactions (Jenkins et al., Nat Biotechnol 14, 975-81 (1996)).

IgG1 type antibodies, the most commonly used antibodies in cancer immunotherapy, are glycoproteins that have a conserved N-linked glycosylation site at Asn 297 in each CH2 domain. The two complex biantennary oligosaccharides attached to Asn 297 are buried between the CH2 domains, forming extensive contacts with the polypeptide backbone, and their presence is essential for the antibody to mediate effector functions such as antibody dependent cell-mediated cytotoxicity (ADCC) (Lifely et al., Glycobiology 5, 813-822 (1995); Jefferis et al., Immunol Rev 163, 59-76 (1998); Wright and Morrison, Trends Biotechnol 15, 26-32 (1997)).

Cell-mediated effector functions of monoclonal antibodies can be enhanced by engineering their oligosaccharide component as described in Umana et al., Nat Biotechnol 17, 176-180 (1999) and U.S. Pat. No. 6,602,684 (WO 99/54342). Umana et al. showed that overexpression of .beta.(1,4)-N-acetylglucosaminyltransferase III (GnTIII), a glycosyltransferase catalyzing the formation of bisected oligosaccharides, in Chinese hamster ovary (CHO) cells significantly increases the in vitro ADCC activity of antibodies produced in those cells. Alterations in the composition of the Asn 297 carbohydrate or its elimination also affect binding of the antibody Fc-domain to Fc.gamma.R and C1q protein (Umana et al., Nat Biotechnol 17, 176-180 (1999); Davies et al., Biotechnol Bioeng 74, 288-294 (2001); Mimura et al., J Biol Chem 276, 45539-45547 (2001); Radaev et al., J Biol Chem 276, 16478-16483 (2001); Shields et al., J Biol Chem 276, 6591-6604 (2001); Shields et al., J Biol Chem 277, 26733-26740 (2002); Simmons et al., J Immunol Methods 263, 133-147 (2002)).

SUMMARY

The invention provides anti-MCSP antibodies and methods of using the same. One aspect of the invention provides for an isolated antibody that binds to a membrane proximal epitope of human MCSP wherein the antibody has been glycoengineered to modify the oligosaccharides in the Fc region and wherein the antibody has increased ADCC effector function as compared to an non-glycoengineered antibody. In one embodiment, the membrane proximal epitope of human MCSP comprises comprising a CSPG repeat-containing domain. In one embodiment, the CSPG repeat-containing domain comprises CSPG repeat 14 (SEQ ID NO: 3). In one embodiment, the Fc region of the antibody has a reduced number of fucose residues as compared to the nonglycoengineered antibody. In one embodiment, the antibody has an increased ratio of GlcNAc residues to fucose residues in the Fc region compared to the non-glycoengineered antibody. In one embodiment, the Fc region of the antibody has an increased proportion of bisected oligosaccharides as compared to the non-glycoengineered antibody. In certain embodiments, the antibody is a monoclonal antibody. In certain embodiments, the antibody is a human, humanized, or chimeric antibody. In certain embodiments, the antibody is a full-length IgG class antibody.

In one embodiment, the anti-MCSP antibody comprises an HVR-H1 comprising the amino acid sequence of SEQ ID NO: 14, an HVR-H2 comprising the amino acid sequence of SEQ ID NO: 15, and an HVR-H3 comprising the amino acid sequence of SEQ ID NO: 16. In one embodiment, the anti-MCSP antibody comprises an HVR-L1 comprising the amino acid sequence of SEQ ID NO: 10; an HVR-L2 comprising the amino acid sequence of SEQ ID NO: 11; and an HVR-L3 comprising the amino acid sequence of SEQ ID NO: 12. In one embodiment, the anti-MCSP antibody comprises an HVR-H1 comprising the amino acid sequence of SEQ ID NO: 14; an HVR-H2 comprising the amino acid sequence of SEQ ID NO: 15; an HVR-H3 comprising the amino acid sequence of SEQ ID NO: 16; an HVR-L1 comprising the amino acid sequence of SEQ ID NO: 10; an HVR-L2 comprising the amino acid sequence of SEQ ID NO: 11; and an HVR-L3 comprising the amino acid sequence of SEQ ID NO: 12.

In one embodiment, the anti-MCSP antibody comprises an HVR-H1 comprising the amino acid sequence of SEQ ID NO: 17, an HVR-H2 comprising the amino acid sequence of SEQ ID NO: 18, and an HVR-H3 comprising the amino acid sequence of SEQ ID NO: 16. In one embodiment, the anti- MCSP antibody comprises an HVR-L1 comprising the amino acid sequence of SEQ ID NO: 13; an HVR-L2 comprising the amino acid sequence of SEQ ID NO: 11; and an HVR-L3 comprising the amino acid sequence of SEQ ID NO: 12. In one embodiment, the anti-MCSP antibody comprises an HVR-H1 comprising the amino acid sequence of SEQ ID NO: 17; an HVR-H2 comprising the amino acid sequence of SEQ ID NO: 18; an HVR-H3 comprising the amino acid sequence of SEQ ID NO: 16; an HVR-L1 comprising the amino acid sequence of SEQ ID NO: 13; an HVR-L2 comprising the amino acid sequence of SEQ ID NO: 11; and an HVR-L3 comprising the amino acid sequence of SEQ ID NO: 12.

In one embodiment, the anti-MCSP antibody comprises a VH sequence having at least 95% sequence identity to the amino acid sequence of SEQ ID NO: 29; a VL sequence having at least 95% sequence identity to the amino acid sequence of SEQ ID NO: 28; or a VH sequence having at least 95% sequence identity to the amino acid sequence of SEQ ID NO: 29 and a VL sequence having at least 95% sequence identity to the amino acid sequence of SEQ ID NO: 28

In one embodiment, the anti-MCSP antibody comprises a VH sequence of SEQ ID NO: 29; a VL sequence of SEQ ID NO: 28. In one embodiment, the anti-MCSP antibody comprises a VH sequence of SEQ ID NO: 29 and a VL sequence of SEQ ID NO: 28

In one embodiment, the anti-MCSP antibody comprises a VH sequence having at least 95% sequence identity to the amino acid sequence of SEQ ID NO: 32; a VL sequence having at least 95% sequence identity to the amino acid sequence of SEQ ID NO: 31; or a VH sequence having at least 95% sequence identity to the amino acid sequence of SEQ ID NO: 32 and a VL sequence having at least 95% sequence identity to the amino acid sequence of SEQ ID NO: 32

In one embodiment, the anti-MCSP antibody comprises a VH sequence of SEQ ID NO: 29; a VL sequence of SEQ ID NO: 28. In one embodiment, the anti-MCSP antibody comprises a VH sequence of SEQ ID NO: 29 and a VL sequence of SEQ ID NO: 28

Another aspect of the invention provides for an isolated nucleic acid encoding an anti-MCSP antibody as described above. Another aspect of the invention provides for a host cell comprising such a nucleic acid. Another aspect of the invention provides for a method of producing an antibody comprising culturing such a host cell so that the antibody is produced.

Another aspect of the invention provides for an immunoconjugate comprising an anti-MCSP antibody as described above and a cytotoxic agent. Another aspect of the invention provides for an immunoconjugate comprising an anti-MCSP antibody as described above and a pharmaceutically acceptable carrier.

Another aspect of the invention provides for an immunoconjugate comprising an anti-MCSP antibody as described above for use as a medicament. Another aspect of the invention provides for an anti-MCSP antibody as described above or an immunoconjugate thereof for treating a cancer, in particular those cancers that express MCSP, including skin cancer (including melanoma and basel cell carcinomas), gliomas (including glioblastomas), bone cancer (such as osteosarcomas), and leukemia (including ALL and AML).

Another aspect of the invention provides for use of an anti-MCSP antibody as described above for inducing cell lysis. Another aspect of the invention provides for use of an anti-MCSP antibody as described above or immunoconjugate thereof in the manufacture of a medicament, such as a medicament for treatment of cancer, or for inducing cell lysis.

Another aspect of the invention provides for a method of treating an individual having cancer comprising administering to the individual an effective amount of an anti-MCSP antibody as described above or immunoconjugate thereof. The cancer is, for example, a cancer that expresses MCSP, such as skin cancer (including melanoma and basel cell carcinomas), gliomas (including glioblastomas), bone cancer (such as osteosarcomas), and leukemia (including ALL and AML).

Another aspect of the invention provides for a method of inducing cell lysis in an individual comprising administering to the individual an effective amount of an anti-MCSP antibody as described above or immunoconjugate thereof to induce cell lysis.

Another aspect of the invention provides for MCSP immunohistochemical assay comprising contacting a sample with an anti-MCSP antibody as described above under conditions permissive for formation of an antibody-MCSP complex between the antibody and MCSP present in the sample and detecting the presence or absence of the complex by an immunodetection method. In one embodiment, the sample is fresh tissue sample. In one embodiment, the sample is a frozen or formalin-fixed, paraffin-embedded tissue (FFPET).

DETAILED DESCRIPTION OF EMBODIMENTS OF THE INVENTION

I. Definitions

Figure 1:
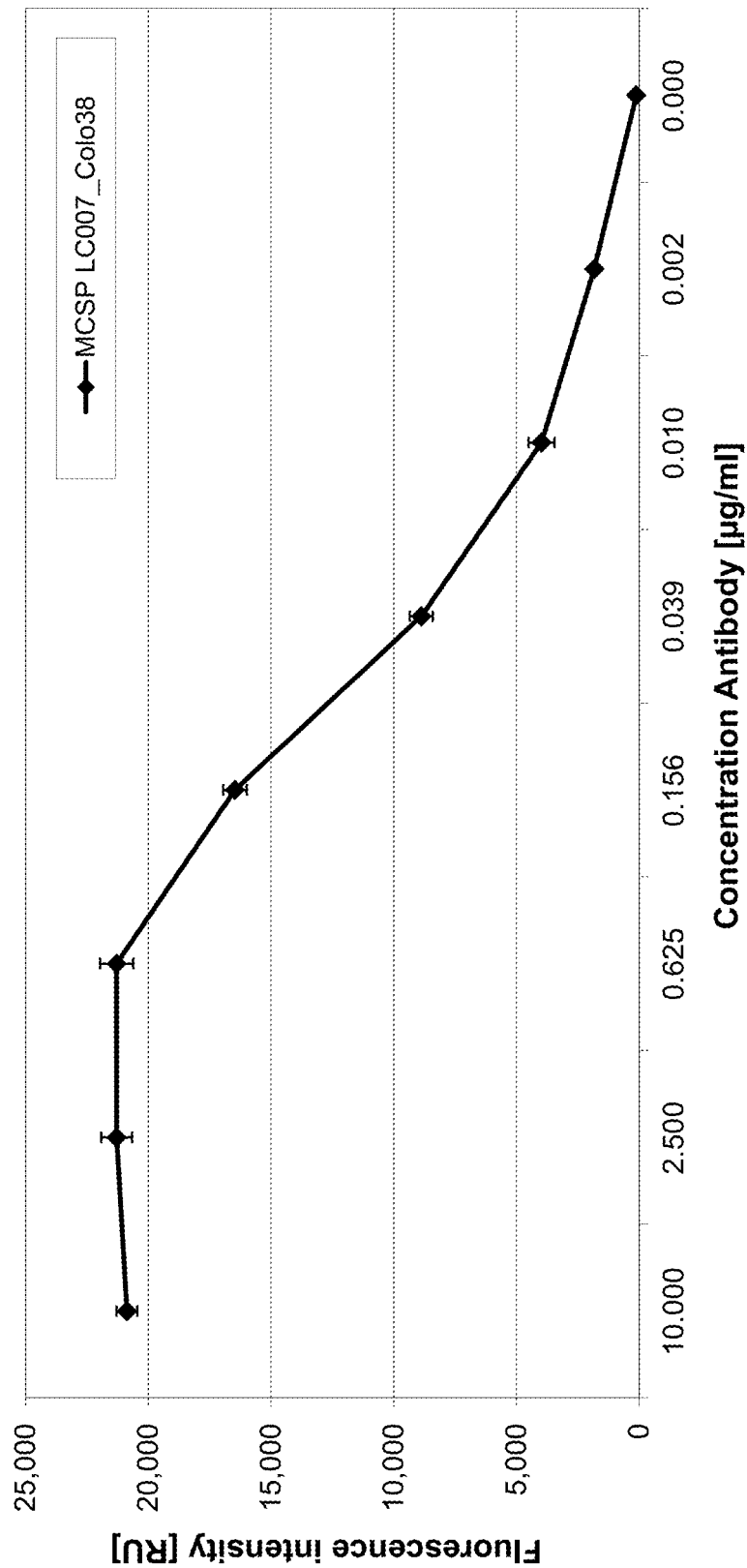
FIG. 1 is a graph depicting the results of a FACs assay showing binding affinity of chimeric antibody LC007 for surface MCSP in Colo38 cells.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen An "angiogenic disorder" refers to any dysregulation of angiogenesis, including both non-neoplastic and neoplastic conditions. Neoplastic conditions include but are not limited those described below. Non-neoplastic disorders include but are not limited to undesired or aberrant hypertrophy, arthritis, rheumatoid arthritis (RA), psoriasis, psoriatic plaques, sarcoidosis, atherosclerosis, atherosclerotic plaques, diabetic and other proliferative retinopathies including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, chronic inflammation, lung inflammation, acute lung injury/ARDS, sepsis, primary pulmonary hypertension, malignant pulmonary effusions, cerebral edema (e.g., associated with acute stroke/closed head injury/trauma), synovial inflammation, pannus formation in RA, myositis ossificans, hypertropic bone formation, osteoarthritis (OA), refractory ascites, polycystic ovarian disease, endometriosis, 3rd spacing of fluid diseases (pancreatitis, compartment syndrome, burns, bowel disease), uterine fibroids, premature labor, chronic inflammation such as IBD (Crohn's disease and ulcerative colitis), renal allograft rejection, inflammatory bowel disease, nephrotic syndrome, undesired or aberrant tissue mass growth (non-cancer), hemophilic joints, hypertrophic scars, inhibition of hair growth, Osler-Weber syndrome, pyogenic granuloma retrolental fibroplasias, scleroderma, trachoma, vascular adhesions, synovitis, dermatitis, preeclampsia, ascites, pericardial effusion (such as that associated with pericarditis), and pleural effusion.

The terms "anti-MCSP antibody" and "an antibody that binds to MCSP" refer to an antibody that is capable of binding MCSP with sufficient affinity such that the antibody is useful as a diagnostic and/or therapeutic agent in targeting MCSP. In one embodiment, the extent of binding of an anti-MCSP antibody to an unrelated, non-MCSP protein is less than about 10% of the binding of the antibody to MCSP as measured, e.g., by a radioimmunoassay (RIA). In certain embodiments, an antibody that binds to MCSP has a dissociation constant (Kd) of ≤1 µM, ≤100 nM, ≤10 nM, ≤1 nM, ≤0.1 nM, ≤0.01 nM, or ≤0.001 nM (e.g. $10^{-8}$M or less, e.g. from $10^{-8}$M to $10^{-13}$M, e.g., from $10^{-9}$M to $10^{-13}$ M). In certain embodiments, an anti-MCSP antibody binds to an epitope of MCSP that is conserved among MCSP from different species.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The terms "cancer" and "cancerous" refer to or describe the physiological condition in mammals that is typically characterized by unregulated cell growth/proliferation. Examples of cancer include, but are not limited to, carcinoma, lymphoma (e.g., Hodgkin's and non-Hodgkin's lymphoma), blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, cancer of the bone (e.g. osteosarcomas, chondrosarcoma, Ewing's sarcoma), gastrointestinal cancer, pancreatic cancer, glioma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, skin cancer (e.g. melanoma and basel cell carcinoma), vulval cancer, thyroid cancer, hepatic carcinoma, leukemia and other lymphoproliferative disorders, and various types of head and neck cancer.

The terms "cell proliferative disorder" and "proliferative disorder" refer to disorders that are associated with some degree of abnormal cell proliferation. In one embodiment, the cell proliferative disorder is cancer.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences of Proteins of Immunological Interest*, 5th Ed. Public Health Service, National Institutes of Health, Bethesda, Md. (1991).) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-MCSP antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa ($\kappa$) and lambda ($\lambda$), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "MCSP," as used herein, refers to any native MCSP (Melanoma Chondroitin Sulfate Proteoglycan) from any vertebrate source, including mammals such as primates (e.g. humans) and rodents (e.g., mice and rats), unless otherwise indicated. The term encompasses "full-length," unprocessed MCSP as well as any form of MCSP that results from processing in the cell. The term also encompasses naturally occurring variants of MCSP, e.g., splice variants or allelic variants. MCSP is also known as chondroitin sulfate proteoglycan 4 (CSPG4), chondroitin sulfate proteoglycan NG2, high molecular weight-melanoma associated antigen (HMW-MAA), and melanoma chondroitin sulfate proteoglycan. The amino acid sequence of an exemplary human MCSP is shown in SEQ ID NO: 1. See also Pluschke G., et al., Molecular cloning of a human melanoma-associated chondroitin sulfate proteoglycan, Proc. Natl. Acad. Sci. U.S.A. 93:9710-9715 (1996), Staub E., et al., A novel repeat in the melanoma-associated chondroitin sulfate proteoglycan defines a new protein family, FEBS Lett. 527:114-118 (2002); Genbank AccessionNo: NP_001888.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6th ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

II. Compositions and Methods

The invention provides anti-MCSP antibodies that find use in treating and/or diagnosing cell proliferative diseases, such as cancer. In certain embodiments, antibodies that bind to the membrane proximal epitope of MCSP are provided. In certain embodiments, antibodies with enhanced effector function that bind to MCSP are provided.

A. Exemplary Anti-MCSP Antibodies

Figure 3:
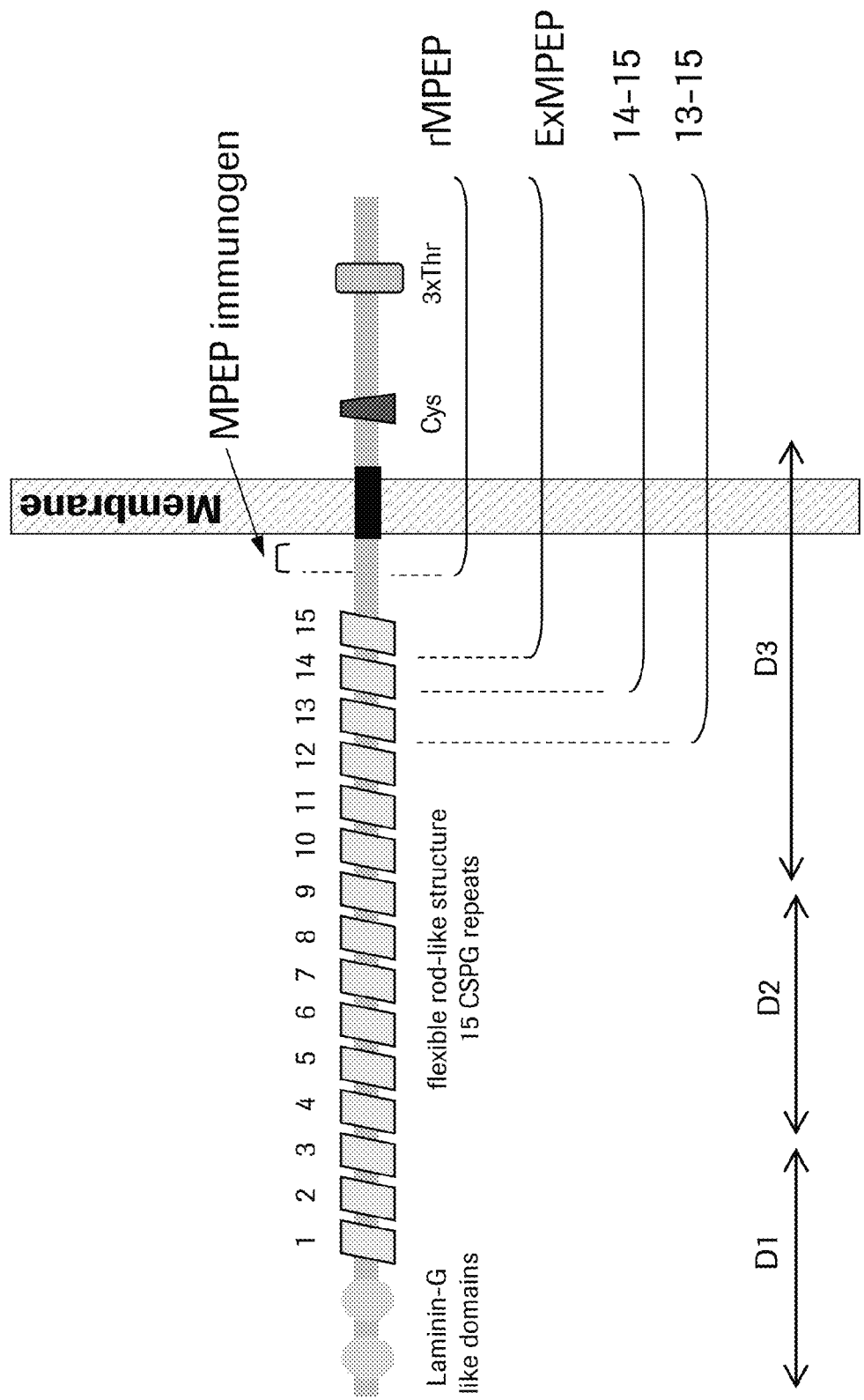
FIG. 3 is a schematic of the CSPG repeat containing structure of MCSP.

In one aspect, the invention provides isolated antibodies that bind to MCSP. In particular, the anti-MCSP antibodies provided for in the invention bind to a membrane proximal epitope of human MCSP. As discussed in Staub E., et al., FEBS Lett. 527:114-118 (2002), the membrane proximal region of MCSP is comprised of multiple novel repeated domains, referred to as CSPG repeat domains. FIG. 3. The anti-MCSP antibodies of the invention bind to an epitope present in the membrane proximal domain of human MCSP comprising a CSPG repeat-containing domain. In one embodiment, the CSPG repeat-containing domain comprises CSPG repeat 14, which corresponds to amino acids amino acids 1937-2043 of human MCSP. In one embodiment, the CSPG repeat 14 domain has the amino acid sequence shown in SEQ ID NO: 3. In another embodiment, the CSPG repeat-containing domain comprises CSPG repeat 14 and at least a portion of CSPG repeat 15. The CSPG repeat 15 domain corresponds to amino acids 2044-2246 of human MCSP. In one embodiment, the CSPG repeat-15 domain has the amino acid sequence of SEQ ID NO: 4. In one embodiment, the CSPG repeat-containing domain comprises the amino acid sequence of SEQ ID NO: 5. In one embodiment, the CSPG repeat-containing domain comprises the amino acid sequence of SEQ ID NO: 5 without the native transmembrane domain. In one embodiment, the CSPG repeat-containing domain comprises CSPG repeat 13-15. In one embodiment, the CSPG repeat-containing domain comprises the amino acid sequence of SEQ ID NO: 6. In one embodiment, the CSPG repeat-containing domain comprises the amino acid sequence of SEQ ID NO: 6 without the native transmembrane domain. In one embodiment, the CSPG repeat-containing domain comprises CSPG repeat 12-15. In one embodiment, the CSPG repeat-containing domain comprises the amino acid sequence of SEQ ID NO: 7. In one embodiment, the CSPG repeat-containing domain comprises the amino acid sequence of SEQ ID NO: 7 without the native transmembrane domain. In certain embodiments, the native transmembrane domain is VIIPMC LVLLLLALIL PLLFY (UniProt entry Q6UVK1) (SEQ ID NO: 44).

In one embodiment, the anti-MCSP antibodies induce lysis of cells expressing MCSP. Lysis can be induced by any mechanism, such as by mediating an effector function, such as C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation, or by directly inducing apoptosis of the cells.

In one embodiment, the anti-MCSP antibody is glycoengineered to have at least one increase in effector function as compared to the non-glycoengineered parent anti-MCSP antibody. The increase in effector function is increased binding affinity is to an Fc receptor, increased antibody-dependent cellular cytotoxicity (ADCC); increased binding to NK cells; increased binding to macrophages; increased binding to polymorphonuclear cells; increased binding to monocytes; direct signaling inducing apoptosis; increased dendritic cell maturation; or increased T cell priming. The glycoengineered anti-MCSP antibodies provide a survival benefit in subjects suffering from cancers which express MCSP as compared to non-glycoengineered antibodies directed to the same epitope of MCSP.

In one aspect, the invention provides an anti-MCSP antibody comprising at least one, two, three, four, five, or six HVRs selected from (a) HVR-H1 comprising the amino acid sequence of SEQ ID NO: 14; (b) HVR-H2 comprising the amino acid sequence of SEQ ID NO: 15; (c) HVR-H3 comprising the amino acid sequence of SEQ ID NO: 16; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12.

In one aspect, the invention provides an anti-MCSP antibody comprising at least one, at least two, or all three VH HVR sequences selected from (a) HVR-H1 comprising the amino acid sequence of SEQ ID NO: 14; (b) HVR-H2 comprising the amino acid sequence of SEQ ID NO: 15; and (c) HVR-H3 comprising the amino acid sequence of SEQ ID NO: 16. In a further embodiment, the antibody comprises (a) HVR-H1 comprising the amino acid sequence of SEQ ID NO: 14; (b) HVR-H2 comprising the amino acid sequence of SEQ ID NO: 15; and (c) HVR-H3 comprising the amino acid sequence of SEQ ID NO: 16.

In one aspect, the invention provides an anti-MCSP antibody comprising at least one, at least two, or all three VL HVR sequences selected from (a) HVR-L1 comprising the amino acid sequence of SEQ ID NO: 10; (b) HVR-L2 comprising the amino acid sequence of SEQ ID NO: 11 and (c) HVR-L3 comprising the amino acid sequence of SEQ ID NO: 12. In one embodiment, the antibody comprises (a) HVR-L1 comprising the amino acid sequence of SEQ ID NO: 10; (b) HVR-L2 comprising the amino acid sequence of SEQ ID NO: 11; and (c) HVR-L3 comprising the amino acid sequence of SEQ ID NO: 12.

In another aspect, an anti-MCSP antibody of the invention comprises (a) a VH domain comprising at least one, at least two, or all three VH HVR sequences selected from (i) HVR-H1 comprising the amino acid sequence of SEQ ID NO: 14, (ii) HVR-H2 comprising the amino acid sequence of SEQ ID NO: 15, and (iii) HVR-H3 comprising an amino acid sequence selected from SEQ ID NO: 16; and (b) a VL domain comprising at least one, at least two, or all three VL HVR sequences selected from (i) HVR-L1 comprising the amino acid sequence of SEQ ID NO: 10, (ii) HVR-L2 comprising the amino acid sequence of SEQ ID NO: 11, and (c) HVR-L3 comprising the amino acid sequence of SEQ ID NO: 12.

In another aspect, the invention provides an anti-MCSP antibody comprising (a) HVR-H1 comprising the amino acid sequence of SEQ ID NO: 14; (b) HVR-H2 comprising the amino acid sequence of SEQ ID NO: 15; (c) HVR-H3 comprising the amino acid sequence of SEQ ID NO: 16; (d) HVR-L1 comprising the amino acid sequence of SEQ ID NO: 10; (e) HVR-L2 comprising the amino acid sequence of SEQ ID NO: 11; and (f) HVR-L3 comprising an amino acid sequence selected from SEQ ID NO: 12.

In one aspect, the invention provides an anti-MCSP antibody comprising at least one, two, three, four, five, or six HVRs selected from (a) HVR-H1 comprising the amino acid sequence of SEQ ID NO: 17; (b) HVR-H2 comprising the amino acid sequence of SEQ ID NO: 18; (c) HVR-H3 comprising the amino acid sequence of SEQ ID NO: 16; (d) HVR-L1 comprising the amino acid sequence of SEQ ID NO: 13; (e) HVR-L2 comprising the amino acid sequence of SEQ ID NO: 11; and (f) HVR-L3 comprising the amino acid sequence of SEQ ID NO: 12.

In one aspect, the invention provides an anti-MCSP antibody comprising at least one, at least two, or all three VH HVR sequences selected from (a) HVR-H1 comprising the amino acid sequence of SEQ ID NO: 17; (b) HVR-H2 comprising the amino acid sequence of SEQ ID NO: 18; and (c) HVR-H3 comprising the amino acid sequence of SEQ ID NO: 16. In a further embodiment, the antibody comprises (a) HVR-H1 comprising the amino acid sequence of SEQ ID NO: 17; (b) HVR-H2 comprising the amino acid sequence of SEQ ID NO: 18; and (c) HVR-H3 comprising the amino acid sequence of SEQ ID NO: 16.

In one aspect, the invention provides an anti-MCSP antibody comprising at least one, at least two, or all three VL HVR sequences selected from (a) HVR-L1 comprising the amino acid sequence of SEQ ID NO: 13; (b) HVR-L2 comprising the amino acid sequence of SEQ ID NO: 11; and (c) HVR-L3 comprising the amino acid sequence of SEQ ID NO: 12. In one embodiment, the antibody comprises (a) HVR-L1 comprising the amino acid sequence of SEQ ID NO: 13; (b) HVR-L2 comprising the amino acid sequence of SEQ ID NO: 11; and (c) HVR-L3 comprising the amino acid sequence of SEQ ID NO: 12.

In another aspect, an anti-MCSP antibody of the invention comprises (a) a VH domain comprising at least one, at least two, or all three VH HVR sequences selected from (i) HVR-H1 comprising the amino acid sequence of SEQ ID NO: 17, (ii) HVR-H2 comprising the amino acid sequence of SEQ ID NO: 18, and (iii) HVR-H3 comprising an amino acid sequence selected from SEQ ID NO: 16; and (b) a VL domain comprising at least one, at least two, or all three VL HVR sequences selected from (i) HVR-L1 comprising the amino acid sequence of SEQ ID NO: 13, (ii) HVR-L2 comprising the amino acid sequence of SEQ ID NO: 11, and (c) HVR-L3 comprising the amino acid sequence of SEQ ID NO: 12.

In another aspect, the invention provides an anti-MCSP antibody comprising (a) HVR-H1 comprising the amino acid sequence of SEQ ID NO: 17; (b) HVR-H2 comprising the amino acid sequence of SEQ ID NO: 18; (c) HVR-H3 comprising the amino acid sequence of SEQ ID NO: 16; (d) HVR-L1 comprising the amino acid sequence of SEQ ID NO: 13; (e) HVR-L2 comprising the amino acid sequence of SEQ ID NO: 11; and (f) HVR-L3 comprising an amino acid sequence selected from SEQ ID NO: 12.

In another aspect, the invention provides an anti-MCSP antibody comprising (a) HVR-H1 comprising the amino acid sequence of SEQ ID NO: 17; (b) HVR-H2 comprising the amino acid sequence of SEQ ID NO: 18; (c) HVR-H3 comprising the amino acid sequence of SEQ ID NO: 16; (d) HVR-L1 comprising the amino acid sequence of SEQ ID NO: 10; (e) HVR-L2 comprising the amino acid sequence of SEQ ID NO: 11; and (f) HVR-L3 comprising an amino acid sequence selected from SEQ ID NO: 12.

In another aspect, the invention provides an anti-MCSP antibody comprising (a) HVR-H1 comprising the amino acid sequence of SEQ ID NO: 14; (b) HVR-H2 comprising the amino acid sequence of SEQ ID NO: 18; (c) HVR-H3 comprising the amino acid sequence of SEQ ID NO: 16; (d) HVR-L1 comprising the amino acid sequence of SEQ ID NO: 10; (e) HVR-L2 comprising the amino acid sequence of SEQ ID NO: 11; and (f) HVR-L3 comprising an amino acid sequence selected from SEQ ID NO: 12.

In another aspect, the invention provides an anti-MCSP antibody comprising (a) HVR-H1 comprising the amino acid sequence of SEQ ID NO: 14; (b) HVR-H2 comprising the amino acid sequence of SEQ ID NO: 18; (c) HVR-H3 comprising the amino acid sequence of SEQ ID NO: 16; (d) HVR-L1 comprising the amino acid sequence of SEQ ID NO: 13; (e) HVR-L2 comprising the amino acid sequence of SEQ ID NO: 11; and (f) HVR-L3 comprising an amino acid sequence selected from SEQ ID NO: 12.

In one aspect, an anti-MCSP antibody comprises a VH sequence having at least 90%, 91%, 92%, 93%, 94%, 95%, 96%, 97%, 98%, 99%, or 100% sequence identity to the amino acid sequence of SEQ ID NO: 27. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-MCSP antibody comprising that sequence retains the ability to bind to MCSP. In certain embodiments, a total of 1 to 10 amino acids have been substituted, inserted and/or deleted in SEQ ID NO: 27. In certain embodiments, substitutions, insertions, or deletions occur in regions outside the HVRs (i.e., in the FRs). Optionally, the anti-MCSP antibody comprises the VH sequence of SEQ ID NO: 27, including post-translational modifications of that sequence. In a particular embodiment, the VH comprises one, two or three HVRs selected from: (a) HVR-H1 comprising the amino acid sequence of SEQ ID NO: 14, (b) HVR-H2 comprising the amino acid sequence of SEQ ID NO: 15, and (c) HVR-H3 comprising the amino acid sequence of SEQ ID NO: 16.

In another aspect, an anti-MCSP antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 26. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-MCSP antibody comprising that sequence retains the ability to bind to MCSP. In certain embodiments, a total of 1 to 10 amino acids have been substituted, inserted and/or deleted in SEQ ID NO: 26. In certain embodiments, the substitutions, insertions, or deletions occur in regions outside the HVRs (i.e., in the FRs). Optionally, the anti-MCSP antibody comprises the VL sequence of SEQ ID NO: 26, including post-translational modifications of that sequence. In a particular embodiment, the VL comprises one, two or three HVRs selected from (a) HVR-L1 comprising the amino acid sequence of SEQ ID NO: 10; (b) HVR-L2 comprising the amino acid sequence of SEQ ID NO: 11; and (c) HVR-L3 comprising the amino acid sequence of SEQ ID NO: 12.

In another aspect, an anti-MCSP antibody is provided, wherein the antibody comprises a VH as in any of the embodiments provided above, and a VL as in any of the embodiments provided above. In one embodiment, the antibody comprises a VH comprising the amino acid sequence of SEQ ID NO: 27 and a VL sequence in SEQ ID NO: 26, including post-translational modifications of those sequences.

In another aspect, an anti-MCSP antibody comprises a VH sequence having at least 90%, 91%, 92%, 93%, 94%, 95%, 96%, 97%, 98%, 99%, or 100% sequence identity to the amino acid sequence of SEQ ID NO: 32. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-MCSP antibody comprising that sequence retains the ability to bind to MCSP. In certain embodiments, a total of 1 to 10 amino acids have been substituted, inserted and/or deleted in SEQ ID NO: 32. In certain embodiments, substitutions, insertions, or deletions occur in regions outside the HVRs (i.e., in the FRs). Optionally, the anti-MCSP antibody comprises the VH sequence of SEQ ID NO: 32, including post-translational modifications of that sequence. In a particular embodiment, the VH comprises one, two or three HVRs selected from: (a) HVR-H1 comprising the amino acid sequence of SEQ ID NO: 17, (b) HVR-H2 comprising the amino acid sequence of SEQ ID NO: 18, and (c) HVR-H3 comprising the amino acid sequence of SEQ ID NO: 16.

In another aspect, an anti-MCSP antibody comprises a VL sequence having at least 90%, 91%, 92%, 93%, 94%, 95%, 96%, 97%, 98%, 99%, or 100% sequence identity to the amino acid sequence of SEQ ID NO: 31 In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-MCSP antibody comprising that sequence retains the ability to bind to MCSP. In certain embodiments, a total of 1 to 10 amino acids have been substituted, inserted and/or deleted in SEQ ID NO: 31. In certain embodiments, substitutions, insertions, or deletions occur in regions outside the HVRs (i.e., in the FRs). Optionally, the anti-MCSP antibody comprises the VL sequence in SEQ ID NO: 31, including post-translational modifications of that sequence. In a particular embodiment, the VL comprises one, two or three HVRs selected from: (a) HVR-L1 comprising the amino acid sequence of SEQ ID NO: 13, (b) HVR-L2 comprising the amino acid sequence of SEQ ID NO: 11, and (c) HVR-L3 comprising the amino acid sequence of SEQ ID NO: 12.

In another aspect, an anti-MCSP antibody is provided, wherein the antibody comprises a VH as in any of the embodiments provided above, and a VL as in any of the embodiments provided above. In one embodiment, the antibody comprises the VH comprising the amino acid sequence of SEQ ID NO: 32 and a VL comprising the amino acid sequence of SEQ ID NO: 31, including post-translational modifications of those sequences.

In another aspect, an anti-MCSP antibody comprises a VH sequence having at least 90%, 91%, 92%, 93%, 94%, 95%, 96%, 97%, 98%, 99%, or 100% sequence identity to the amino acid sequence of SEQ ID NO: 29. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-MCSP antibody comprising that sequence retains the ability to bind to MCSP. In certain embodiments, a total of 1 to 10 amino acids have been substituted, inserted and/or deleted in SEQ ID NO: 29. In certain embodiments, substitutions, insertions, or deletions occur in regions outside the HVRs (i.e., in the FRs). Optionally, the anti-MCSP antibody comprises the VH sequence of SEQ ID NO: 29, including post-translational modifications of that sequence. In a particular embodiment, the VH comprises one, two or three HVRs selected from: (a) HVR-H1 comprising the amino acid sequence of SEQ ID NO: 14, (b) HVR-H2 comprising the amino acid sequence of SEQ ID NO: 18, and (c) HVR-H3 comprising the amino acid sequence of SEQ ID NO: 16.

In another aspect, an anti-MCSP antibody comprises a VL sequence having at least 90%, 91%, 92%, 93%, 94%, 95%, 96%, 97%, 98%, 99%, or 100% sequence identity to the amino acid sequence of SEQ ID NO: 28. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-MCSP antibody comprising that sequence retains the ability to bind to MCSP. In certain embodiments, a total of 1 to 10 amino acids have been substituted, inserted and/or deleted in SEQ ID NO: 28. In certain embodiments, substitutions, insertions, or deletions occur in regions outside the HVRs (i.e., in the FRs). Optionally, the anti-MCSP antibody comprises the VL sequence in SEQ ID NO: 28, including post-translational modifications of that sequence. In a particular embodiment, the VL comprises one, two or three HVRs selected from: (a) HVR-L1 comprising the amino acid sequence of SEQ ID NO: 10, (b) HVR-L2 comprising the amino acid sequence of SEQ ID NO: 11, and (c) HVR-L3 comprising the amino acid sequence of SEQ ID NO: 12.

In another aspect, an anti-MCSP antibody is provided, wherein the antibody comprises a VH as in any of the embodiments provided above, and a VL as in any of the embodiments provided above. In one embodiment, the antibody comprises the VH comprising the amino acid sequence of SEQ ID NO: 29 and a VL comprising the amino acid sequence of SEQ ID NO: 28, including post-translational modifications of those sequences.

In another aspect, an anti-MCSP antibody comprises a heavy chain sequence having at least 90%, 91%, 92%, 93%, 94%, 95%, 96%, 97%, 98%, 99%, or 100% sequence identity to the amino acid sequence of SEQ ID NO: 35. In certain embodiments, a heavy chain sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-MCSP antibody comprising that sequence retains the ability to bind to MCSP. In certain embodiments, a total of 1 to 10 amino acids have been substituted, inserted and/or deleted in SEQ ID NO: 35. In certain embodiments, substitutions, insertions, or deletions occur in regions outside the HVRs (i.e., in the FRs). Optionally, the anti-MCSP antibody comprises the heavy chain sequence of SEQ ID NO: 35, including post-translational modifications of that sequence.

In another aspect, an anti-MCSP antibody is provided, wherein the antibody comprises a light chain having at least 90%, 91%, 92%, 93%, 94%, 95%, 96%, 97%, 98%, 99%, or 100% sequence identity to the amino acid sequence of SEQ ID NO: 34. In certain embodiments, a light chain sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-MCSP antibody comprising that sequence retains the ability to bind to MCSP. In certain embodiments, a total of 1 to 10 amino acids have been substituted, inserted and/or deleted in SEQ ID NO: 34. In certain embodiments, the substitutions, insertions, or deletions occur in regions outside the HVRs (i.e., in the FRs). Optionally, the anti-MCSP antibody comprises the light chain sequence of SEQ ID NO: 34, including post-translational modifications of that sequence.

In another aspect, an anti-MCSP antibody is provided, wherein the antibody comprises a heavy chain as in any of the embodiments provided above, and a light chain in any of the embodiments provided above. In one embodiment, the antibody comprises a heavy chain comprising the amino acid sequence of SEQ ID NO: 35 and a light chain sequence comprising the amino acid sequence of SEQ ID NO: 34, including post-translational modifications of those sequences.

In another aspect, an anti-MCSP antibody comprises a heavy chain sequence having at least 90%, 91%, 92%, 93%, 94%, 95%, 96%, 97%, 98%, 99%, or 100% sequence identity to the amino acid sequence of SEQ ID NO: 37. In certain embodiments, a heavy chain sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-MCSP antibody comprising that sequence retains the ability to bind to MCSP. In certain embodiments, a total of 1 to 10 amino acids have been substituted, inserted and/or deleted in SEQ ID NO: 37. In certain embodiments, substitutions, insertions, or deletions occur in regions outside the HVRs (i.e., in the FRs). Optionally, the anti-MCSP antibody comprises the heavy chain sequence of SEQ ID NO: 37, including post-translational modifications of that sequence.

In another aspect, an anti-MCSP antibody is provided, wherein the antibody comprises a light chain having at least 90%, 91%, 92%, 93%, 94%, 95%, 96%, 97%, 98%, 99%, or 100% sequence identity to the amino acid sequence of SEQ ID NO: 36. In certain embodiments, a light chain sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-MCSP antibody comprising that sequence retains the ability to bind to MCSP. In certain embodiments, a total of 1 to 10 amino acids have been substituted, inserted and/or deleted in SEQ ID NO: 36. In certain embodiments, the substitutions, insertions, or deletions occur in regions outside the HVRs (i.e., in the FRs). Optionally, the anti-MCSP antibody comprises the light chain sequence of SEQ ID NO: 36, including post-translational modifications of that sequence.

In another aspect, an anti-MCSP antibody is provided, wherein the antibody comprises a heavy chain as in any of the embodiments provided above, and a light chain in any of the embodiments provided above. In one embodiment, the antibody comprises a heavy chain comprising the amino acid sequence of SEQ ID NO: 37 and a light chain sequence comprising the amino acid sequence of SEQ ID NO: 36, including post-translational modifications of those sequences In a further aspect, the invention provides an antibody that binds to the same epitope or epitopes as an anti-MCSP antibody provided herein.

In one embodiment, an antibody is provided that binds to the same epitope as an anti-MCSP antibody having a VH comprising the amino acid sequence of SEQ ID NO: 27 and a VL comprising the amino acid sequence of SEQ ID NO: 26 In another embodiment, an antibody is provided that binds to the same epitope as an anti-MCSP antibody having a VH comprising the amino acid sequence of SEQ ID NO: 32 and a VL comprising the amino acid sequence of SEQ ID NO: 31.

In other embodiments, an antibody is provided that competes for binding to the same epitope as an anti-MCSP antibody as described herein.

In one embodiment, the antibody that binds to the same epitope, and/or competes for binding to the same epitope as an anti-MCSP antibody exhibits effector function activities, such as, for example, Fc-mediated cellular cytotoxicity, including ADCC activity.

In one embodiment, the anti-MCSP antibody binds to a membrane proximal epitope of human MCSP. In one embodiment, the anti-MCSP antibody binds to a membrane proximal epitope of human MCSP comprising a CSPG repeat-containing domain. In one embodiment, anti-MCSP antibody binds to membrane proximal epitope of human MCSP that is from, within, or overlapping the amino acid sequence of SEQ ID NO: 5. In one embodiment, anti-MCSP antibody binds to membrane proximal epitope of human MCSP that is from, within, or overlapping the amino acid sequence of SEQ ID NO: 4. In one embodiment, anti-MCSP antibody binds to membrane proximal epitope of human MCSP that is from, within, or overlapping the amino acid sequence of SEQ ID NO: 3.

In a further aspect of the invention, an anti-MCSP antibody according to any of the above embodiments is a monoclonal antibody, including a chimeric, humanized or human antibody. In one embodiment, an anti-MCSP antibody is an antibody fragment, e.g., a Fv, Fab, Fab', scFv, diabody, or F(ab')$_2$ fragment. In another embodiment, the antibody is a full length antibody, e.g., an intact IgG1 antibody or other antibody class or isotype as defined herein.

In one embodiment, the anti-MCSP antibody is the mouse monoclonal antibody LC007. The nucleic acid sequences for the heavy and light chains of this antibody are presented in SEQ ID NOs: 37 and 36, respectively. In one embodiment, the anti-MSCP antibody is a chimeric antibody derived from mouse monoclonal antibody LC007. In one embodiment, the anti-MSCP antibody is a humanized antibody derived from mouse monoclonal antibody LC007. In one embodiment, the anti-MSCP antibody is a human antibody derived from mouse monoclonal antibody LC007.

In a further aspect, an anti-MCSP antibody according to any of the above embodiments may incorporate any of the features, singly or in combination, as described in Sections 1-7 below:

1. Antibody Affinity

In certain embodiments, an antibody provided herein has a dissociation constant (Kd) of ≤1 µM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M).

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881 (1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm bandpass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA,* 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCIMOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications,* pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178:1-37 (O'Brien et al., ed., Human Press, Totowa, N.J., 2001) and further described, e.g., in the McCafferty et al., *Nature* 348: 552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101 (34): 12467-12472 (2004); and Lee et al., *J. Immunol. Methods* 284(1-2): 119-132 (2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.*, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for MCSP and the other is for any other antigen. In certain embodiments, bispecific antibodies may bind to two different epitopes of MCSP. Bispecific antibodies may also be used to localize cytotoxic agents to cells which express MCSP. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science*, 229: 81 (1985)); using leucine zippers to produce bi-specific antibodies (see, e.g., Kostelny et al., *J. Immunol.*, 148(5):1547-1553 (1992)); using "diabody" technology for making bispecific antibody fragments (see, e.g., Hollinger et al., *Proc. Natl. Acad. Sci. USA*, 90:6444-6448 (1993)); and using single-chain Fv (sFv) dimers (see, e.g. Gruber et al., *J. Immunol.*, 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to MCSP as well as another, different antigen (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "conservative substitutions." More substantial changes are provided in Table 1 under the heading of "exemplary substitutions," and as further described below in reference to amino acid side chain classes Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.,* 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

Accordingly, the present invention is further directed to a method for modifying the glycosylation profile of the anti-MCSP antibodies of the present invention that are produced by a host cell, comprising expressing in said host cell a nucleic acid encoding an anti-MCSP antibody of the invention and a nucleic acid encoding a polypeptide with a glycosyltransferase activity, or a vector comprising such nucleic acids. Genes with glycosyltransferase activity include β(1,4)-N-acetylglucosaminyltransferase III (GnTII), α-mannosidase II (ManII), β(1,4)-galactosyltransferase (GalT), β(1,2)-N-acetylglucosaminyltransferase I (GnTI), and β(1,2)-N-acetylglucosaminyltransferase II (GnTII). In one embodiment, a combination of genes with glycosyltransferase activity are expressed in the host cell (e.g., GnTIII and Man II). Likewise, the method also encompasses expression of one or more polynucleotide(s) encoding an anti-MCSP antibody in a host cell in which a glycosyltransferase gene has been disrupted or otherwise deactivated (e.g., a host cell in which the activity of the gene encoding α1-6 core fucosyltransferase has been knocked out). In another embodiment, the anti-MCSP antibodies of the present invention can be produced in a host cell that further expresses a polynucleotide encoding a polypeptide having GnTIII activity to modify the glycosylation pattern. In a specific embodiment, the polypeptide having GnTIII activity is a fusion polypeptide comprising the Golgi localization domain of a Golgi resident polypeptide. The term Golgi localization domain refers to the amino acid sequence of a Golgi resident polypeptide which is responsible for anchoring the polypeptide in location within the Golgi complex. Generally, localization domains comprise amino terminal "tails" of an enzyme. In another preferred embodiment, the expression of the anti-MCSP antibodies of the present invention in a host cell that expresses a polynucleotide encoding a polypeptide having GnTIII activity results in anti-MCSP antibodies with increased Fc receptor binding affinity and increased effector function. Accordingly, in one embodiment, the present invention is directed to a host cell comprising (a) an isolated nucleic acid comprising a sequence encoding a polypeptide having GnTIII activity; and (b) an isolated polynucleotide encoding an anti-MCSP antibody of the present invention, such as a chimeric, primatized or humanized antibody that binds human MCSP. In a preferred embodiment, the polypeptide having GnTIII activity is a fusion polypeptide comprising the catalytic domain of GnTIII and the Golgi localization domain is the localization domain of mannosidase II. Methods for generating such fusion polypeptides and using them to produce antibodies with increased effector functions are disclosed in U.S. Provisional Pat. Appl. No. 60/495,142 and U.S. Pat. Appl. Publ. No. 2004/0241817, the entire contents of which are expressly incorporated herein by reference. In a particular embodiment, the modified anti-MCSP antibody produced by the host cell has an IgG constant region or a fragment thereof comprising the Fc region. In another particular embodiment the anti-MCSP antibody is a humanized antibody or a fragment thereof comprising an Fc region.

Anti-MCSP antibodies with altered glycosylation produced by the host cells of the invention typically exhibit increased Fc receptor binding affinity and/or increased effector function as a result of the modification of the host cell (e.g., by expression of a glycosyltransferase gene). Preferably, the increased Fc receptor binding affinity is increased binding to a Fcγ activating receptor, such as the FcγRIIIa receptor. The increased effector function is preferably an increase in one or more of the following: increased antibody-dependent cellular cytotoxicity, increased antibody-dependent cellular phagocytosis (ADCP), increased cytokine secretion, increased immune-complex-mediated antigen uptake by antigen-presenting cells, increased Fc-mediated cellular cytotoxicity, increased binding to NK cells, increased binding to macrophages, increased binding to polymorphonuclear cells (PMNs), increased binding to monocytes, increased crosslinking of target-bound antibodies, increased direct signaling inducing apoptosis, increased dendritic cell maturation, and increased T cell priming.

In one aspect, the present invention provides glycoforms of an anti-MCSP antibody (e.g., variant antibody) having increased effector function as compared to the anti-MCSP antibody that has not been glycoengineered, including anti-body-dependent cellular cytotoxicity. Glycosylation engineering of antibodies has been previously described. See, e.g., U.S. Pat. No. 6,602,684, incorporated herein by reference in its entirety. Methods of producing anti-MCSP antibodies from host cells that have altered activity of genes involved in glycosylation are also described herein in detail (See, e.g, preceding section entitled "Expression Vectors and Host Cells"). Increases in ADCC of the anti-MCSP antibodies of the present invention is also achieved by increasing affinity of the antibody for MCSP, for example by affinity maturation or other methods of improving affinity (see Tang et al., J. Immunol. 2007, 179:2815-2823). Combinations of these approaches are also encompassed by the present invention.

Clinical trials of unconjugated monoclonal antibodies (mAbs) for the treatment of some types of cancer have recently yielded encouraging results. Dillman, Cancer Biother. & Radiopharm. 12:223-25 (1997); Deo et al., Immunology Today 18:127 (1997). A chimeric, unconjugated IgG1 has been approved for low-grade or follicular B-cell non-Hodgkin's lymphoma. Dillman, Cancer Biother. & Radiopharm. 12:223-25 (1997), while another unconjugated mAb, a humanized IgG1 targeting solid breast tumors, has also showed promising results in phase III clinical trials. Deo et al., Immunology Today 18:127 (1997). The antigens of these two mAbs are highly expressed in their respective tumor cells and the antibodies mediate potent tumor destruction by effector cells in vitro and in vivo. In contrast, many other unconjugated mAbs with fine tumor specificities cannot trigger effector functions of sufficient potency to be clinically useful. Frost et al., Cancer 80:317-33 (1997); Surfus et al., J. Immunother. 19:184-91 (1996). For some of these weaker mAbs, adjunct cytokine therapy is currently being tested. Addition of cytokines can stimulate antibody-dependent cellular cytotoxicity (ADCC) by increasing the activity and number of circulating lymphocytes. Frost et al., Cancer 80:317-33 (1997); Surfus et al., J. Immunother. 19:184-91 (1996). ADCC, a lytic attack on targeted cells, is triggered upon binding of leukocyte receptors to the constant region (Fc) of antibodies. Deo et al., Immunology Today 18:127 (1997).

A different, but complementary, approach to increase ADCC activity of unconjugated IgG1s is to engineer the Fc region of the antibody. Protein engineering studies have shown that FcγRs interact with the lower hinge region of the IgG CH2 domain. Lund et al., J. Immunol. 157:4963-69 (1996). However, FcγR binding also requires the presence of oligosaccharides covalently attached at the conserved Asn 297 in the CH2 region. Lund et al., J. Immunol. 157:4963-69 (1996); Wright and Morrison, Trends Biotech. 15:26-31 (1997), suggesting that either oligosaccharide and polypeptide both directly contribute to the interaction site or that the oligosaccharide is required to maintain an active CH2 polypeptide conformation. Modification of the oligosaccharide structure can therefore be explored as a means to increase the affinity of the interaction.

An IgG molecule carries two N-linked oligosaccharides in its Fc region, one on each heavy chain. As any glycoprotein, an antibody is produced as a population of glycoforms which share the same polypeptide backbone but have different oligosaccharides attached to the glycosylation sites. The oligosaccharides normally found in the Fc region of serum IgG are of complex bi-antennary type (Wormald et al., Biochemistry 36:130-38 (1997), with a low level of terminal sialic acid and bisecting N-acetylglucosamine (GlcNAc), and a variable degree of terminal galactosylation and core fucosylation. Some studies suggest that the minimal carbohydrate structure required for FcγR binding lies within the oligosaccharide core. Lund et al., J. Immunol. 157:4963-69 (1996).

The mouse- or hamster-derived cell lines used in industry and academia for production of unconjugated therapeutic mAbs normally attach the required oligosaccharide determinants to Fc sites. IgGs expressed in these cell lines lack, however, the bisecting GlcNAc found in low amounts in serum IgGs. Lifely et al., Glycobiology 318:813-22 (1995). In contrast, it was recently observed that a rat myeloma-produced, humanized IgG1 (CAMPATH-1H) carried a bisecting GlcNAc in some of its glycoforms. Lifely et al., Glycobiology 318:813-22 (1995). The rat cell-derived antibody reached a similar maximal in vitro ADCC activity as CAMPATH-1H antibodies produced in standard cell lines, but at significantly lower antibody concentrations.

The CAMPATH antigen is normally present at high levels on lymphoma cells, and this chimeric mAb has high ADCC activity in the absence of a bisecting GlcNAc. Lifely et al., Glycobiology 318:813-22 (1995). In the N-linked glycosylation pathway, a bisecting GlcNAc is added by GnTIII. Schachter, Biochem. Cell Biol. 64:163-81 (1986).

Previous studies used a single, antibody-producing CHO cell line that was previously engineered to express, in an externally-regulated fashion, different levels of a cloned GnTIII enzyme gene (Umaña, P., et al., Nature Biotechnol. 17:176-180 (1999)). This approach established for the first time a rigorous correlation between expression of a glycosyltransferase (e.g., GnTIII) and the ADCC activity of the modified antibody. Thus, the invention contemplates an anti-MCSP antibody, comprising an Fc region or region equivalent to an Fc region having altered glycosylation resulting from changing the expression level of a glycosyltransferase gene in the antibody-producing host cell. In a specific embodiment, the change in gene expression level is an increase in GnTIII activity. Increased GnTIII activity results in an increase in the percentage of bisected oligosaccharides, as well as a decrease in the percentage of fucose residues, in the Fc region of the antibody. This antibody, or fragment thereof, has increased Fc receptor binding affinity and increased effector function.

The present invention is also directed to a method for producing an anti-MCSP antibody of the present invention having modified oligosaccharides, comprising (a) culturing a host cell engineered to express at least one nucleic acid encoding a polypeptide having glycosyltransferase activity under conditions which permit the production of an anti-MCSP antibody according to the present invention, wherein said polypeptide having glycosyltransferase activity is expressed in an amount sufficient to modify the oligosaccharides in the Fc region of said anti-MCSP antibody produced by said host cell; and (b) isolating said anti-MCSP antibody. In one embodiment, the polypeptide having glycosyltransferase activity is GnTIII.

In another embodiment, there are two polypeptides having glycosyltransferase activity. In a particular embodiment, the two peptides having glycosyltransferase activity are GnTIII and ManII. In another embodiment, the polypeptide having glycosyltransferase activity is a fusion polypeptide comprising the catalytic domain of GnTIII. In a more specific embodiment, the fusion polypeptide further comprises the Golgi localization domain of a Golgi resident polypeptide. Preferably, the Golgi localization domain is the localization domain of mannosidase II or GnTI. Alternatively, the Golgi localization domain is selected from the group consisting of: the localization domain of mannosidase I, the localization domain of GnTII, and the localization domain of α 1-6 core fucosyltransferase. The anti-MCSP antibodies produced by the methods of the present invention have increased Fc receptor binding affinity and/or increased effector function. Generally, the increased effector function is one or more of the following: increased Fc-mediated cellular cytotoxicity (including increased antibody-dependent cellular cytotoxicity), increased antibody-dependent cellular phagocytosis (ADCP), increased cytokine secretion, increased immune-complex-mediated antigen uptake by antigen-presenting cells, increased binding to NK cells, increased binding to macrophages, increased binding to monocytes, increased binding to polymorphonuclear cells, increased direct signaling inducing apoptosis, increased crosslinking of target-bound antibodies, increased dendritic cell maturation, or increased T cell priming. The increased Fc receptor binding affinity is preferably increased binding to Fc activating receptors such as FcγRIIIa. In a particularly preferred embodiment the ABM is a humanized antibody or a fragment thereof.

In one embodiment, the percentage of bisected N-linked oligosaccharides in the Fc region of the anti-MCSP antibody is at least about 10% to about 100%, specifically at least about 50%, more specifically, at least about 60%, at least about 70%, at least about 80%, or at least about 90-95% of the total oligosaccharides. In yet another embodiment, the antibody produced by the methods of the invention has an increased proportion of nonfucosylated oligosaccharides in the Fc region as a result of the modification of its oligosaccharides by the methods of the present invention. In one embodiment, the percentage of nonfucosylated oligosaccharides is at least about 20% to about 100%, specifically at least about 50%, at least about 60% to about 70%, and more specifically, at least about 75%. The nonfucosylated oligosaccharides may be of the hybrid or complex type. In yet another embodiment, the antibody produced by the methods of the invention has an increased proportion of bisected oligosaccharides in the Fc region as a result of the modification of its oligosaccharides by the methods of the present invention. In one embodiment, the percentage of bisected oligosaccharides is at least about 20% to about 100%, specifically at least about 50%, at least about 60% to about 70%, and more specifically, at least about 75%. In a particularly preferred embodiment, the anti-MCSP antibody produced by the host cells and methods of the invention has an increased proportion of bisected, nonfucosylated oligosaccharides in the Fc region. The bisected, nonfucosylated oligosaccharides may be either hybrid or complex. Specifically, the methods of the present invention may be used to produce antibodies in which at least about 10% to about 100%, specifically at least about 15%, more specifically at least about 20% to about 50%, more specifically at least about 20% to about 25%, and more specifically at least about 30% to about 35% of the oligosaccharides in the Fc region of the antibody are bisected, nonfucosylated. The anti-MCSP antibodies of the present invention may also comprise an Fc region in which at least about 10% to about 100%, specifically at least about 15%, more specifically at least about 20% to about 25%, and more specifically at least about 30% to about 35% of the oligosaccharides in the Fc region of the anti-MCSP antibody are bisected hybrid nonfucosylated.

In another embodiment, the present invention is directed to an anti-MCSP antibody engineered to have increased effector function and/or increased Fc receptor binding affinity, produced by the methods of the invention. The increased effector function can include, but is not limited to one or more of the following: increased Fc-mediated cellular cytotoxicity (including increased antibody-dependent cellular cytotoxicity), increased antibody-dependent cellular phagocytosis (ADCP), increased cytokine secretion, increased immune-complex-mediated antigen uptake by antigen-presenting cells, increased binding to NK cells, increased binding to macrophages, increased binding to monocytes, increased binding to polymorphonuclear cells, increased direct signaling inducing apoptosis, increased crosslinking of target-bound antibodies, increased dendritic cell maturation, or increased T cell priming. In a preferred embodiment, the increased Fc receptor binding affinity is increased binding to an Fc activating receptor, most preferably FcγRIIIa. In one embodiment, the antibody is an intact antibody. In one embodiment, the antibody is an antibody fragment containing the Fc region, or a fusion protein that includes a region equivalent to the Fc region of an immunoglobulin.

The present invention further provides methods for the generation and use of host cell systems for the production of glycoforms of the antibodies of the present invention, having increased Fc receptor binding affinity, preferably increased binding to Fc activating receptors, and/or having increased effector functions, including antibody-dependent cellular cytotoxicity. The glycoengineering methodology that can be used with the antibodies of the present invention has been described in greater detail in U.S. Pat. No. 6,602,684, U.S. Pat. Appl. Publ. No. 2004/0241817 A1, U.S. Pat. Appl. Publ. No. 2003/0175884 A1, Provisional U.S. Patent Application No. 60/441,307 and WO 2004/065540, the entire contents of each of which is incorporated herein by reference in its entirety. The antibodies of the present invention can alternatively be glycoengineered to have reduced fucose residues in the Fc region according to the techniques disclosed in U.S. Pat. Appl. Pub. No. 2003/0157108 (Genentech), or in EP 1 176 195 A1, WO 03/084570, WO 03/085119 and U.S. Pat. Appl. Pub. Nos. 2003/0115614, 2004/093621, 2004/110282, 2004/110704, 2004/132140 (Kyowa). The contents of each of these documents are herein incorporated by reference in their entireties. Glycoengineered antibodies of the invention may also be produced in expression systems that produce modified glycoproteins, such as those taught in U.S. Pat. Appl. Pub. No. 60/344,169 and WO 03/056914 (GlycoFi, Inc.) or in WO 2004/057002 and WO 2004/024927 (Greenovation), the contents of each of which are hereby incorporated by reference in their entirety.

In another aspect, the present invention provides host cell expression systems for the generation of the antibodies of the present invention having modified glycosylation patterns. In particular, the present invention provides host cell systems for the generation of glycoforms of the antibodies of the present invention having an improved therapeutic value. Therefore, the invention provides host cell expression systems selected or engineered to express a polypeptide having a glycosyltransferase activity. In a specific embodiment, the glycosyltransferase activity is a GnTIII activity. In one embodiment, the polypeptide having GnTIII activity is a fusion polypeptide comprising the Golgi localization domain of a heterologous Golgi resident polypeptide. Specifically, such host cell expression systems may be engineered to comprise a recombinant nucleic acid molecule encoding a polypeptide having GnTIII, operatively linked to a constitutive or regulated promoter system.

In one specific embodiment, the present invention provides a host cell that has been engineered to express at least one nucleic acid encoding a fusion polypeptide having GnTIII activity and comprising the Golgi localization domain of a heterologous Golgi resident polypeptide. In one aspect, the host cell is engineered with a nucleic acid molecule comprising at least one gene encoding a fusion polypeptide having GnTIII activity and comprising the Golgi localization domain of a heterologous Golgi resident polypeptide.

Generally, any type of cultured cell line, including the cell lines discussed above, can be used as a background to engineer the host cell lines of the present invention. In a preferred embodiment, CHO cells, BHK cells, NS0 cells, SP2/0 cells, YO myeloma cells, P3X63 mouse myeloma cells, PER cells, PER.C6 cells or hybridoma cells, other mammalian cells, yeast cells, insect cells, or plant cells are used as the background cell line to generate the engineered host cells of the invention.

The invention is contemplated to encompass any engineered host cells expressing a polypeptide having glycosyltransferase activity, e.g., GnTIII activity, including a fusion polypeptide that comprises the Golgi localization domain of a heterologous Golgi resident polypeptide as defined herein.

One or several nucleic acids encoding a polypeptide having glycosyltransferase activity, e.g., GnTIII activity, may be expressed under the control of a constitutive promoter or, alternately, a regulated expression system. Such systems are well known in the art, and include the systems discussed above. If several different nucleic acids encoding fusion polypeptides having glycosyltransferase activity, e.g., GnTIII activity, and comprising the Golgi localization domain of a heterologous Golgi resident polypeptide are comprised within the host cell system, some of them may be expressed under the control of a constitutive promoter, while others are expressed under the control of a regulated promoter. Expression levels of the fusion polypeptides having glycosyltransferase activity, e.g., GnTIII activity, are determined by methods generally known in the art, including Western blot analysis, Northern blot analysis, reporter gene expression analysis or measurement of glycosyltransferase activity, e.g., GnTIII activity. Alternatively, a lectin may be employed which binds to biosynthetic products of the GnTIII, for example, E4-PHA lectin. Alternatively, a functional assay which measures the increased Fc receptor binding or increased effector function mediated by antibodies produced by the cells engineered with the nucleic acid encoding a polypeptide with glycosyltransferase activity, e.g., GnTIII activity, may be used.

The host cells which contain the coding sequence of an antibody of the invention and which express the biologically active gene products may be identified by at least four general approaches: (a) DNA-DNA or DNA-RNA hybridization; (b) the presence or absence of "marker" gene functions; (c) assessing the level of transcription as measured by the expression of the respective mRNA transcripts in the host cell; and (d) detection of the gene product as measured by immunoassay or by its biological activity.

In the first approach, the presence of the coding sequence of an anti-MCSP antibody and/or the coding sequence of the polypeptide having glycosyltransferase (e.g., GnTIII) activity can be detected by DNA-DNA or DNA-RNA hybridization using probes comprising nucleotide sequences that are homologous to the respective coding sequences, respectively, or portions or derivatives thereof.

In the second approach, the recombinant expression vector/host system can be identified and selected based upon the presence or absence of certain "marker" gene functions (e.g., thymidine kinase activity, resistance to antibiotics, resistance to methotrexate, transformation phenotype, occlusion body formation in baculovirus, etc.). For example, if the coding sequence of the antibody of the invention, or a fragment thereof, and/or the coding sequence of the polypeptide having glycosyltransferase (e.g., GnTIII) activity are inserted within a marker gene sequence of the vector, recombinants containing the respective coding sequences can be identified by the absence of the marker gene function. Alternatively, a marker gene can be placed in tandem with the coding sequences under the control of the same or different promoter used to control the expression of the coding sequences. Expression of the marker in response to induction or selection indicates expression of the coding sequence of the antibody of the invention and/or the coding sequence of the polypeptide having glycosyltransferase (e.g., GnTIII) activity.

In the third approach, transcriptional activity for the coding region of the antibody of the invention, or a fragment thereof, and/or the coding sequence of the polypeptide having glycosyltransferase (e.g., GnTIII) activity can be assessed by hybridization assays. For example, RNA can be isolated and analyzed by Northern blot using a probe homologous to the coding sequences of the antibody of the invention, or a fragment thereof, and/or the coding sequence of the polypeptide having glycosyltransferase (e.g., GnTIII) activity or particular portions thereof. Alternatively, total nucleic acids of the host cell may be extracted and assayed for hybridization to such probes.

In the fourth approach, the expression of the protein products can be assessed immunologically, for example by Western blots, immunoassays such as radioimmuno-precipitation, enzyme-linked immunoassays and the like. The ultimate test of the success of the expression system, however, involves the detection of the biologically active gene products.

c) Fc region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

One accepted in vitro ADCC assay is as follows:
1) the assay uses target cells that are known to express the target antigen recognized by the antigen-binding region of the antibody;
2) the assay uses human peripheral blood mononuclear cells (PBMCs), isolated from blood of a randomly chosen healthy donor, as effector cells;
3) the assay is carried out according to following protocol:
i) the PBMCs are isolated using standard density centrifugation procedures and are suspended at $5 \times 10^6$ cells/ml in RPMI cell culture medium;
ii) the target cells are grown by standard tissue culture methods, harvested from the exponential growth phase with a viability higher than 90%, washed in RPMI cell culture medium, labeled with 100 micro-Curies of 51Cr, washed twice with cell culture medium, and resuspended in cell culture medium at a density of $10^5$ cells/ml;
iii) 100 microliters of the final target cell suspension above are transferred to each well of a 96-well microtiter plate;
iv) the antibody is serially-diluted from 4000 ng/ml to 0.04 ng/ml in cell culture medium and 50 microliters of the resulting antibody solutions are added to the target cells in the 96-well microtiter plate, testing in triplicate various antibody concentrations covering the whole concentration range above;
v) for the maximum release (MR) controls, 3 additional wells in the plate containing the labeled target cells, receive 50 microliters of a 2% (V/V) aqueous solution of non-ionic detergent (Nonidet, Sigma, St. Louis), instead of the antibody solution (point iv above);
vi) for the spontaneous release (SR) controls, 3 additional wells in the plate containing the labeled target cells, receive 50 microliters of RPMI cell culture medium instead of the antibody solution (point iv above);
vii) the 96-well microtiter plate is then centrifuged at 50×g for 1 minute and incubated for 1 hour at 4° C.;
viii) 50 microliters of the PBMC suspension (point i above) are added to each well to yield an effector:target cell ratio of 25:1 and the plates are placed in an incubator under 5% CO2 atmosphere at 37° C. for 4 hours;
ix) the cell-free supernatant from each well is harvested and the experimentally released radioactivity (ER) is quantified using a gamma counter;
x) the percentage of specific lysis is calculated for each antibody concentration according to the formula (ER−MR)/(MR−SR)×100, where ER is the average radioactivity quantified (see point ix above) for that antibody concentration, MR is the average radioactivity quantified (see point ix above) for the MR controls (see point v above), and SR is the average radioactivity quantified (see point ix above) for the SR controls (see point vi above);
4) "increased ADCC" is defined as either an increase in the maximum percentage of specific lysis observed within the antibody concentration range tested above, and/or a reduction in the concentration of antibody required to achieve one half of the maximum percentage of specific lysis observed within the antibody concentration range tested above. The increase in ADCC is relative to the ADCC, measured with the above assay, mediated by the same antibody, produced by the same type of host cells, using the same standard production, purification, formulation and storage methods, which are known to those skilled in the art, but that has not been produced by host cells engineered to overexpress GnTIII.

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. No. 5,648,260; U.S. Pat. No. 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816,567. In one embodiment, isolated nucleic acid encoding an anti-MCSP antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-MCSP antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-MCSP antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in *Mather, Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383: 44-68 (1982); MRC 5 cells; and FS4 cells. Other useful mammalian host cell lines include Chinese hamster ovary (CHO) cells, including DHFR⁻ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J.), pp. 255-268 (2003).

C. Assays

Anti-MCSP antibodies provided herein may be identified, screened for, or characterized for their physical/chemical properties and/or biological activities by various assays known in the art.

1. Binding Assays and Other Assays

In one aspect, an antibody of the invention is tested for its antigen binding activity, e.g., by known methods such as ELISA, Western blot, etc.

In another aspect, competition assays may be used to identify an antibody that competes with the anti-MCSP antibodies described herein for binding to MCSP. In certain embodiments, such a competing antibody binds to the same epitope (e.g., a linear or a conformational epitope) that is bound by the anti-MCSP antibodies described herein. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In an exemplary competition assay, immobilized MCSP is incubated in a solution comprising a first labeled antibody that binds to MCSP and a second unlabeled antibody that is being tested for its ability to compete with the first antibody for binding to MCSP. The second antibody may be present in a hybridoma supernatant. As a control, immobilized MCSP is incubated in a solution comprising the first labeled antibody but not the second unlabeled antibody. After incubation under conditions permissive for binding of the first antibody to MCSP, excess unbound antibody is removed, and the amount of label associated with immobilized MCSP is measured. If the amount of label associated with immobilized MCSP is substantially reduced in the test sample relative to the control sample, then that indicates that the second antibody is competing with the first antibody for binding to MCSP. See Harlow and Lane (1988) *Antibodies: A Laboratory Manual* ch. 14 (Cold Spring Harbor Laboratory, Cold Spring Harbor, N.Y.).

2. Activity Assays

In one aspect, assays are provided for identifying anti-MCSP antibodies thereof having biological activity. Antibodies having such biological activity in vivo and/or in vitro are also provided.

In certain embodiments, an antibody of the invention is tested for such biological activity.

D. Immunoconjugates

The invention also provides immunoconjugates comprising an anti-MCSP antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770, 701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S),

*momordica charantia* inhibitor, curcin, crotin, sapaonaria officinalis inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

E. Methods and Compositions for Diagnostics and Detection

In certain embodiments, any of the anti-MCSP antibodies provided herein is useful for detecting the presence of MCSP in a biological sample. In particular, the LC007 antibody was determined to recognize MCSP on Western blots as well as on fresh frozen and fixed tissue indicating that this antibody, and variants thereof that recognize the same epitope as LC007, is a suitable antibody for various techniques for detecting the presence of MCSP. The term "detecting" as used herein encompasses quantitative or qualitative detection.

In one embodiment, an anti-MCSP antibody for use in a method of diagnosis or detection is provided. In a further aspect, a method of detecting the presence of MCSP in a biological sample is provided. In certain embodiments, the method comprises contacting the biological sample with an anti-MCSP antibody as described herein under conditions permissive for binding of the anti-MCSP antibody to MCSP, and detecting whether a complex is formed between the anti-MCSP antibody and MCSP. Such method may be an in vitro or in vivo method. In one embodiment, the method is an immunohistochemistry (IHC) based assay. MCSP IHC assays, in general, involve contacting an anti-MCSP antibody with a tissue sample under conditions permissive for binding of the anti-MCSP antibody to MCSP, and detecting whether a complex is formed between the anti-MCSP antibody and MCSP. The presence or absence of the antibody-MCSP antigen complex can be detected by any immunodetection method known in the art, including fluorescence, immunogold, or enzyme-mediated staining methods. The analysis can be performed on fresh tissue samples or on samples that have been frozen or fixed (for example, formalin-fixed, paraffin-embedded tissues (FFPET). See for example, Miller et al., Fixation and epitope retrieval in diagnostic immunohistochemistry: a concise review with practical considerations. Appl. Immunohistochem. Mol. Morphol. (2000) 8(3): 228-235.

In one embodiment, an anti-MCSP antibody is used to select subjects eligible for therapy with an anti-MCSP antibody, e.g. where MCSP is a biomarker for selection of patients.

Exemplary disorders that may be diagnosed using an antibody of the invention include disorders characterized by expression of MCSP, including cell proliferative disorders or angiogenic disorders. In one embodiment, the disorder is a cancer, such as a skin cancer (including melanoma and basel cell carcinomas), gliomas (including glioblastomas), bone cancer (such as osteosarcomas), and leukemia (including ALL and AML).

In certain embodiments, labeled anti-MCSP antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

F. Pharmaceutical Formulations

Pharmaceutical formulations of an anti-MCSP antibody as described herein are prepared by mixing such antibody having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredients as necessary for the particular indication being treated, preferably those with complementary activities that do not adversely affect each other. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Methods and Compositions

Any of the anti-MCSP antibodies provided herein may be used in therapeutic methods.

In one aspect, an anti-MCSP antibody for use as a medicament is provided. In further aspects, an anti-MCSP antibody for use in treating cancer is provided. In certain embodiments, an anti-MCSP antibody for use in a method of treatment is provided. In certain embodiments, the invention provides an anti-MCSP antibody for use in a method of treating an individual having cancer comprising administering to the individual an effective amount of the anti-MCSP antibody. In one such embodiment, the method further comprises administering to the individual an effective amount of at least one additional therapeutic agent, e.g., as described below. In further embodiments, the invention provides an anti-MCSP antibody for use in treating melanoma. An "individual" according to any of the above embodiments is preferably a human.

In a further aspect, the invention provides for the use of an anti-MCSP antibody in the manufacture or preparation of a medicament. In one embodiment, the medicament is for treatment of cancer. In a further embodiment, the medicament is for use in a method of treating cancer comprising administering to an individual having cancer an effective amount of the medicament. In one such embodiment, the method further comprises administering to the individual an effective amount of at least one additional therapeutic agent, e.g., as described below. An "individual" according to any of the above embodiments may be a human.

In a further aspect, the invention provides a method for treating cancer. In one embodiment, the method comprises administering to an individual having such cancer an effective amount of an anti-MCSP antibody. In one such embodiment, the method further comprises administering to the individual an effective amount of at least one additional therapeutic agent, as described below. An "individual" according to any of the above embodiments may be a human.

In one embodiment, the cancer in the above aspects, expresses MCSP on the surface of its constituent cells. In one embodiment, the cancer in the above aspects is selected from among skin cancer (including melanoma and basel cell carcinomas), gliomas (including glioblastomas), bone cancer (such as osteosarcomas), and leukemia (including ALL and AML). In one embodiment, the cancer in the above aspects is melanoma.

In a further aspect, the invention provides pharmaceutical formulations comprising any of the anti-MCSP antibodies provided herein, e.g., for use in any of the above therapeutic methods. In one embodiment, a pharmaceutical formulation comprises any of the anti-MCSP antibodies provided herein and a pharmaceutically acceptable carrier. In another embodiment, a pharmaceutical formulation comprises any of the anti-MCSP antibodies provided herein and at least one additional therapeutic agent, e.g., as described below.

Antibodies of the invention can be used either alone or in combination with other agents in a therapy. For instance, an antibody of the invention may be co-administered with at least one additional therapeutic agent.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent and/or adjuvant. Antibodies of the invention can also be used in combination with radiation therapy.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. The progress of this therapy is easily monitored by conventional techniques and assays.

It is understood that any of the above formulations or therapeutic methods may be carried out using an immunoconjugate of the invention in place of or in addition to an anti-MCSP antibody.

H. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-MCSP antibody.

EXAMPLES

The following are examples of methods and compositions of the invention. It is understood that various other embodiments may be practiced, given the general description provided above.

Example 1

Generation of Anti-MCSP Antibodies

Immunization and Hybridoma Generation

Balb/c mice were immunized i.p. with a synthetic peptide corresponding to aa 2177-2221 of the human MCSP sequence coupled to KLH (SVPE AARTEAGKPE SSTPT-GEPGPMASSPEPAVA KGGFLSFLEAN (SEQ ID NO: 2)) every 4 weeks for 4 times followed by two immunizations with Colo38 cells (Giacomini P, Natali P, Ferrone S J Immunol. 1985 July; 135(1):696-702) expressing MCSP. The initial immunization was performed in CFA, all following boosts in IFA.

Serum test bleeds were taken and half-maximal serum titer was determined using the MCSP peptide aa2177-2221 coupled to biotin and coated onto Streptavidin ELISA microtiter plates. Mice with a half-maximal titer of 1:50,000 were selected for i.v. boost. An i.v. boost on day 4 before fusion was performed using 20 µg of the MCSP peptide and Colo38 cells. Three days following the i.v. boost, splenocytes were harvested, and fused with Ag8 myeloma cells.

Screening and Hybridoma Characterization

Screening for MCSP specific antibodies was started by identifying antibodies binding to MCSP-biotin peptide aa 2177-2221 (SEQ ID NO: 2) coated onto streptavidin microtiter plates. Positive clones binding to immobilized MCSP peptide were then expanded in serum free medium (Hyclone ADCF-Mab-Thermo Scientific, Cat. No. SH30349.02).

Binding to the native form of MCSP was performed by FACS analysis on Colo38 cells naturally overexpressing high levels of human MCSP. The prostate carcinoma line PC3 that does not express detectable levels of MCSP was used as negative control. To further characterize the specificity of the lead antibodies, double immunocytochemistry analysis was performed on Colo38 cells using an established commercial anti-MCSP antibody (Invitrogen Corp., Catalog No. 41-2000, Clone LHM2) for doublestaining in combination with chimeric lead antibodies (expressing human Fc). As shown by immunofluorescence labeling, one antibody, LC007, strongly stained surface MCSP in Colo38 cells, but was negative on PC3 cells.

Example 2

Chimerization mRNA was isolated from the hybridoma cell line expressing antibody clone LC007 and converted into cDNA using commercial available kits. The cDNA isolates for heavy (SEQ ID NO: 39) and light chain (SEQ ID NO: 38) were sequenced and each segment was fused to the constant regions of human IgG1 and kappa.

Sequences were expressed, using signal peptides from human immunoglobulins, in HEK-EBNA cells, and purified using conventional proteinA and size exclusion chromatography (SEC).

Figure 2:
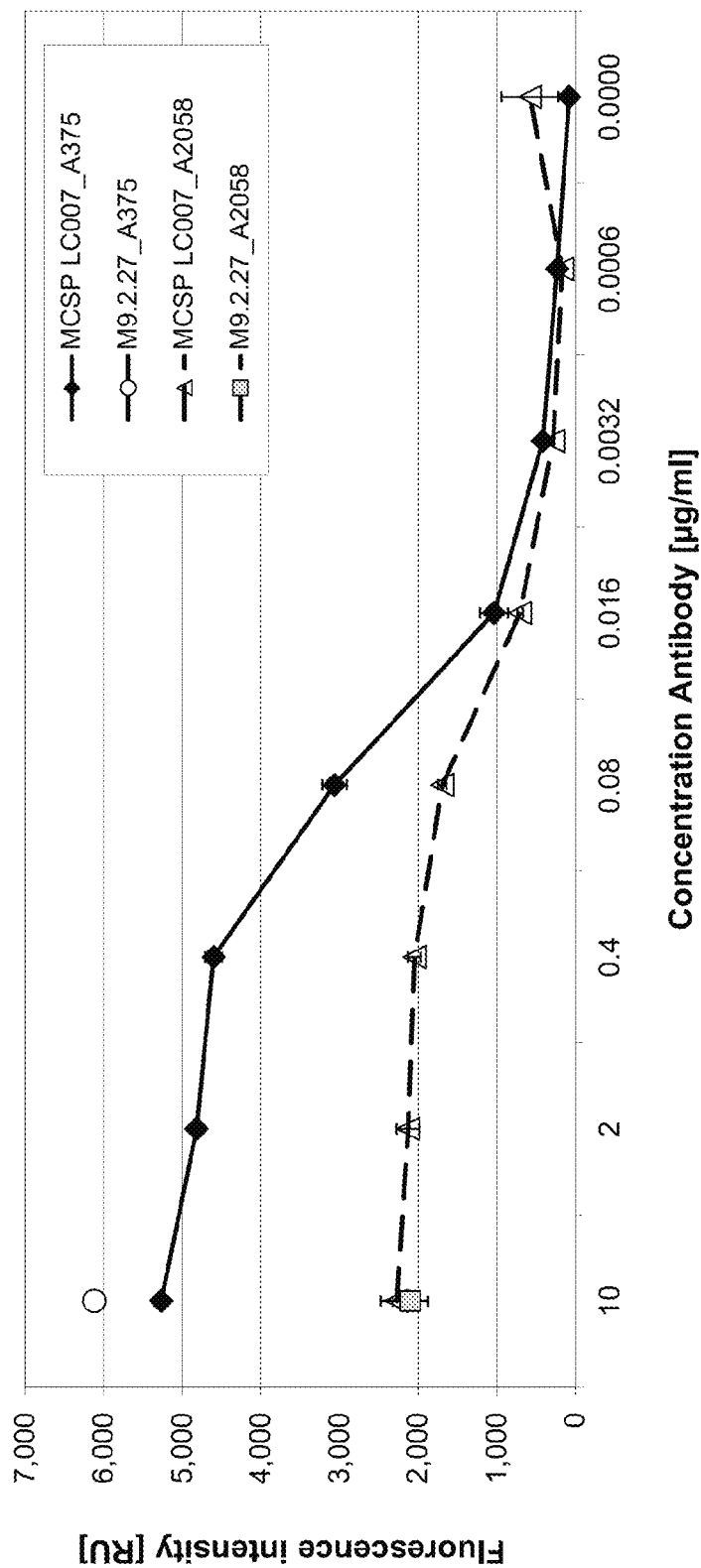
FIG. 2 is a graph depicting the results of a FACs assay showing binding affinity of chimeric antibody LC007 for surface MCSP in A2058 and A375 cancer cells.

Binding activity was determined by the following method. Target cells were detached from culture flask with cell dissociation buffer, counted and checked for viability. Cells were resuspended and adjusted to $1.111 \times 10^6$ (viable) cells/ml in PBS-0.1% BSA. 180 μl of this suspension were transferred to each well (200,000 cells/well) in a round bottom 96-well-plate, centrifuged for 4 min, at 400 g, and resuspended. 20 μl of antibody dilutions in PBS-0.1% BSA (from 10 μg/ml to 0.002 μg/ml) were added to each well. The samples were centrifuged for 4 min, at 400 g, and resuspended. Secondary antibody, FITC-conjugated AffiniPure F(ab')2 fragment goat anti-human IgG Fcg Fragment Specific (Jackson Immuno Research Lab #109-096-098)), was added and the sample centrifuged for 4 min, at 400 g, and resuspended. Fluorescence was measured in flow cytometer (e.g. FACS Canto II). Results of titration are shown in FIGS. 1 and 2. Antibody 9.2.27, described in Morgan A C Jr, Galloway D R, Reisfeld R A. Hybridoma. 1981; 1(1):27-36; GenBank Accession Numbers: GI:20797193 and GI:20797189 for light and heavy chain respectively, was used as a reference (FIG. 2). Human melanoma cell-lines Colo38, A2058, and A375 were used. Giacomini et al. 1985 (for Colo38). Marquardt H, Todaro G J. J Biol Chem. 1982 May 10; 257(9):5220-5 (for A2058). Geiser M, Schultz D, Le Cardinal A, Voshol H, García-Echeverría C. Cancer Res. 1999 Feb. 15; 59(4):905-10 (for A375).

Example 3

Determination of Binding Epitope of LC007 Antibody on MCSP Antigen

The LC007 antibody showed good binding on melanoma cells, but only weak binding on the original immunogen. Therefore, an epitope mapping of antibody LC007 was undertaken in order to determine the exact binding site on the antigen. For this several truncated versions of the MCSP antigen were generated, each containing varying numbers of the membrane proximal repeat region of human MCSP, referred to as the CSPG repeat. Staub E., et al., FEBS Lett. 527:114-118 (2002).

Figure 4:
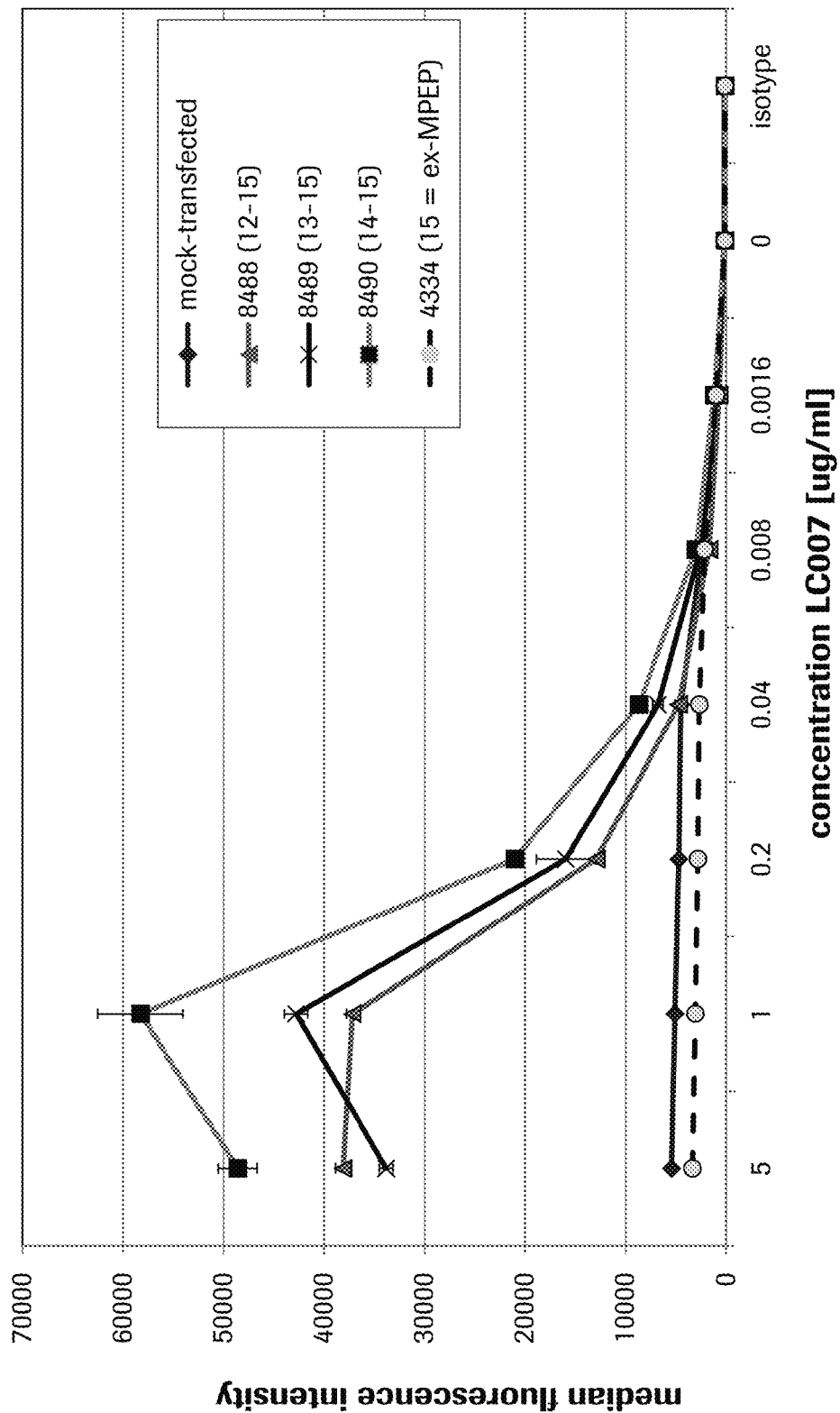
FIG. 4 is a graph showing binding specificity of LC007 for MCSP CSPG repeat constructs.

Construct 1 contained CSPG repeat 15 (SEQ ID NO: 4), Construct 2 contained CSPG repeat 14-15 (SEQ ID NO: 5), Construct 3 contained CSPG repeat 13-15 (SEQ ID NO: 6), and Construct 4 contained CSPG repeat 12-15 (SEQ ID NO: 7). FIG. 3 provides a schematic of the CSPG repeat containing structure of MCSP. These constructs contained the original transmembrane region and were expressed on HEK-EBNA cells for detection of LC007 binding by FACS. FIG. 4 shows the outcome of this experiment. The construct including only the MCSP repeat 15 and the natural transmembrane domain did not show any significant binding. In contrast, all constructs including domains 14 and 15 showed significant binding. This indicates that the binding epitope either is within repeat 14, or is only reconstituted when repeat 14 is present and potentially includes also parts of repeat 15 or the unstructured region between the CSPG repeats and the transmembrane domain.

It was also determined that LC007 recognizes MCSP on Western blots (denatured, linear epitope) as well as on fresh frozen and fixed tissue. Western blot analysis also showed that LC007 recognizes MCSP fragments and glycosylation variants, but no proteins on MCSP negative cell lines. As such, the LC007 antibody is a suitable antibody for various techniques for detecting the presence of MCSP, including immunohistochemistry (IHC) based analysis, such as formalin-fixed, paraffin-embedded tissues (FFPET) IHC analysis.

Example 4

Determination of Crossreactivity with Human and Cynomolgus Antigen

Figure 5:
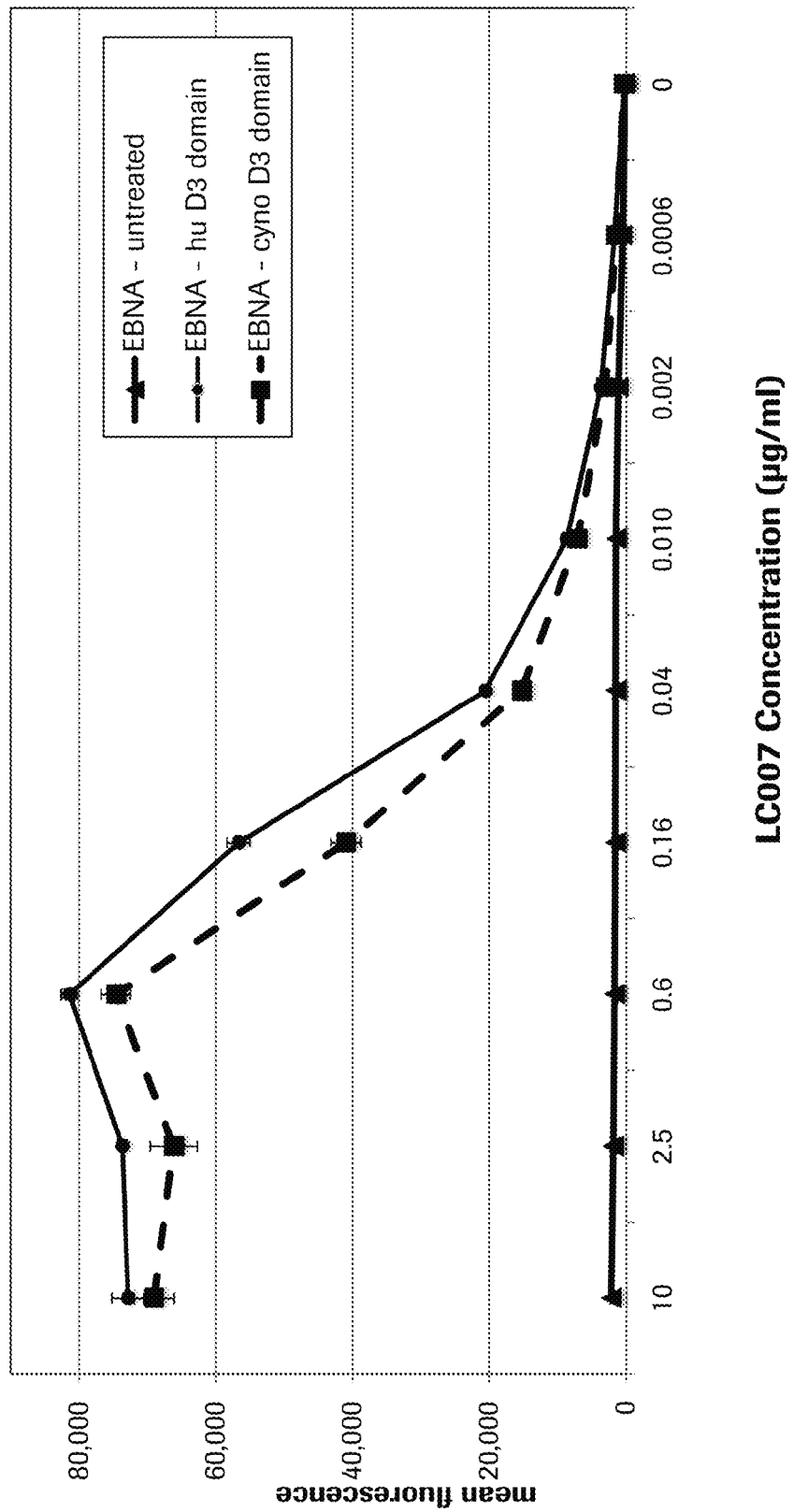
FIG. 5 is a graph depicting the results of a FACs assay showing that antibody LC007 binds with similar affinity to the cynomolgus construct as to the corresponding human expression construct.

An expression construct was generated that included the C-terminal part of the cynomolgus MCSP protein, a signal peptide for secretion and a N-terminal FLAG-tag (SEQ ID NO: 8) to test for crossreactivity towards the cynomolgus antigen. This domain was referred to as the D3 domain Tillet, F. et. Al, J. Biol. Chem. 272: 10769-10776 (1997). A similar construct was done for the human counterpart (SEQ ID NO: 9). An expression plasmid encoding for these two construct was electroporated into HEK-EBNA cells, and expression was confirmed with an anti-FLAG antibody. Binding of LC007 antibody was then tested by flow cytometry. FIG. 5 shows that antibody LC007 binds with similar affinity to the cynomolgus construct as to the corresponding human expression construct.

Example 5

Glycoengineered LC007 Antibody

Glycoengineered variants of the LC007 antibody were produced by co-transfection of the antibody expression vectors together with a GnT-III glycosyltransferase expression vector, or together with a GnT-III expression vector plus a Golgi mannosidase II expression vector.

Example 6

ADCC of Glycoengineered LC007 Antibody

ADCC Assay

Figure 6:
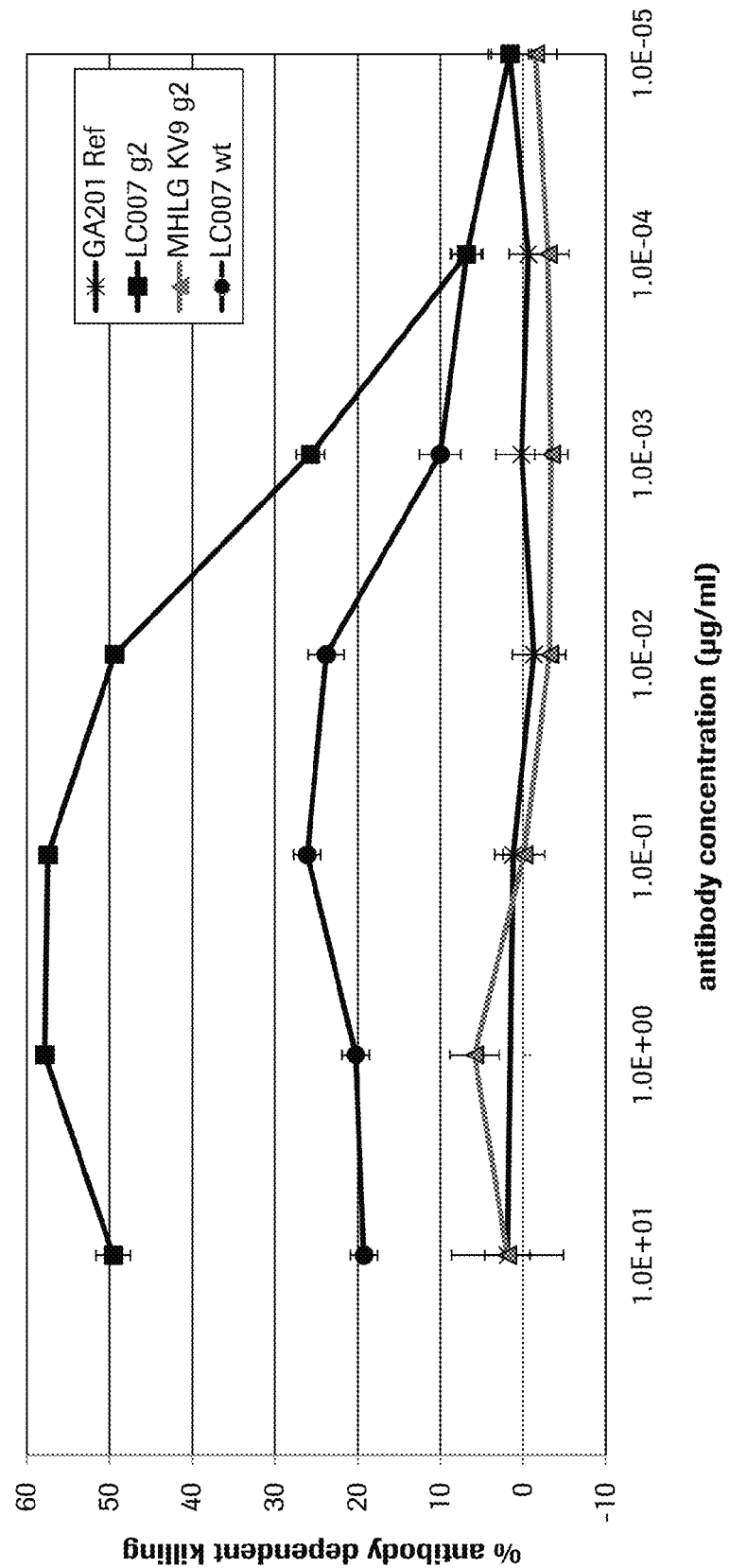
FIG. 6 is a graph showing the ADCC effect of both the non-glycoengineered and glycoengineered LC007 antibody.

Lysis of Colo38 human malignant melanoma cells (target) by human lymphocytes (effector), at a target:effector ratio of 1:19, during a 16 h incubation at 37° C. in the presence of different concentrations of the glycoengineered LC007 antibody and control antibody samples, was measured via retention of a fluorescent dye. Kolber et al, 1988, J. Immunol. Methods 108: 255-264. IMR-32 cells were labeled with the fluorescent dye Calcein AM for 20 min (final concentration 3.3 μM). The labeled cells (80,000 cells/well) were incubated for 1 h with different concentrations of the glycoengineered LC007 antibody and control antibody samples. Then, monocyte depleted mononuclear cells were added (1,500,000 cells/well) and the cell mixture was incubated for 16 h at 37° C. in a 5% $CO_2$ atmosphere. The supernatant was discarded and the cells were washed once with HBSS and lysed in Triton X-100 (0.1%). Retention of the fluorescent dye in Colo38 cells was measured with a fluorometer (Perkin Elmer, Luminscence Spectrometer LS 50B, (Foster City, Calif.) and specific lysis was calculated relative to a total lysis control, resulting from exposure of the target to a detergent instead of exposure to antibody. The signal in the absence of antibody was set to 0% cytotoxicity. Each antibody concentration was analyzed by triplicate, and the assay was repeated three separate times. As shown in FIG. 6, the non-glycoengineered LC007 antibody (LC007 wt) exhibited an ADCC effect. The glycoengineered LC007 antibody (LC007 g2) showed increased ADCC as compared to the non-glycoengineered LC007. Thus, the non-glycoengineered LC007 antibody per se shows some ADCC activity, which can further be enhanced by glycoengineering. In contrast, anti-MCSP antibody MHLG KV9 G2, which is a humanized version of antibody 225.28S described in Buraggi G, et al. Int J Biol Markers. 1986 January-April; 1(1):47-54), did not show any significant ADCC induction in this assay. The binding epitope of the 225.28 antibody was determined to be within the N-terminal part, or membrane distal portion, of the MCSP antigen. The glycoengineered GA201 antibody that binds to the EGF Receptor, which is absent on the Colo38 cells, was included as a control. Absence of ADCC with this antibody shows that activation of NK cells must occur via the target present on the tumor cell.

Figure 7:
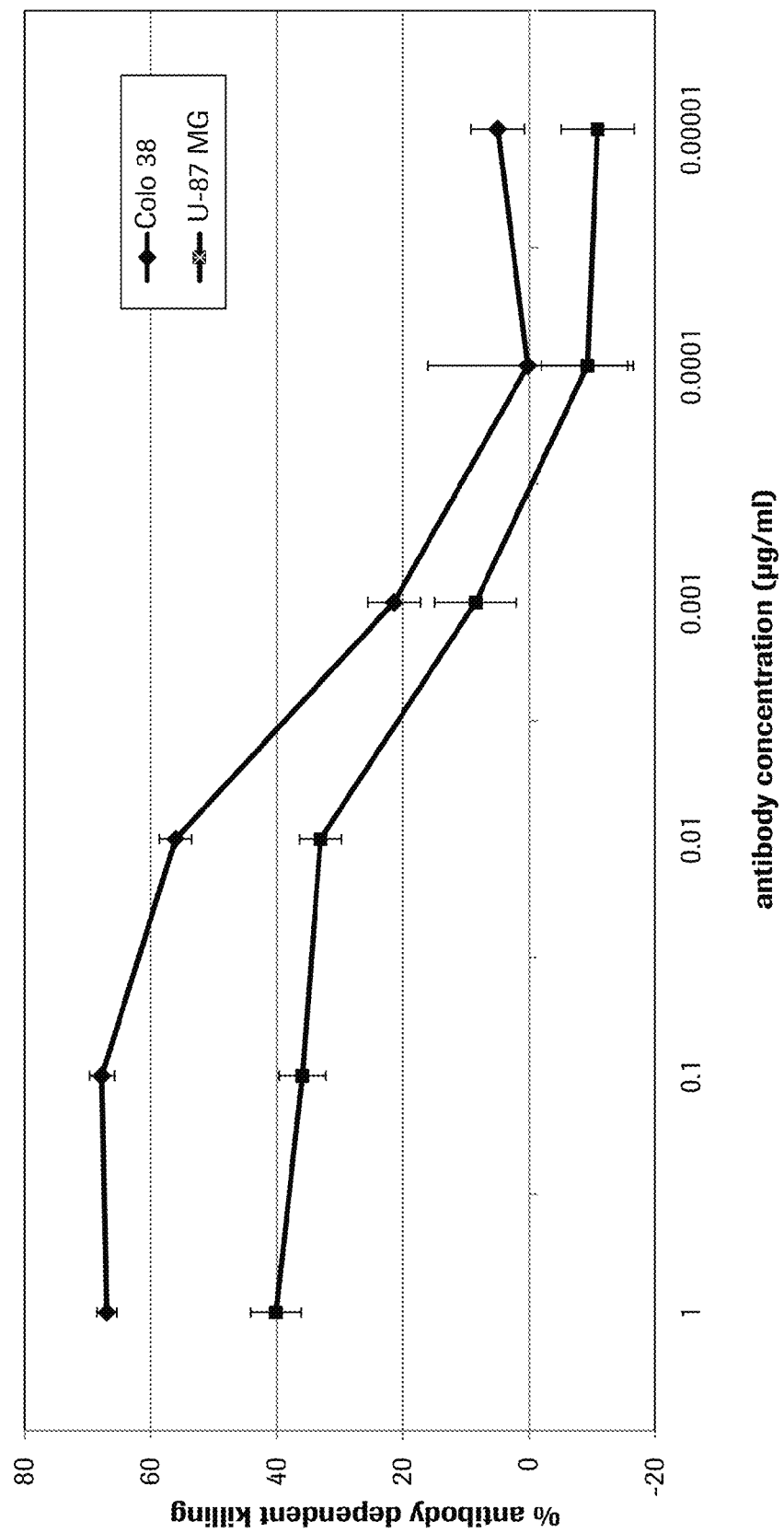
FIG. 7 is a graph showing that the ADCC effect of the glycoengineered LC007 antibody is observed in the human U86MG glioblastoma cell-line.

FIG. 7 shows the ADCC of the glycoengineered LC007 antibody is observed also for the human U86MG glioblastoma cell-line.

Example 7

Humanization of Glycoengineered LC007 Antibody

The humanization procedure was done following the classical loop-grafting procedure (Jones P T, Dear P H, Foote J, Neuberger M S, Winter G. Nature. 1986 May 29-Jun. 4; 321(6069):522-5. P. Carter et al.; Proc. Natl. Acad. Sci. USA; Vol. 89, pp. 4285-4289, May 1992). In brief, the CDRs (SEQ ID NOs. 10, 11, 12, 14, 15, and 16) of the murine antibody were grafted onto the human framework sequences: IMGT Acc No. IGKV1D-39*01 and IGKJ1 for the light chain, and IMGT Acc No: IGHV4-31*02 and IGHJ4 for the heavy chain, resulting in an antibody that had a heavy chain comprising the amino acid sequence of SEQ ID NO: 29 and a light chain comprising the amino acid sequence of SEQ ID NO: 28.

Figure 8:
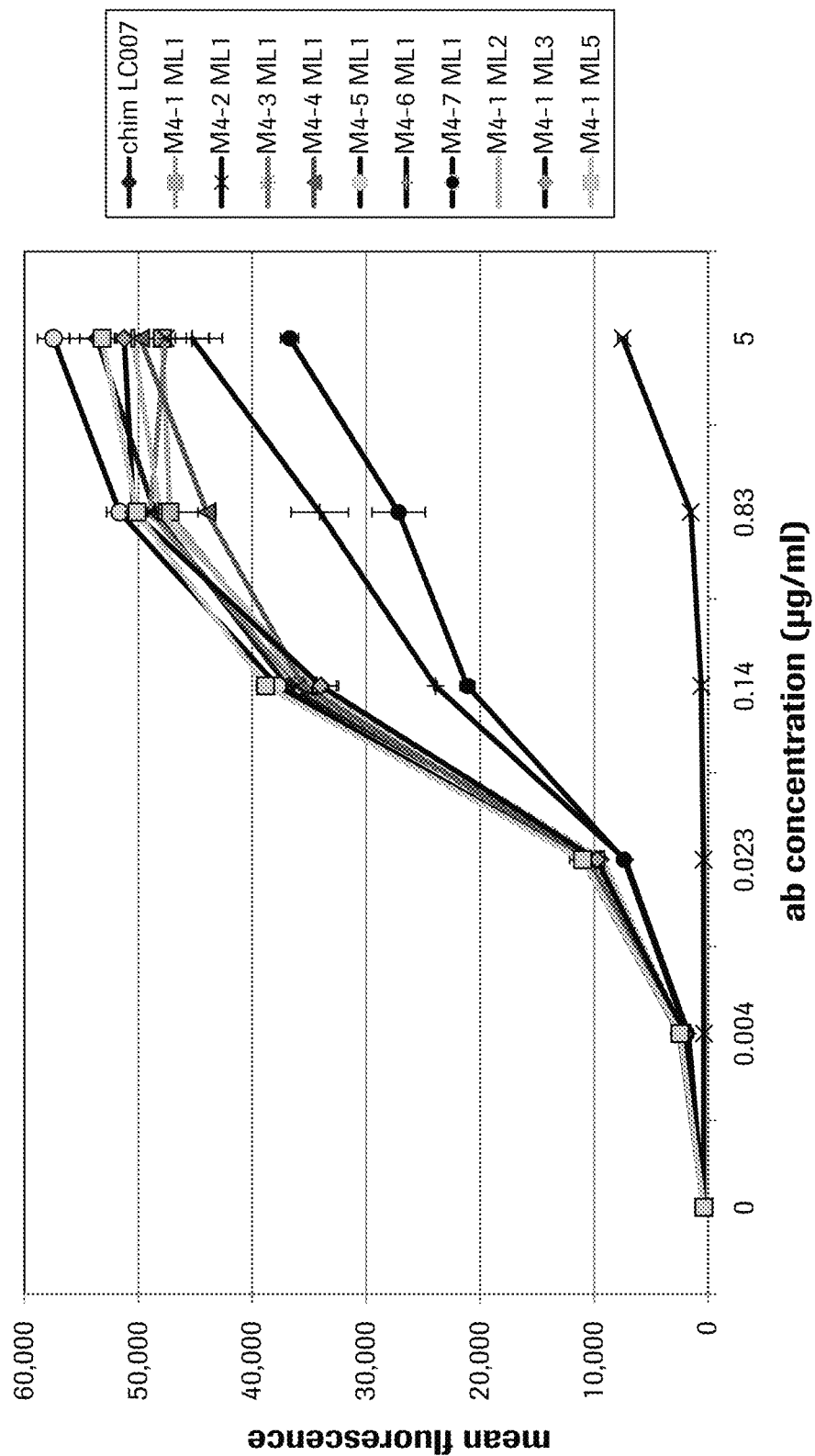
FIG. 8 is a graph showing the binding properties of several humanized variants of the LC007 antibody.

The antibody constructs were optimized to retain binding affinity to the target MCSP antigen. FIG. 8 shows the binding properties of the different humanized variants. The human residues Val71 and Arg94 were replaced by their corresponding murine counterparts, arginine and aspartic acid, respectively, as it was determined that antibody constructs with the human residues exhibited reduced binding to antigen. As shown in FIG. 8, the constructs M4-2 ML1, having a Arg at position 94 in the heavy chain (Kabat numbering) (SEQ ID NO: 30 (corresponding to D98R in this sequence)) and M4-6 ML1, having a Val at position 74 in the heavy chain (Kabat numbering) (SEQ ID NO: 33 (corresponding to R72V in this sequence)) showed reduced binding to the MCSP antigen, indicating the relevance of these residues to the binding specificity of the antibodies. Those constructs which had the corresponding murine counterparts, arginine and aspartic acid, in those positions respectively, retained binding activity, for example those antibodies having the heavy chain constructs of M4-1 (SEQ ID NO: 29) and M4-3 (SEQ ID NO: 32).

The CDR-H1 residue Asn35 was substituted towards the corresponding human germ-line serine residue. As shown in FIG. 8, construct M4-7 ML1 (SEQ ID NO: 25) which contains this substitution, showed a reduction in binding to the target MCSP antigen, indicating that this residue is also involved in retaining the antigen binding strength.

Additional constructs indicated the relevance of other residues in the binding properties of the anti-MCSP antibodies. Replacing the arginine residue with a serine at position 7 in HVR-L1 (SEQ ID NO: 21) resulted in a reduced binding activity for the MCSP antigen. Replacing the aspartic acid tyrosine with an aspartic acid at position 1 and replacing the alanine with threonine at position 2 of HVR-L2 SEQ ID NO: 21 also resulted in a reduced binding activity for the MCSP antigen.

The monovalent binding affinities for the chimeric LC007 and the humanized variant M4-3 ML2 were determined using a Biacore assay. Briefly, the antibodies were chemically immobilized on a CM5 chip (Biacore) via amine-coupling (activation with EDC-NHS, coupling of 5000 RU for each antibody, deactivation with ethanolamine). The recombinant D3 domain of MCSP was used as analyte. The experiment was performed at 25° and 37° in HBS-EP+ running buffer on a Biacore T100. A 1:2 dilution series of MCSP D3 (50 nM down to 1.56 nM) were injected over the chip surface for 240 s (association), followed by running buffer for 300 s (dissociation). The surface was regenerated between injections with 10 mM glycine pH 2 for 30 s. The sensorgrams were fitted with the 1:1 binding model (with RI=0 and Rmax=local) to determine the Kd.

The Kd for the chimeric LC007 antibody was determined to be 9.8 nM at 25° C. and 10.8 nM at 37° C. The Kd for the M4-3 ML2 antibody was determined to be 11.4 nM at 25° C. and 16.6 nM at 37° C.

Example 8

ADCC of Humanized Variants of Glycoengineered LC007 Antibody

ADCC activity for the humanized variants for the glycoengineered LC007 antibody was measured by lactate dehydrogenase using Colo38 cells as the target cells. Human peripheral blood mononuclear cells (PBMC) were used as effector cells and were prepared using Histopaque-1077 (Sigma Diagnostics Inc., St. Louis, Mo. 63178 USA) following essentially the manufacturer's instructions. In brief, venous blood was taken with heparinized syringes from healthy volunteers. The blood was diluted 1:0.75-1.3 with PBS (not containing $Ca^{++}$ or $Mg^{++}$) and layered on Histopaque-1077. The gradient was centrifuged at 400×g for 30 min at room temperature (RT) without breaks. The interphase containing the PBMC was collected and washed with PBS (50 ml per cells from two gradients) and harvested by centrifugation at 300.times.g for 10 minutes at RT. After resuspension of the pellet with PBS, the PBMC were counted and washed a second time by centrifugation at 200×g for 10 minutes at RT. The cells were then resuspended in the appropriate medium for the subsequent procedures.

The effector to target ratio used for the ADCC assays was 25:1 and 10:1 for PBMC and NK cells, respectively. The effector cells were prepared in AIM-V medium at the appropriate concentration in order to add 50 µl per well of round bottom 96 well plates. Target cells were Colo30 cells. Target cells were washed in PBS, counted and resuspended in AIM-V at 0.3 million per ml in order to add 30,000 cells in 100 µl per microwell. Antibodies were diluted in AIM-V, added in 50 µl to the pre-plated target cells and allowed to bind to the targets for 10 minutes at RT. Then the effector cells were added and the plate was incubated for 4 hours at 37° C. in a humidified atmosphere containing 5% CO2. Killing of target cells was assessed by measurement of lactate dehydrogenase (LDH) release from damaged cells using the Cytotoxicity Detection kit (Roche Diagnostics, Rotkreuz, Switzerland). After the 4-hour incubation the plates were centrifuged at 800×g. 100 µl supernatant from each well was transferred to a new transparent flat bottom 96 well plate. 100 µl color substrate buffer from the kit were added per well. The Vmax values of the color reaction were determined in an ELISA reader at 490 nm for at least 10 min using SOFTmax PRO software (Molecular Devices, Sunnyvale, Calif. 94089, USA). Spontaneous LDH release was measured from wells containing only target and effector cells but no antibodies. Maximal release was determined from wells containing only target cells and 1% Triton X-100. Percentage of specific antibody-mediated killing was calculated as follows: ((x−SR)/(MR−SR)*100, where x is the mean of Vmax at a specific antibody concentration, SR is the mean of Vmax of the spontaneous release and MR is the mean of Vmax of the maximal release.

Figure 9:
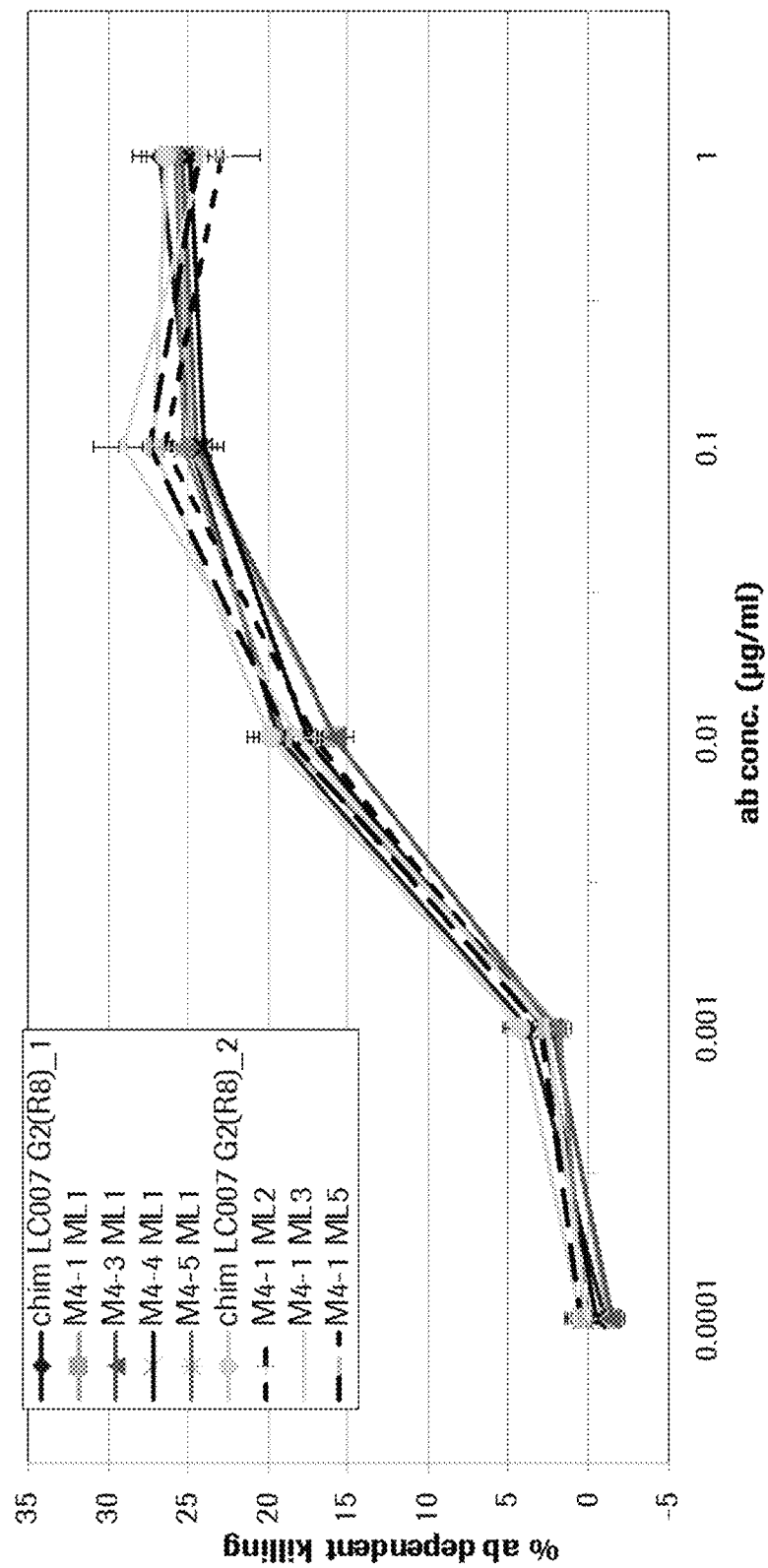
FIG. 9 is a graph showing that the humanized variants of LC007 retain the ADCC activity of the parent glycoengineered LC007 antibody.

FIG. 9 shows the results of this assay and confirms that the humanized variants retained the ADCC activity of the parent glycoengineered LC007 antibody.

Figure 10:
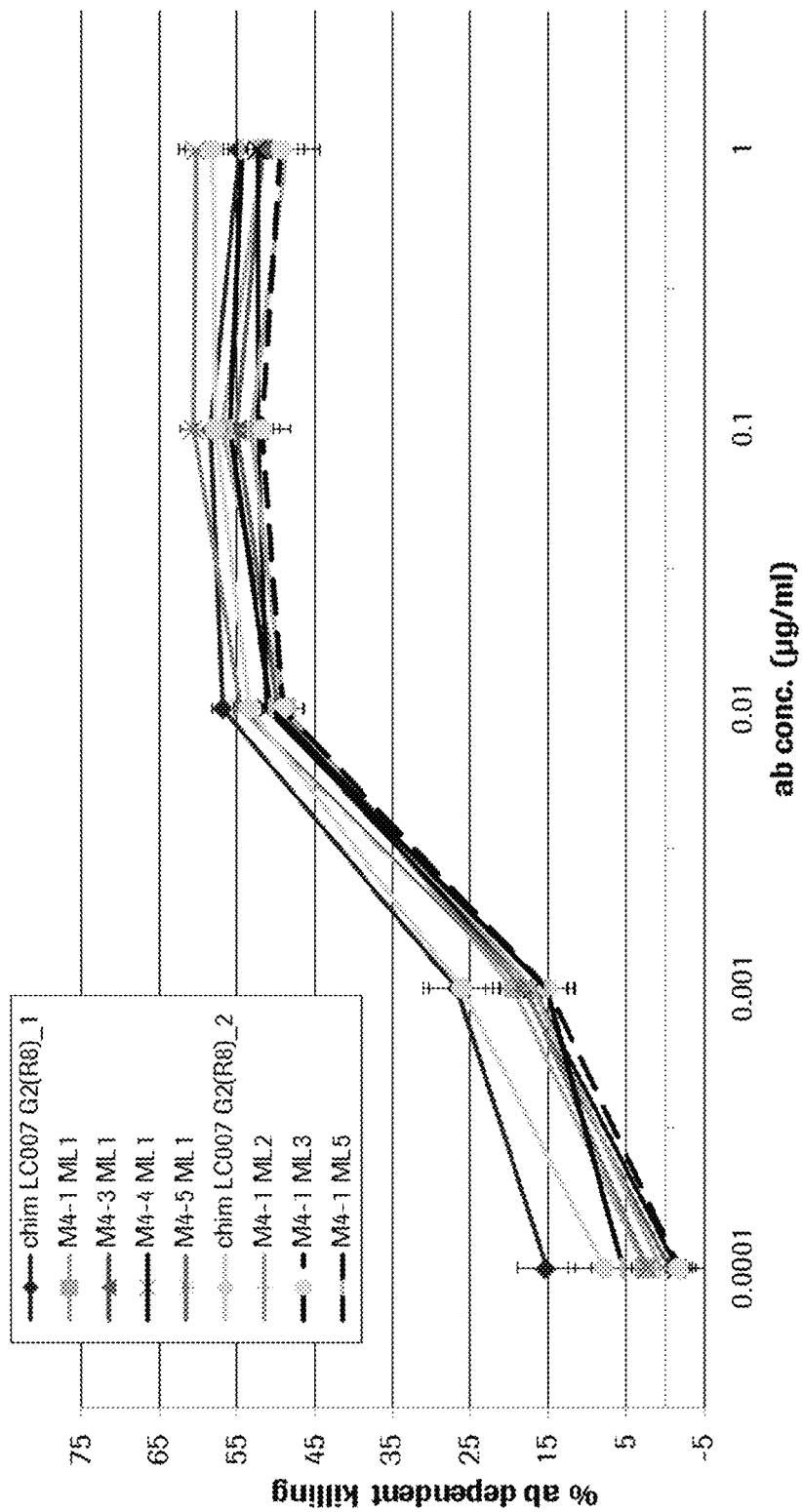
FIG. 10 is a graph showing that the humanized variants of LC007 retain the ADCC activity of the parent glycoengineered LC007 antibody.

The surviving target cells were further quantified by calcein measurement (Wallac Victor3 1420 Multilabel Counter) after washing and cell lysis using 5 mM borate Buffer containing 0.1% Triton X-100 using the assay as described in Example 6. The results of this assay are shown in FIG. 10.

Example 9

Mouse Xenograft Assays 9.1 MV3 Cells in FcgR3 Transgenic SCID Mice

20 FcgR3A tg SCID mice (purchased from Charles River, Lyon, France) were maintained under IVC (Isolated Ventilated Cages) conditions with daily cycles of 12 h light/12 h darkness according to committed guidelines (GV-Solas; Felasa; TierschG). Experimental study protocol was reviewed and approved by local government (P 2005086). After arrival animals were maintained for one week to get accustomed to new environment and for observation. Continuous health monitoring was carried out on regular basis.

MV3 tumor cell lines (van Muijen G N, et al., Int J Cancer. 48(1):85-91 (1991)). were routinely cultured in DMEM medium (GIBCO, Switzerland) supplemented with 10% fetal bovine serum (Invitrogen, Switzerland) at 37° C. in a water-saturated atmosphere at 5% CO2. Culture passage was performed with trypsin/EDTA 1× (GIBCO, Switzerland) splitting every third day. At day of injection, the tumor cells were harvested using trypsin-EDTA (Gibco, Switzerland) from culture flasks (Greiner Bio-One) and transferred into 50 ml culture medium, washed once and resuspended in AIM V (Gibco, Switzerland). After an additional washing with AIM V, cell concentration was determined using a cell counter. 0.2×10$^6$ cells in 200 ul of Aim V medium were injected into tail vein of each FcgR3A tg SCID mice.

Therapy

The xenograph mice were assigned to either a treatment group or a vehicle control group, each group consisting of nine mice. The treatment group was administered 25 mg/kg of the humanized glyco-engineered anti-MCSP mAb M4-3 ML2 intravenously. The vehicle control group was intravenously administered the vehicle only. Both groups received three doses, on day 7, 14, and 21.

Statistical analysis was performed on the data obtained from the therapy using a log-rank (Mantel-Cox) Test: p=0.0033 and Gehan-Breslow-Wilcoxon Test: p=0.0039.

Results

Figure 11:
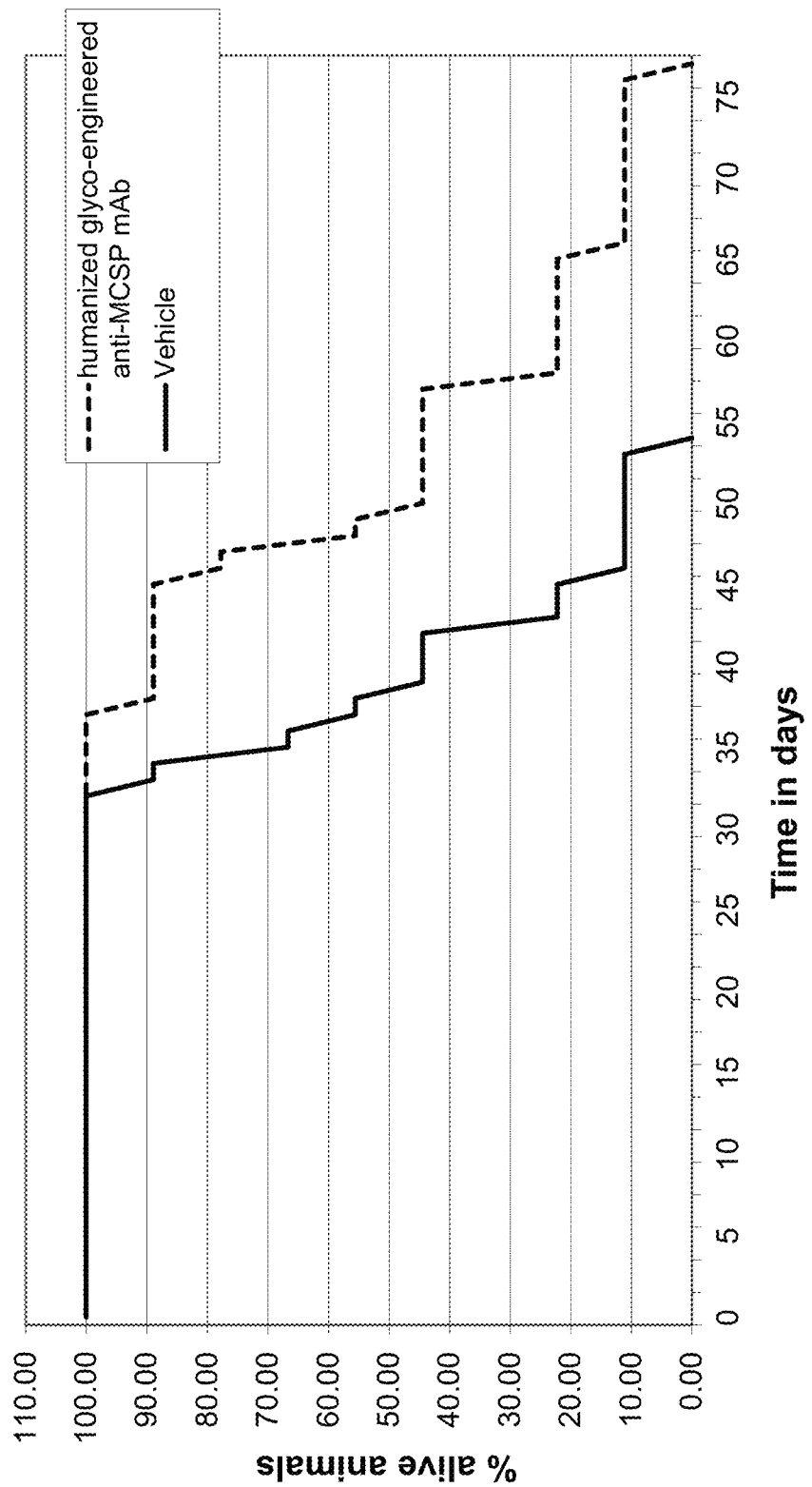
FIG. 11 depicts a survival curve showing that a humanized glyco-engineered anti-MCSP antibody significantly increases survival time in FcgR3A transgenic SCID mice harboring a MV3 tumor cell line as compared to the vehicle control.

As shown in FIG. 11, the humanized glyco-engineered anti-MCSP antibody significantly increases survival time in this model as compared to the vehicle control.

9.2 MDA-MB-435 Cells in FcgR3 Transgenic SCID Mice

MDA-MB435 cells were originally obtained from ATCC and after expansion deposited in the Glycart internal cell bank. MDA-MB435 tumor cell lines were routinely cultured in RPMI medium (GIBCO, Switzerland) supplemented with 10% fetal bovine serum (Invitrogen, Switzerland) and 1% Glutamax at 37° C. in a water-saturated atmosphere at 5% CO2. Culture passage was performed with trypsin/EDTA 1× (GIBCO, Switzerland) splitting every third day.

FcgR3A tg SCID mice (purchased from Charles River, Lyon, France) were maintained under IVC (Isolated Ventilated Cages) conditions with daily cycles of 12 h light/12 h darkness according to committed guidelines (GV-Solas; Felasa; TierschG). Experimental study protocol was reviewed and approved by local government (P 2005086). After arrival animals were maintained for one week to get accustomed to new environment and for observation. Continuous health monitoring was carried out on regular basis.

At day of injection, the tumor cells were harvested using trypsin-EDTA (Gibco, Switzerland) from culture flasks (Greiner Bio-One) and transferred into 50 ml culture medium, washed once and resuspended in AIM V (Gibco, Switzerland). After an additional washing with AIM V, cell concentration was determined using a cell counter. 0.2×10$^6$ cells in 200 ul of Aim V medium were injected into tail vein of each FcgR3A tg SCID mice.

Therapy

The xenograph mice were assigned to either a treatment group or a vehicle control group. The treatment group was administered 25 mg/kg of t chimeric glyco-engineered anti-MCSP mAb intravenously. The vehicle control group was intravenously administered the vehicle only. Both groups received three doses, on day 7, 14, and 21.

Results

Figure 12:
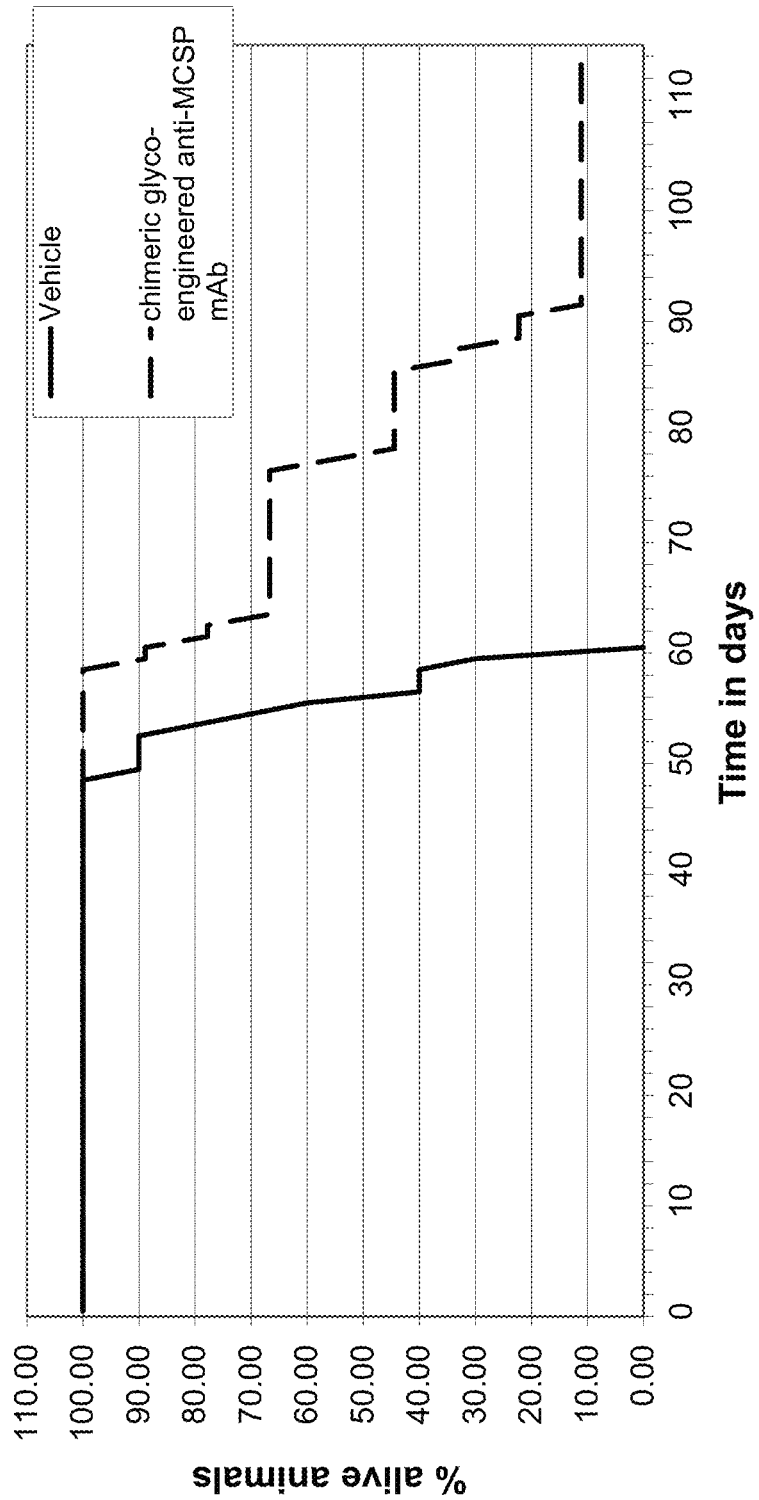
FIG. 12 depicts a survival curve showing that a chimeric glyco-engineered anti-MCSP antibody significantly increases survival time in FcgR3A transgenic SCID mice harboring a MDA-MB-435 tumor cell line as compared to the vehicle control.

As shown in FIG. 12, the chimeric glyco-engineered anti-MCSP antibody significantly increases survival time in this model as compared to the vehicle control.

9.3 MDA-MB-435 Cells in FcgR3 Transgenic SCID Mice

The same protocol as in Example 9.2 was followed, except that humanized antibody M4-3 ML2 (comprising the VH of SEQ ID NO: 32 and the VL of SEQ ID NO: 31) was compared to its parental, chimeric antibody LC007. Both of these antibodies are glycoengineered.

Results

Figure 13:
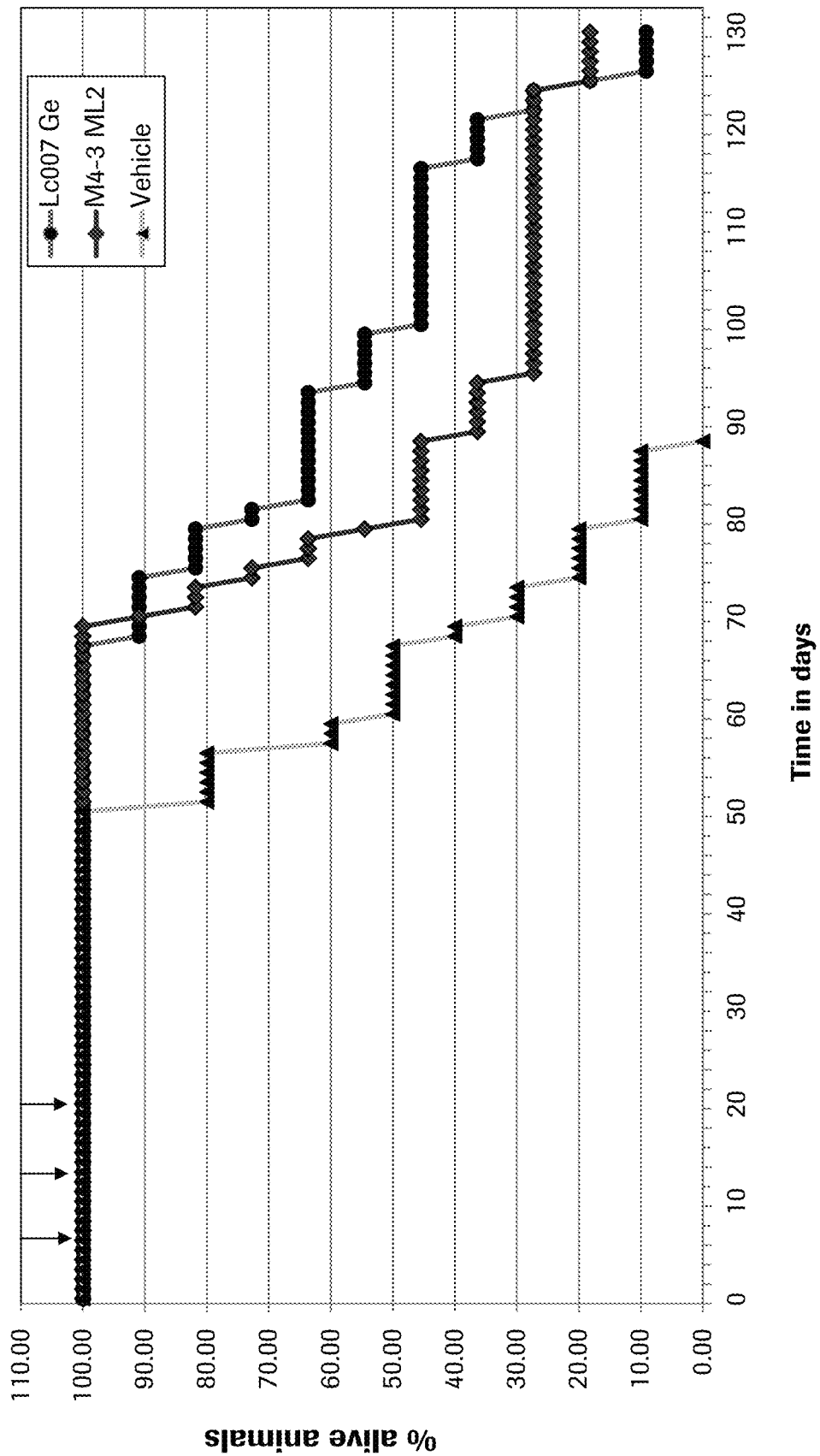
FIG. 13 depicts a survival curve showing that both the chimeric glyco-engineered anti-MCSP antibody and humanized variant thereof, M4-3 ML2, significantly increase survival time in FcgR3A transgenic SCID mice harboring a MDA-MB-435 tumor cell line as compared to the vehicle control.

As shown in FIG. 13 both the parental, chimeric antibody LC007 and humanized glyco-engineered variant thereof significantly increase survival time in this model as compared to the vehicle control.

TABLE A

Sequence Listing Description

| SEQ ID | Description |
| --- | --- |
| SEQ ID NO: 1 | Human MCSP |
| SEQ ID NO: 2 | MCSP Peptide (amino acids 2177-2221 of human MCSP) |
| SEQ ID NO: 3 | CSPG repeat 14 (amino acids 1937-2043 of human MCSP) |
| SEQ ID NO: 4 | CSPG repeat 15 (amino acids 2044-2246 of human MCSP) |
| SEQ ID NO: 5 | CSPG repeat 14-15 (amino acids 1937-2246 of human MCSP) |
| SEQ ID NO: 6 | CSPG repeat 13-15 (amino acids 1828-2246 of human MCSP) |

TABLE A-continued

Sequence Listing Description

| SEQ ID | Description |
|---|---|
| SEQ ID NO: 7 | CSPG repeat 12-15 (amino acids 1702-2246 of human MCSP) |
| SEQ ID NO: 8 | D3 domain of cynomologus MCSP (extracellular part) |
| SEQ ID NO: 9 | D3 domain of human MCSP (extracellular part) |
| SEQ ID NO: 10 | LC007 chimeric antibody HVR-L1 ML1 HVR-L1 |
| SEQ ID NO: 11 | LC007 chimeric antibody HVR-L2 ML1 HVR-L2 ML2 HVR-L2 |
| SEQ ID NO: 12 | LC007 chimeric antibody HVR-L3 LC007 humanized antibody ML1 HVR-L3 LC007 humanized antibody ML2 HVR-L3 |
| SEQ ID NO: 13 | LC007 humanized antibody ML2 HVR-L1 |
| SEQ ID NO: 14 | LC007 chimeric antibody HVR-H1 LC007 humanized antibody M4-1 HVR-H1 |
| SEQ ID NO: 15 | LC007 chimeric antibody HVR-H2 |
| SEQ ID NO: 16 | LC007 chimeric antibody HVR-H3 LC007 humanized antibody M4-1 HVR-H3 LC007 humanized antibody M4-3 HVR-H3 |
| SEQ ID NO: 17 | LC007 humanized antibody M4-3 HVR-H1 |
| SEQ ID NO: 18 | LC007 humanized antibody M4-1 HVR-H2 LC007 humanized antibody M4-3 HVR-H2 |
| SEQ ID NO: 19 | LC007 humanized antibody ML3 HVR-L1 |
| SEQ ID NO: 20 | LC007 humanized antibody L7A HVR-L1 |
| SEQ ID NO: 21 | LC007 humanized antibody L7B HVR-L1 |
| SEQ ID NO: 22 | LC007 humanized antibody ML5 HVR-L2 |
| SEQ ID NO: 23 | LC007 humanized antibody L7C HVR-L2 |
| SEQ ID NO: 24 | LC007 humanized antibody L7D HVR-L2 |
| SEQ ID NO: 25 | LC007 humanized antibody M4-7 HVR-H1 |
| SEQ ID NO: 26 | LC007 chimeric antibody VL |
| SEQ ID NO: 27 | LC007 chimeric antibody VH |
| SEQ ID NO: 28 | LC007 humanized antibody ML1 VL |
| SEQ ID NO: 29 | LC007 humanized antibody M4-1 VH |
| SEQ ID NO: 30 | LC007 humanized antibody M4-2 VH |
| SEQ ID NO: 31 | LC007 humanized antibody ML2 VL |
| SEQ ID NO: 32 | LC007 humanized antibody M4-3 VH |
| SEQ ID NO: 33 | LC007 humanized antibody M4-6 VH |
| SEQ ID NO: 34 | LC007 chimeric antibody light chain |
| SEQ ID NO: 35 | LC007 chimeric antibody heavy chain |
| SEQ ID NO: 36 | LC007 humanized antibody ML2 light chain |
| SEQ ID NO: 37 | LC007 humanized antibody M4-3 heavy chain |
| SEQ ID NO: 38 | LC007 murine antibody light chain nucleic acid sequence |
| SEQ ID NO: 39 | LC007 murine antibody heavy chain nucleic acid sequence |
| SEQ ID NO: 40 | LC007 chimeric antibody light chain nucleic acid sequence |
| SEQ ID NO: 41 | LC007 chimeric antibody heavy chain nucleic acid sequence |
| SEQ ID NO: 42 | LC007 humanized antibody ML2 light chain nucleic acid sequence |
| SEQ ID NO: 43 | LC007 humanized antibody M4-3 heavy chain nucleic acid sequence |
| SEQ ID NO: 44 | MCSP Transmembrane domain |

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. An isolated antibody that binds to human Melanoma chondroitin sulfate proteoglycan (MCSP) wherein the antibody comprises (a) HVR-H1 comprising the amino acid sequence of SEQ ID NO: 17; (b) HVR-H2 comprising the amino acid sequence of SEQ ID NO: 18; and (c) HVR-H3 comprising the amino acid sequence of SEQ ID NO: 16.

2. The antibody of claim 1, further comprising (a) HVR-L1 comprising the amino acid sequence of SEQ ID NO: 13; (b) HVR-L2 comprising the amino acid sequence of SEQ ID NO: 11; and (c) HVR-L3 comprising the amino acid sequence of SEQ ID NO: 12.

3. An isolated antibody that binds to human Melanoma chondroitin sulfate proteoglycan (MCSP), wherein the antibody comprises (a) HVR-L1 comprising the amino acid sequence of SEQ ID NO:13; (b) HVR-L2 comprising the amino acid sequence of SEQ ID NO: 11; and (c) HVR-L3 comprising the amino acid sequence of SEQ ID NO: 12.

4. The antibody of claim 2, comprising (a) a VH sequence having at least 95% sequence identity to the amino acid sequence of SEQ ID NO: 32; (b) a VL sequence having at least 95% sequence identity to the amino acid sequence of SEQ ID NO: 31; or (c) a VH sequence as in (a) and a VL sequence as in (b).

5. The antibody of claim 4, comprising a VH sequence of SEQ ID NO: 32.

6. The antibody of claim 4, comprising a VL sequence of SEQ ID NO: 31.

7. The antibody of claim 4, comprising a VH sequence of SEQ ID NO: 32 and a VL sequence of SEQ ID NO: 31.

8. An immunoconjugate comprising the antibody of claim 2 and a cytotoxic agent.

9. A pharmaceutical formulation comprising the antibody of claim 2 and a pharmaceutically acceptable carrier.

10. The antibody of claim 2, wherein the antibody is a monoclonal, humanized, or chimeric antibody.

11. The antibody of claim 2, wherein the antibody is a full-length IgG class antibody.

12. The antibody of claim 11, wherein the antibody has been glycoengineered to modify the oligosaccharides in the Fc region and wherein the antibody has increased ADCC effector function as compared to an non-glycoengineered antibody.

13. The antibody of claim 12, wherein the Fc region has a reduced number of fucose residues as compared to the non-glycoengineered antibody.

14. The antibody of claim 12, wherein the antibody has an increased ratio of GlcNAc residues to fucose residues in the Fc region compared to the non-glycoengineered antibody.

15. The antibody of claim 12, wherein the Fc region has an increased proportion of bisected oligosaccharides as compared to the non-glycoengineered antibody.

16. The antibody of claim 7, wherein the antibody is a monoclonal, humanized, or chimeric antibody.

17. The antibody of claim 7, wherein the antibody is a full-length IgG class antibody.

18. The antibody of claim 17, wherein the antibody has been glycoengineered to modify the oligosaccharides in the Fc region and wherein the antibody has increased ADCC effector function as compared to an non-glycoengineered antibody.

19. The antibody of claim 18, wherein the Fc region has a reduced number of fucose residues as compared to the non-glycoengineered antibody.

20. The antibody of claim 18, wherein the antibody has an increased ratio of GlcNAc residues to fucose residues in the Fc region compared to the non-glycoengineered antibody.

21. The antibody of claim 18, wherein the Fc region has an increased proportion of bisected oligosaccharides as compared to the non-glycoengineered antibody.

* * * * *